(12) United States Patent
Scheib et al.

(10) Patent No.: US 11,957,382 B2
(45) Date of Patent: Apr. 16, 2024

(54) ROBOTICALLY CONTROLLED UTERINE MANIPULATOR WITH ARTICULATION

(71) Applicant: Cilag GmbH International, Zug (CH)

(72) Inventors: Charles J. Scheib, Loveland, OH (US); Matthew Vargas, San Francisco, CA (US); Clinton Denlinger, Cincinnati, OH (US)

(73) Assignee: Cilag GmbH International, Zug (CH)

(*) Notice: Subject to any disclaimer, the term of this patent is extended or adjusted under 35 U.S.C. 154(b) by 154 days.

(21) Appl. No.: 17/468,767

(22) Filed: Sep. 8, 2021

(65) Prior Publication Data

US 2023/0074350 A1 Mar. 9, 2023

(51) Int. Cl.

| | | |
|---|---|---|
| *A61B 17/42* | (2006.01) | |
| *A61B 17/00* | (2006.01) | |
| *A61B 17/12* | (2006.01) | |
| *A61B 34/30* | (2016.01) | |
| *A61G 13/10* | (2006.01) | |
| *A61M 25/10* | (2013.01) | |

(52) U.S. Cl.
CPC .... *A61B 17/4241* (2013.01); *A61B 17/00234* (2013.01); *A61B 17/12136* (2013.01); *A61B 34/30* (2016.02); *A61G 13/10* (2013.01); *A61M 25/1011* (2013.01); *A61B 2017/00199* (2013.01); *A61B 2017/00314* (2013.01); *A61B 2017/00367* (2013.01); *A61B 2017/00818* (2013.01); *A61B 2017/4225* (2013.01); *A61B 2034/302* (2016.02)

(58) Field of Classification Search
CPC .............. A61B 17/4241; A61B 17/42; A61B 2017/4216; A61B 2017/4225
See application file for complete search history.

(56) References Cited

U.S. PATENT DOCUMENTS

| | | | |
|---|---|---|---|
| 5,643,285 A * | 7/1997 | Rowden | A61B 17/4241 606/119 |
| 9,636,144 B2 * | 5/2017 | Parys | A61B 17/4241 |
| 9,743,955 B2 | 8/2017 | Hill | |
| 9,763,741 B2 | 9/2017 | Alvarez | |
| 9,788,859 B2 | 10/2017 | Parys | |
| 10,464,209 B2 | 11/2019 | Ho | |
| 10,639,072 B2 | 5/2020 | Ahluwalia | |
| 10,667,875 B2 | 6/2020 | DeFonzo | |
| 10,765,303 B2 | 9/2020 | Graetzel | |
| 10,827,913 B2 | 11/2020 | Ummalaneni | |
| 10,881,280 B2 | 1/2021 | Baez, Jr. | |
| 10,898,277 B2 | 1/2021 | Srinivasan | |
| 11,058,493 B2 | 7/2021 | Rafil-Tari | |
| 2011/0022073 A1 * | 1/2011 | Gross | A61B 5/14552 606/193 |

(Continued)

*Primary Examiner* — Ashley L Fishback

(57) ABSTRACT

An apparatus includes a shaft including a distal shaft end. At least a portion of the shaft defines a first axis. The apparatus also includes a sleeve slidably coupled to the shaft. The sleeve includes a distal sleeve end. The apparatus further includes a colpotomy cup fixedly secured to the distal sleeve end, and a movable member extending distally from the distal shaft end. The movable member is configured to move relative to the shaft between a first state in which the movable member extends substantially along the first axis and a second state in which the movable member extends at least partially along a second axis transverse to the first axis for manipulating an anatomical structure.

20 Claims, 37 Drawing Sheets

(56) References Cited

U.S. PATENT DOCUMENTS

| | | | |
|---|---|---|---|
| 2016/0183977 A1* | 6/2016 | Marshburn | A61B 17/42 |
| | | | 606/191 |
| 2017/0128127 A1* | 5/2017 | Skalnyi | A61B 18/1485 |
| 2017/0325844 A1* | 11/2017 | Prior | A61B 1/00082 |
| 2018/0325552 A1 | 11/2018 | Weihe | |
| 2018/0325554 A1* | 11/2018 | Prior | A61B 17/4241 |
| 2018/0344183 A1* | 12/2018 | McKinney | A61B 5/4325 |
| 2019/0083133 A1* | 3/2019 | Prior | A61B 17/4241 |
| 2019/0254708 A1* | 8/2019 | Wu | A61B 17/12099 |
| 2020/0253676 A1* | 8/2020 | Traina | A61B 34/30 |
| 2020/0289799 A1* | 9/2020 | Begg | A61B 17/1204 |
| 2020/0337729 A1* | 10/2020 | Begg | A61B 17/4241 |
| 2021/0100584 A1 | 4/2021 | Einarsson | |
| 2022/0192707 A1* | 6/2022 | Barakat | A61B 34/30 |

* cited by examiner

ROBOTICALLY CONTROLLED UTERINE MANIPULATOR WITH ARTICULATION

BACKGROUND

A variety of medical instruments may be used in procedures conducted by a medical professional operator, as well as applications in robotically assisted surgeries. In the case of robotically assisted surgery, the clinician may operate a master controller to remotely control the motion of such medical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletol gloves, master manipulators, or the like), which are coupled by a servo mechanism to the medical instrument. In some scenarios, a servo motor moves a manipulator supporting the medical instrument based on the clinician's manipulation of the hand input devices. During the medical procedure, the clinician may employ, via a robotic system, a variety of medical instruments including an ultrasonic blade, a surgical stapler, a tissue grasper, a needle driver, an electrosurgical cautery probes, etc. Each of these structures performs functions for the clinician, for example, cutting tissue, coagulating tissue, holding or driving a needle, grasping a blood vessel, dissecting tissue, or cauterizing tissue.

Examples of robotic systems are described in U.S. Pat. No. 9,763,741, entitled "System for Robotic-Assisted Endolumenal Surgery and Related Methods," issued Sep. 19, 2017, the disclosure of which is incorporated by reference herein, in its entirety; U.S. Pat. No. 10,464,209, entitled "Robotic System with Indication of Boundary for Robotic Arm," issued Nov. 5, 2019, the disclosure of which is incorporated by reference herein, in its entirety; U.S. Pat. No. 10,667,875, entitled "Systems and Techniques for Providing Multiple Perspectives During Medical Procedures," issued Jun. 2, 2020, the disclosure of which is incorporated by reference herein, in its entirety; U.S. Pat. No. 10,765,303, entitled "System and Method for Driving Medical Instrument," issued Sep. 8, 2020, the disclosure of which is incorporated by reference herein, in its entirety; U.S. Pat. No. 10,827,913, entitled "Systems and Methods for Displaying Estimated Location of Instrument," issued Nov. 10, 2020, the disclosure of which is incorporated by reference herein, in its entirety; U.S. Pat. No. 10,881,280, entitled "Manually and Robotically Controllable Medical Instruments," issued Jan. 5, 2021, the disclosure of which is incorporated by reference herein, in its entirety; U.S. Pat. No. 10,898,277, entitled "Systems and Methods for Registration of Location Sensors," issued Jan. 26, 2012, the disclosure of which is incorporated by reference herein, in its entirety; and U.S. Pat. No. 11,058,493, entitled "Robotic System Configured for Navigation Path Tracing," issued Jul. 13, 2021, the disclosure of which is incorporated by reference herein, in its entirety.

During a hysterectomy procedure, a colpotomy may be performed at the cervicovaginal junction. Such procedures may include the use of a uterine manipulator that includes a colpotomy cup or similar structure. Examples of instruments that may be used during a hysterectomy procedure are described in U.S. Pat. No. 9,743,955, entitled "Intracorporeal Transilluminator of Tissue Using LED Array," issued Aug. 29, 2017; U.S. Pat. No. 9,788,859, entitled "Uterine Manipulators and Related Components and Methods," issued Oct. 17, 2017; U.S. Pat. No. 10,639,072, entitled "Uterine Manipulator," issued May 5, 2020; U.S. Pub. No. 2021/0100584, entitled "Uterine Manipulator," published Apr. 8, 2021; and U.S. Pub. No. 2018/0325552, entitled "Colpotomy Systems, Devices, and Methods with Rotational Cutting," published Nov. 15, 2018.

While several medical instruments, systems, and methods have been made and used, it is believed that no one prior to the inventors has made or used the invention described in the appended claims.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

I. Overview of Example of Robotic System

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Example of Robotic System Cart

Figure 1:
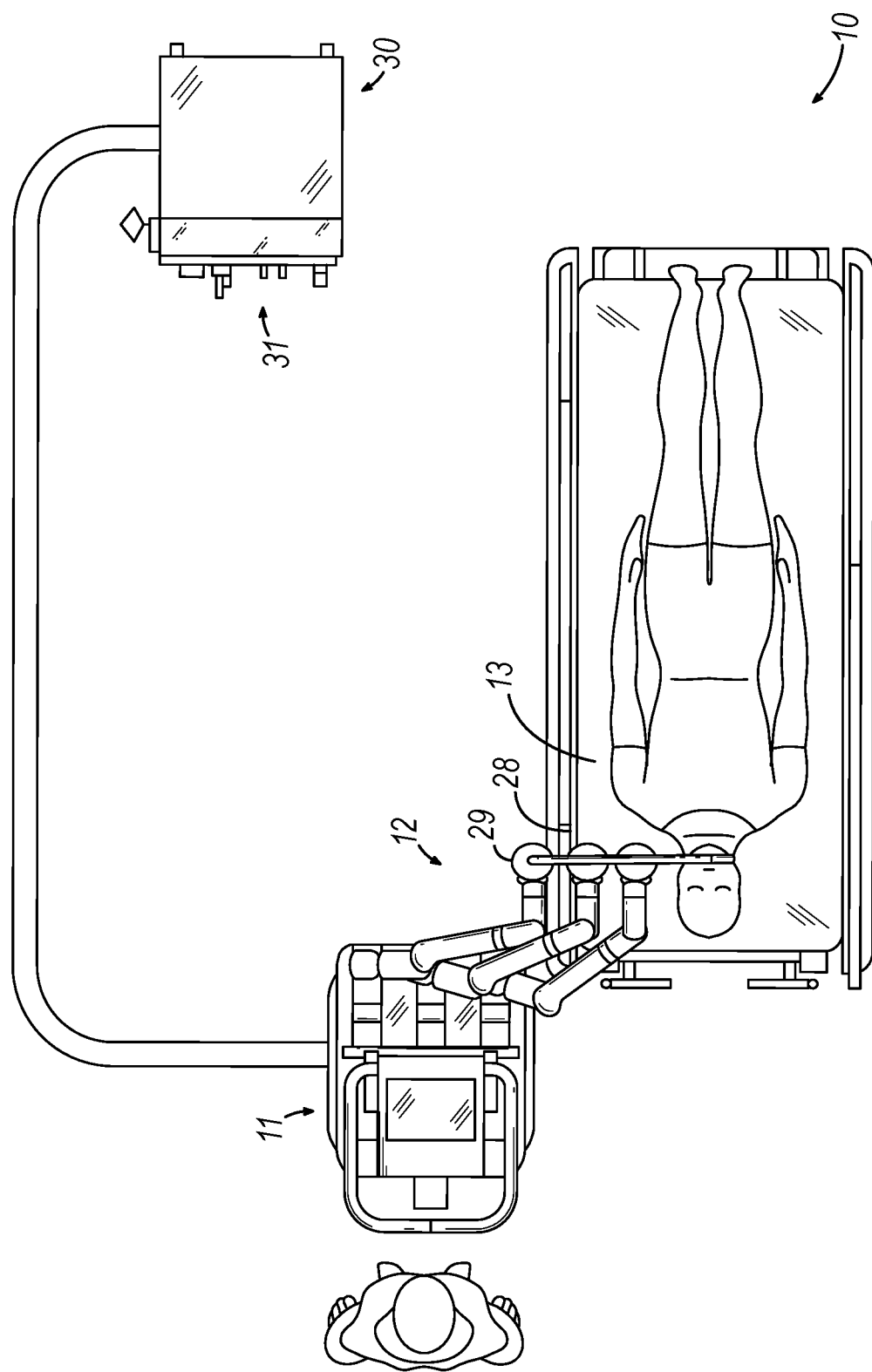
FIG. 1 depicts an embodiment of a cart-based robotic system arranged for diagnostic and/or therapeutic bronchoscopy procedure(s)
Figure 2:
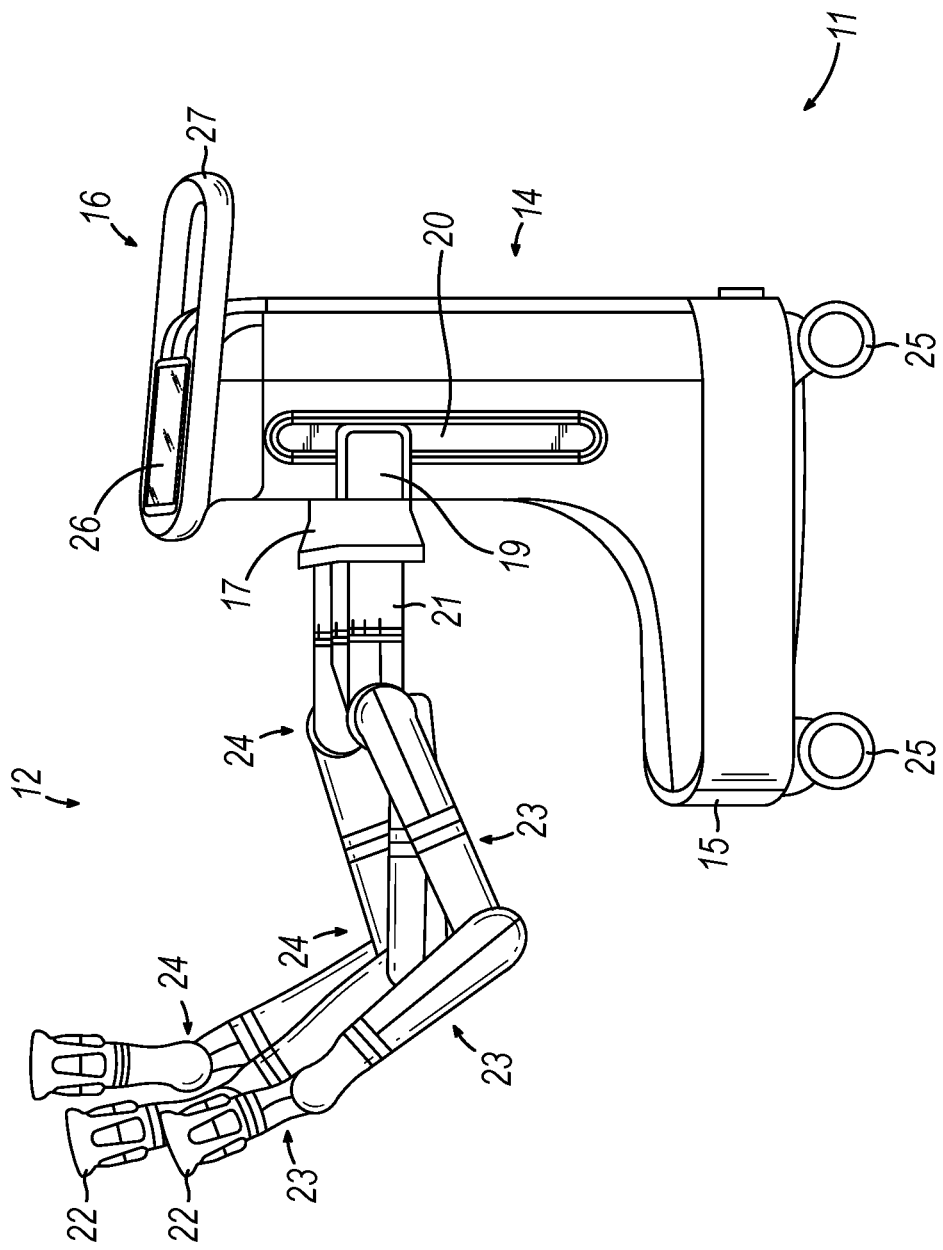
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system (10) arranged for a diagnostic and/or therapeutic bronchoscopy procedure. During a bronchoscopy, the system (10) may comprise a cart (11) having one or more robotic arms (12) to deliver a medical instrument, such as a steerable endoscope (13), which may be a procedure-specific bronchoscope for bronchoscopy, to a natural orifice access point (i.e., the mouth of the patient positioned on a table in the present example) to deliver diagnostic and/or therapeutic tools. As shown, the cart (11) may be positioned proximate to the patient's upper torso in order to provide access to the access point. Similarly, the robotic arms (12) may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart (11) is properly positioned, the robotic arms (12) may insert the steerable endoscope (13) into the patient robotically, manually, or a combination thereof. As shown, the steerable endoscope (13) may comprise at least two telescoping parts, such as an inner leader portion and an outer sheath portion, each portion coupled to a separate instrument driver from the set of instrument drivers (28), each instrument driver coupled to the distal end of an individual robotic arm. This linear arrangement of the instrument drivers (28), which facilitates coaxially aligning the leader portion with the sheath portion, creates a "virtual rail" (29) that may be repositioned in space by manipulating the one or more robotic arms (12) into different angles and/or positions. The virtual rails described herein are depicted in the Figures using dashed lines, and accordingly the dashed lines do not depict any physical structure of the system. Translation of the instrument drivers (28) along the virtual rail (29) telescopes the inner leader portion relative to the outer sheath portion or advances or retracts the endoscope (13) from the patient. The angle of the virtual rail (29) may be adjusted, translated, and pivoted based on clinical application or physician preference. For example, in bronchoscopy, the angle and position of the virtual rail (29) as shown represents a compromise between providing physician access to the endoscope (13) while minimizing friction that results from bending the endoscope (13) into the patient's mouth.

The endoscope (13) may be directed down the patient's trachea and lungs after insertion using precise commands from the robotic system until reaching the target destination or operative site. In order to enhance navigation through the patient's lung network and/or reach the desired target, the endoscope (13) may be manipulated to telescopically extend the inner leader portion from the outer sheath portion to obtain enhanced articulation and greater bend radius. The use of separate instrument drivers (28) also allows the leader portion and sheath portion to be driven independent of each other.

For example, the endoscope (13) may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope (13) may endoscopically deliver tools to resect the potentially cancerous tissue. In some instances, diagnostic and therapeutic treatments can be delivered in separate procedures. In those circumstances, the endoscope (13) may also be used to deliver a fiducial to "mark" the location of the target nodule as well. In other instances, diagnostic and therapeutic treatments may be delivered during the same procedure.

The system (10) may also include a movable tower (30), which may be connected via support cables to the cart (11) to provide support for controls, electronics, fluidics, optics, sensors, and/or power to the cart (11). Placing such functionality in the tower (30) allows for a smaller form factor cart (11) that may be more easily adjusted and/or re-positioned by an operating physician and his/her staff. Additionally, the division of functionality between the cart/table and the support tower (30) reduces operating room clutter and facilitates improving clinical workflow. While the cart (11) may be positioned close to the patient, the tower (30) may be stowed in a remote location to stay out of the way during a procedure.

In support of the robotic systems described above, the tower (30) may include component(s) of a computer-based control system that stores computer program instructions, for example, within a non-transitory computer-readable storage medium such as a persistent magnetic storage drive, solid state drive, etc. The execution of those instructions, whether the execution occurs in the tower (30) or the cart (11), may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower (30) may also include a pump, flow meter, valve control, and/or fluid access in order to provide controlled irrigation and aspiration capabilities to the system that may be deployed through the endoscope (13). These components may also be controlled using the computer system of tower (30). In some embodiments, irrigation and aspiration capabilities may be delivered directly to the endoscope (13) through separate cable(s).

The tower (30) may include a voltage and surge protector designed to provide filtered and protected electrical power to the cart (11), thereby avoiding placement of a power transformer and other auxiliary power components in the cart (11), resulting in a smaller, more moveable cart (11).

The tower (30) may also include support equipment for the sensors deployed throughout the robotic system (10). For example, the tower (30) may include opto-electronics equipment for detecting, receiving, and processing data received from the optical sensors or cameras throughout the robotic system (10). In combination with the control system, such opto-electronics equipment may be used to generate real-time images for display in any number of consoles deployed throughout the system, including in the tower (30). Similarly, the tower (30) may also include an electronic subsystem for receiving and processing signals received from deployed electromagnetic (EM) sensors. The tower (30) may also be used to house and position an EM field generator for detection by EM sensors in or on the medical instrument.

The tower (30) may also include a console (31) in addition to other consoles available in the rest of the system, e.g., console mounted on top of the cart. The console (31) may include a user interface and a display screen, such as a touchscreen, for the physician operator. Consoles in system (10) are generally designed to provide both robotic controls as well as pre-operative and real-time information of the procedure, such as navigational and localization information of the endoscope (13). When the console (31) is not the only console available to the physician, it may be used by a second operator, such as a nurse, to monitor the health or vitals of the patient and the operation of system, as well as provide procedure-specific data, such as navigational and localization information. In other embodiments, the console (31) is housed in a body that is separate from the tower (30).

The tower (30) may be coupled to the cart (11) and endoscope (13) through one or more cables or connections (not shown). In some embodiments, the support functionality from the tower (30) may be provided through a single cable to the cart (11), simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart (11) generally includes an elongated support structure (14) (often referred to as a "column"), a cart base (15), and a console (16) at the top of the column (14). The column (14) may include one or more carriages, such as a carriage (17) (alternatively "arm support") for supporting the deployment of one or more robotic arms (12) (three shown in FIG. 2). The carriage (17) may include individually configurable arm mounts that rotate along a perpendicular axis to adjust the base of the robotic arms (12) for better positioning relative to the patient. The carriage (17) also includes a carriage interface (19) that allows the carriage (17) to vertically translate along the column (14).

The carriage interface (19) is connected to the column (14) through slots, such as slot (20), that are positioned on opposite sides of the column (14) to guide the vertical translation of the carriage (17). The slot (20) contains a vertical translation interface to position and hold the carriage at various vertical heights relative to the cart base (15). Vertical translation of the carriage (17) allows the cart (11) to adjust the reach of the robotic arms (12) to meet a variety of table heights, patient sizes, and physician preferences. Similarly, the individually configurable arm mounts on the carriage (17) allow the robotic arm base (21) of robotic arms (12) to be angled in a variety of configurations.

In some embodiments, the slot (20) may be supplemented with slot covers that are flush and parallel to the slot surface to prevent dirt and fluid ingress into the internal chambers of the column (14) and the vertical translation interface as the carriage (17) vertically translates. The slot covers may be deployed through pairs of spring spools positioned near the vertical top and bottom of the slot (20). The covers are coiled within the spools until deployed to extend and retract from their coiled state as the carriage (17) vertically translates up and down. The spring-loading of the spools provides force to retract the cover into a spool when carriage (17) translates towards the spool, while also maintaining a tight seal when the carriage (17) translates away from the spool. The covers may be connected to the carriage (17) using, for example, brackets in the carriage interface (19) to ensure proper extension and retraction of the cover as the carriage (17) translates.

The column (14) may internally comprise mechanisms, such as gears and motors, that are designed to use a vertically aligned lead screw to translate the carriage (17) in a mechanized fashion in response to control signals generated in response to user inputs, e.g., inputs from the console (16).

The robotic arms (12) may generally comprise robotic arm bases (21) and end effectors (22), separated by a series of linkages (23) that are connected by a series of joints (24), each joint comprising an independent actuator, each actuator comprising an independently controllable motor. Each independently controllable joint represents an independent degree of freedom available to the robotic arm. Each of the arms (12) have seven joints, and thus provide seven degrees of freedom. A multitude of joints result in a multitude of degrees of freedom, allowing for "redundant" degrees of freedom. Redundant degrees of freedom allow the robotic arms (12) to position their respective end effectors (22) at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base (15) balances the weight of the column (14), carriage (17), and arms (12) over the floor. Accordingly, the cart base (15) houses heavier components, such as electronics, motors, power supply, as well as components that either enable movement and/or immobilize the cart. For example, the cart base (15) includes rollable wheel-shaped casters (25) that allow for the cart to easily move around the room prior to a procedure. After reaching the appropriate position, the casters (25) may be immobilized using wheel locks to hold the cart (11) in place during the procedure.

Positioned at the vertical end of column (14), the console (16) allows for both a user interface for receiving user input and a display screen (or a dual-purpose device such as, for example, a touchscreen (26)) to provide the physician user with both pre-operative and intra-operative data. Potential pre-operative data on the touchscreen (26) may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console (16) may be positioned and tilted to allow a physician to access the console from the side of the column (14) opposite carriage (17). From this position, the physician may view the console (16), robotic arms (12), and patient while operating the console (16) from behind the cart (11). As shown, the console (16) also includes a handle (27) to assist with maneuvering and stabilizing cart (11).

Figure 3:
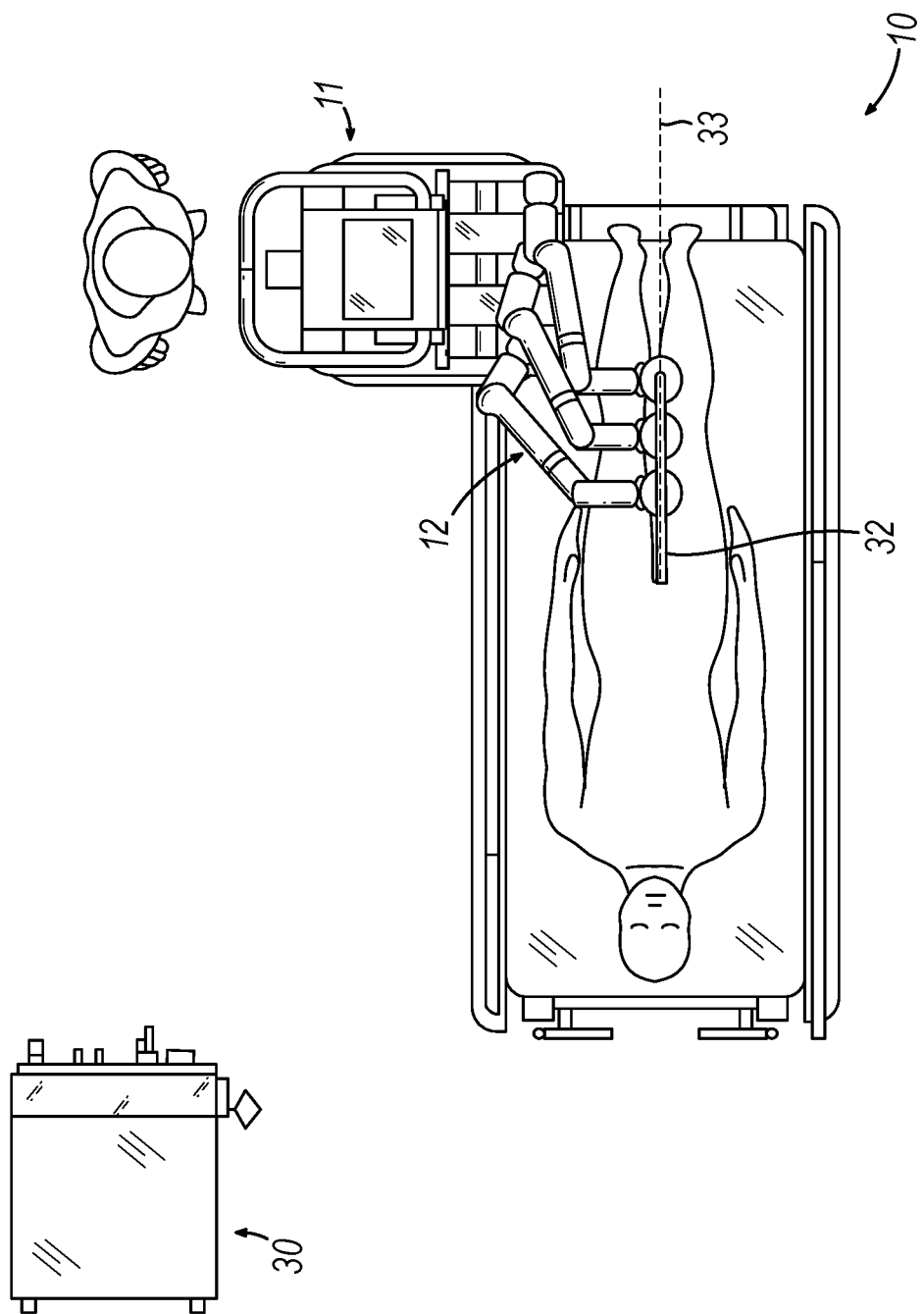
FIG. 3 depicts an embodiment of the robotic system of FIG. 1 arranged for ureteroscopy.

FIG. 3 illustrates an embodiment of a robotically-enabled system (10) arranged for ureteroscopy. In a ureteroscopic procedure, the cart (11) may be positioned to deliver a ureteroscope (32), a procedure-specific endoscope designed to traverse a patient's urethra and ureter, to the lower abdominal area of the patient. In a ureteroscopy, it may be desirable for the ureteroscope (32) to be directly aligned with the patient's urethra to reduce friction and forces on the sensitive anatomy in the area. As shown, the cart (11) may be aligned at the foot of the table to allow the robotic arms (12) to position the ureteroscope (32) for direct linear access to the patient's urethra. From the foot of the table, the robotic arms (12) may insert the ureteroscope (32) along the virtual rail (33) directly into the patient's lower abdomen through the urethra.

After insertion into the urethra, using similar control techniques as in bronchoscopy, the ureteroscope (32) may be navigated into the bladder, ureters, and/or kidneys for diagnostic and/or therapeutic applications. For example, the ureteroscope (32) may be directed into the ureter and kidneys to break up kidney stone build up using a laser or ultrasonic lithotripsy device deployed down the working channel of the ureteroscope (32). After lithotripsy is complete, the resulting stone fragments may be removed using baskets deployed down the ureteroscope (32).

Figure 4:
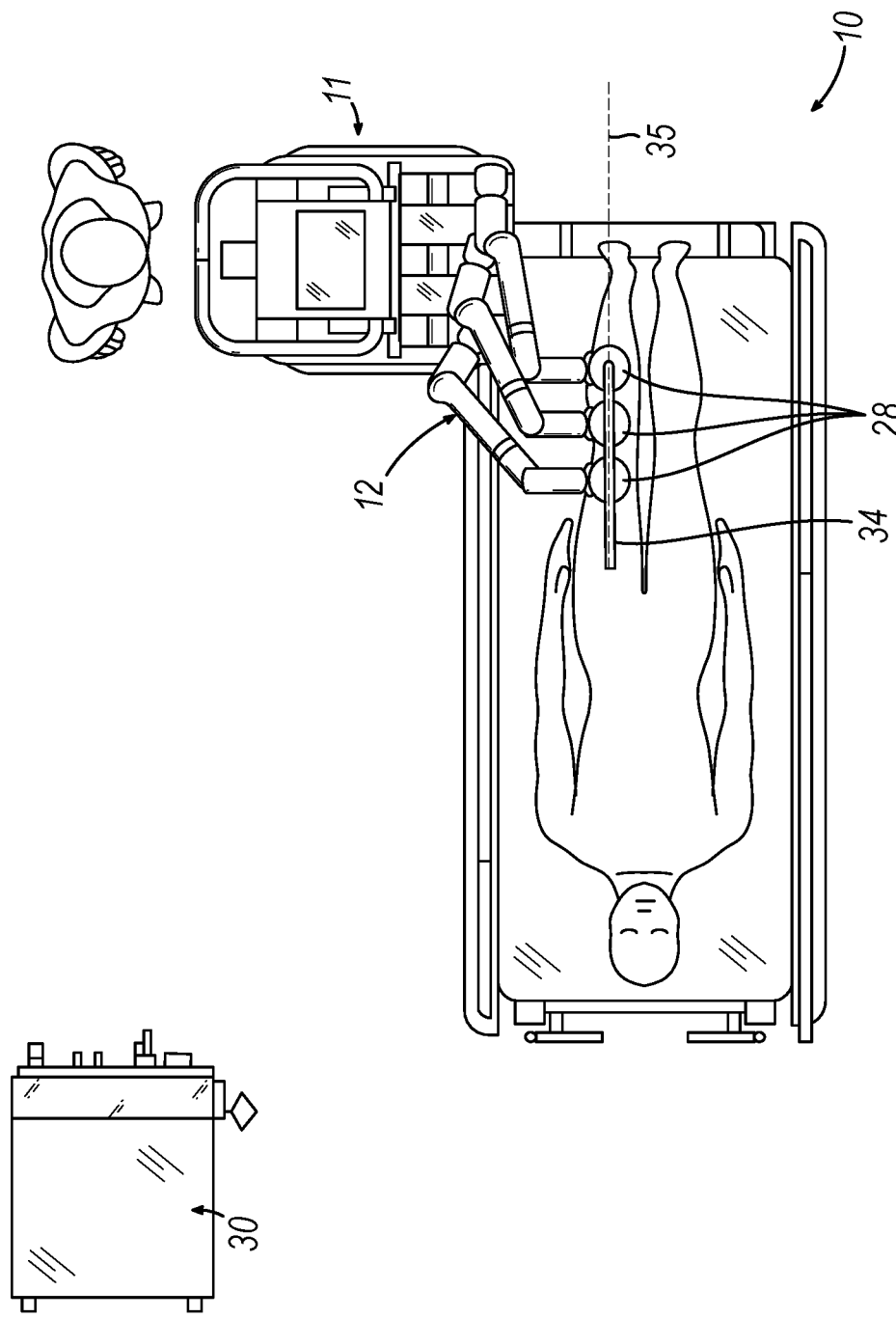
FIG. 4 depicts an embodiment of the robotic system of FIG. 1 arranged for a vascular procedure.

FIG. 4 illustrates an embodiment of a robotically-enabled system similarly arranged for a vascular procedure. In a vascular procedure, the system (10) may be configured such that the cart (11) may deliver a medical instrument (34), such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart (11) may be positioned towards the patient's legs and lower abdomen to allow the robotic arms (12) to provide a virtual rail (35) with direct linear access to the femoral artery access point in the patient's thigh/hip region. After insertion into the artery, the medical instrument (34) may be directed and inserted by translating the instrument drivers (28). Alternatively, the cart may be positioned around the patient's upper abdomen in order to reach alternative vascular access points, such as, for example, the carotid and brachial arteries near the shoulder and wrist.

B. Example of Robotic System Table

Figure 5:
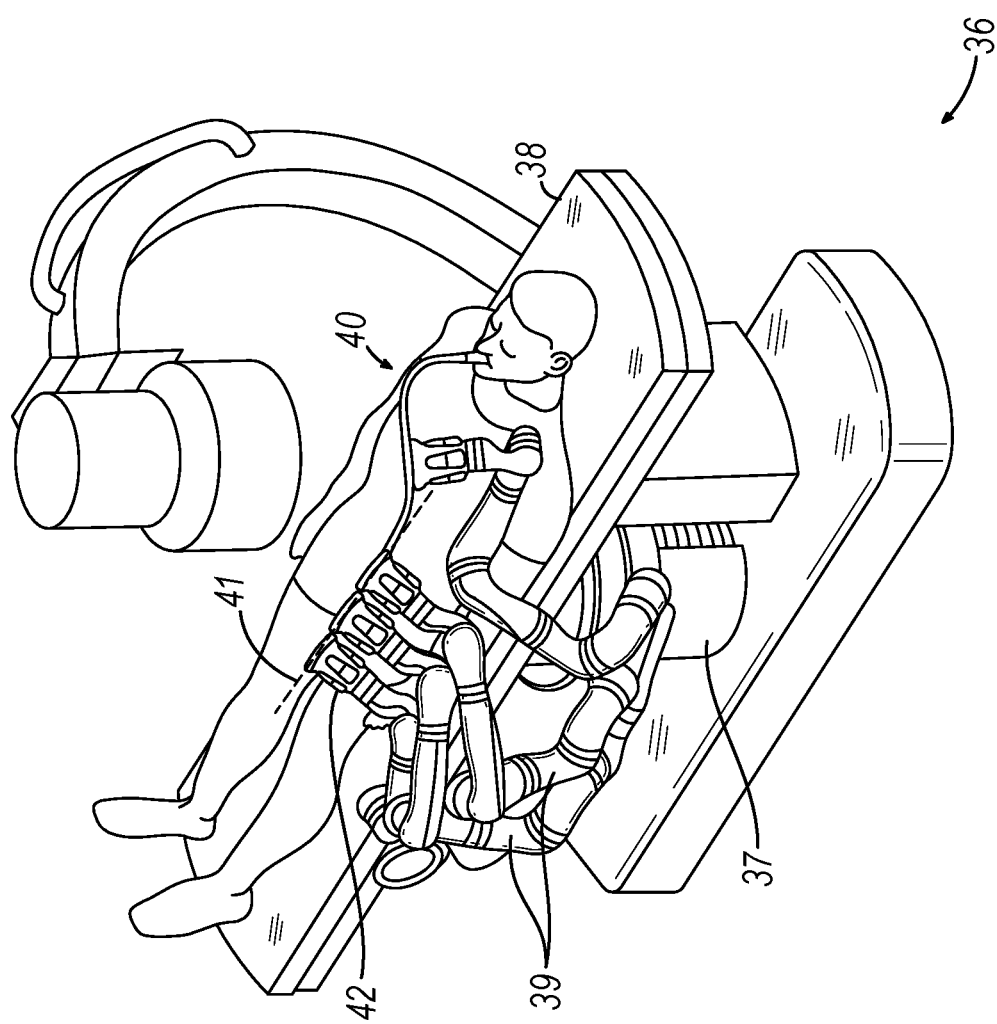
FIG. 5 depicts an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System (36) includes a support structure or column (37) for supporting platform (38) (shown as a "table" or "bed") over the floor. Much like in the cart-based systems, the end effectors of the robotic arms (39) of the system (36) comprise instrument drivers (42) that are designed to manipulate an elongated medical instrument, such as a bronchoscope (40) in FIG. 5, through or along a virtual rail (41) formed from the linear alignment of the instrument drivers (42). In practice, a C-arm for providing fluoroscopic imaging may be positioned over the patient's upper abdominal area by placing the emitter and detector around table (38).

Figure 6:
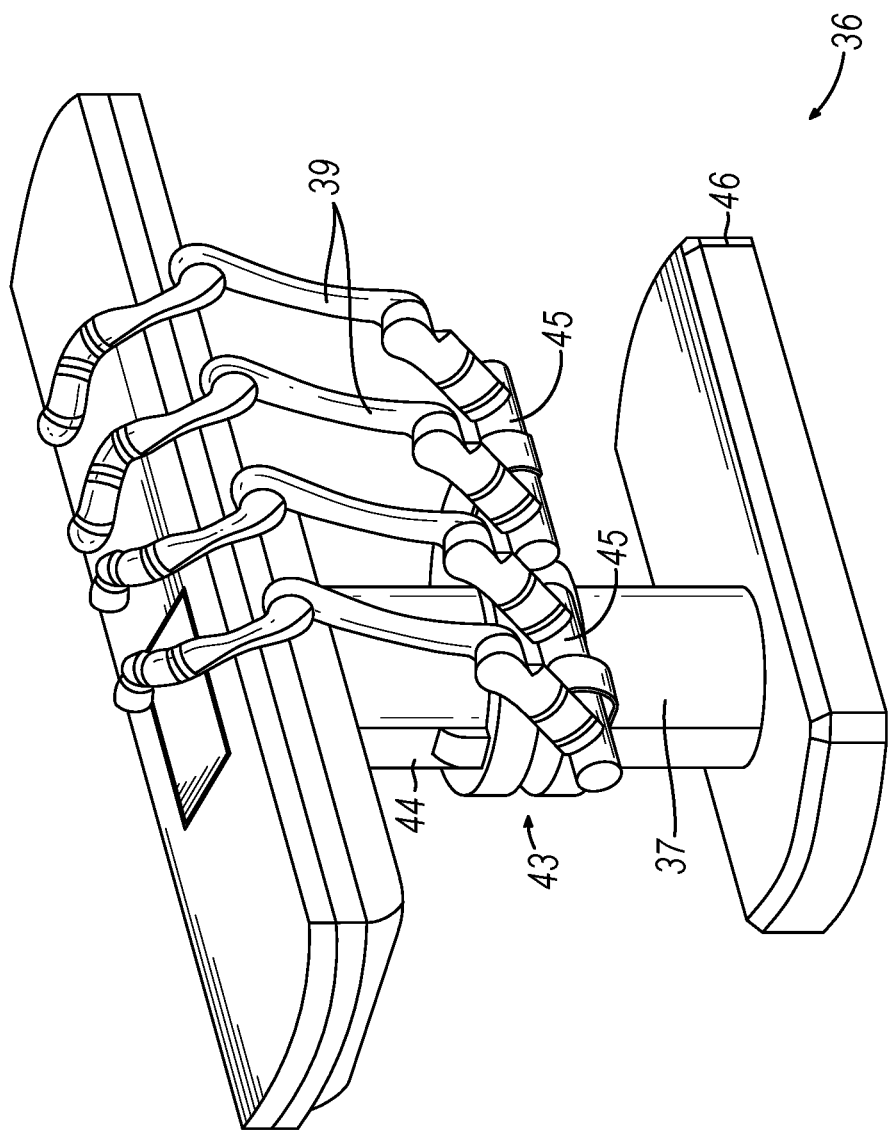
FIG. 6 provides an alternative view of the robotic system of FIG. 5.

FIG. 6 provides an alternative view of the system (36) without the patient and medical instrument for discussion purposes. As shown, the column (37) may include one or more carriages (43) shown as ring-shaped in the system (36), from which the one or more robotic arms (39) may be based. The carriages (43) may translate along a vertical column interface 44 that runs the length of the column (37) to provide different vantage points from which the robotic arms (39) may be positioned to reach the patient. The carriage(s) (43) may rotate around the column (37) using a mechanical motor positioned within the column (37) to allow the robotic arms (39) to have access to multiples sides of the table (38), such as, for example, both sides of the patient. In embodiments with multiple carriages, the carriages may be individually positioned on the column and may translate and/or rotate independent of the other carriages. While carriages (43) need not surround the column (37) or even be circular, the ring-shape as shown facilitates rotation of the carriages (43) around the column (37) while maintaining structural balance. Rotation and translation of the carriages (43) allows the system to align the medical instruments, such as endoscopes and laparoscopes, into different access points on the patient. In other embodiments (not shown), the system (36) can include a patient table or bed with adjustable arm supports in the form of bars or rails extending alongside it. One or more robotic arms (39) (e.g., via a shoulder with an elbow joint) can be attached to the adjustable arm supports, which can be vertically adjusted. By providing vertical adjustment, the robotic arms (39) are advantageously capable of being stowed compactly beneath the patient table or bed, and subsequently raised during a procedure.

Figure 9:
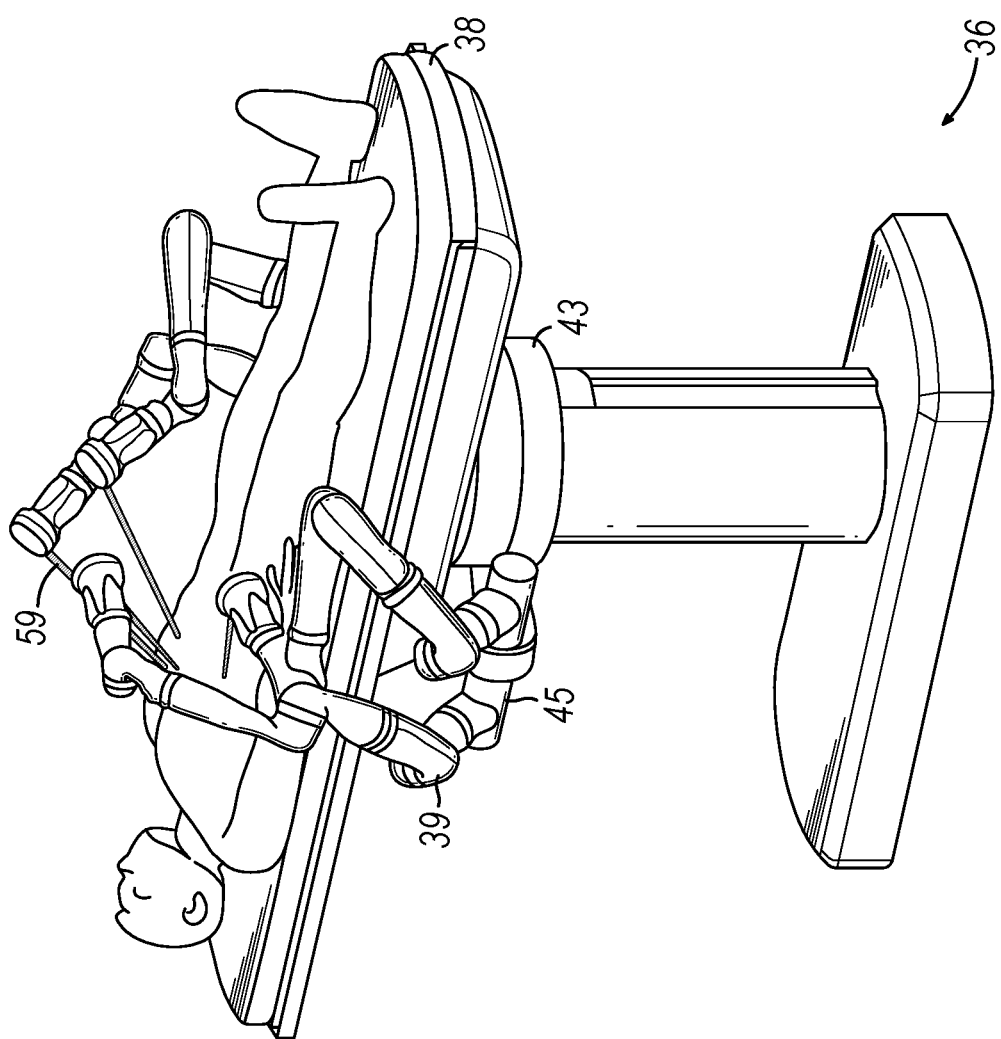
FIG. 9 depicts an embodiment of a table-based robotic system configured for a laparoscopic procedure.

The arms (39) may be mounted on the carriages through a set of arm mounts (45) comprising a series of joints that may individually rotate and/or telescopically extend to provide additional configurability to the robotic arms (39). Additionally, the arm mounts (45) may be positioned on the carriages (43) such that, when the carriages (43) are appropriately rotated, the arm mounts (45) may be positioned on either the same side of table (38) (as shown in FIG. 6), on opposite sides of table (38) (as shown in FIG. 9), or on adjacent sides of the table (38) (not shown).

The column (37) structurally provides support for the table (38), and a path for vertical translation of the carriages. Internally, the column (37) may be equipped with lead screws for guiding vertical translation of the carriages, and motors to mechanize the translation of said carriages based the lead screws. The column (37) may also convey power and control signals to the carriage (43) and robotic arms (39) mounted thereon.

The table base (46) serves a similar function as the cart base (15) in cart (11) shown in FIG. 2, housing heavier components to balance the table/bed (38), the column (37), the carriages (43), and the robotic arms (39). The table base (46) may also incorporate rigid casters to provide stability during procedures. Deployed from the bottom of the table base (46), the casters may extend in opposite directions on both sides of the base (46) and retract when the system (36) needs to be moved.

Continuing with FIG. 6, the system (36) may also include a tower (not shown) that divides the functionality of System (36) between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
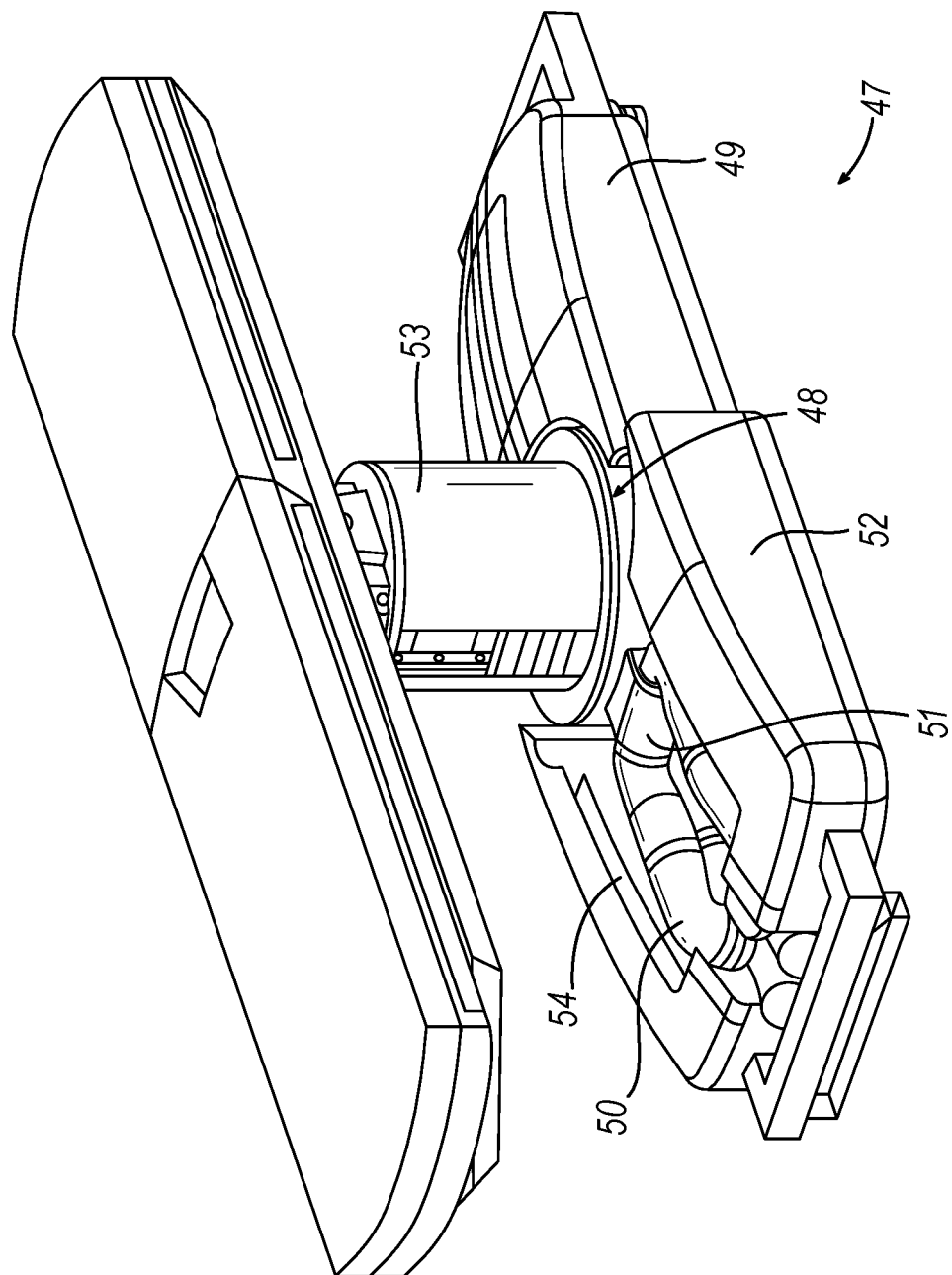
FIG. 7 depicts an example system configured to stow robotic arm(s)

In some embodiments, a table base may stow and store the robotic arms when not in use. FIG. 7 illustrates a system (47) that stows robotic arms in an embodiment of the table-based system. In system (47), carriages (48) may be vertically translated into base (49) to stow robotic arms (50), arm mounts (51), and the carriages (48) within the base (49). Base covers (52) may be translated and retracted open to deploy the carriages (48), arm mounts (51), and arms (50) around column (53), and closed to stow to protect them when not in use. The base covers (52) may be sealed with a membrane (54) along the edges of its opening to prevent dirt and fluid ingress when closed.

Figure 8:
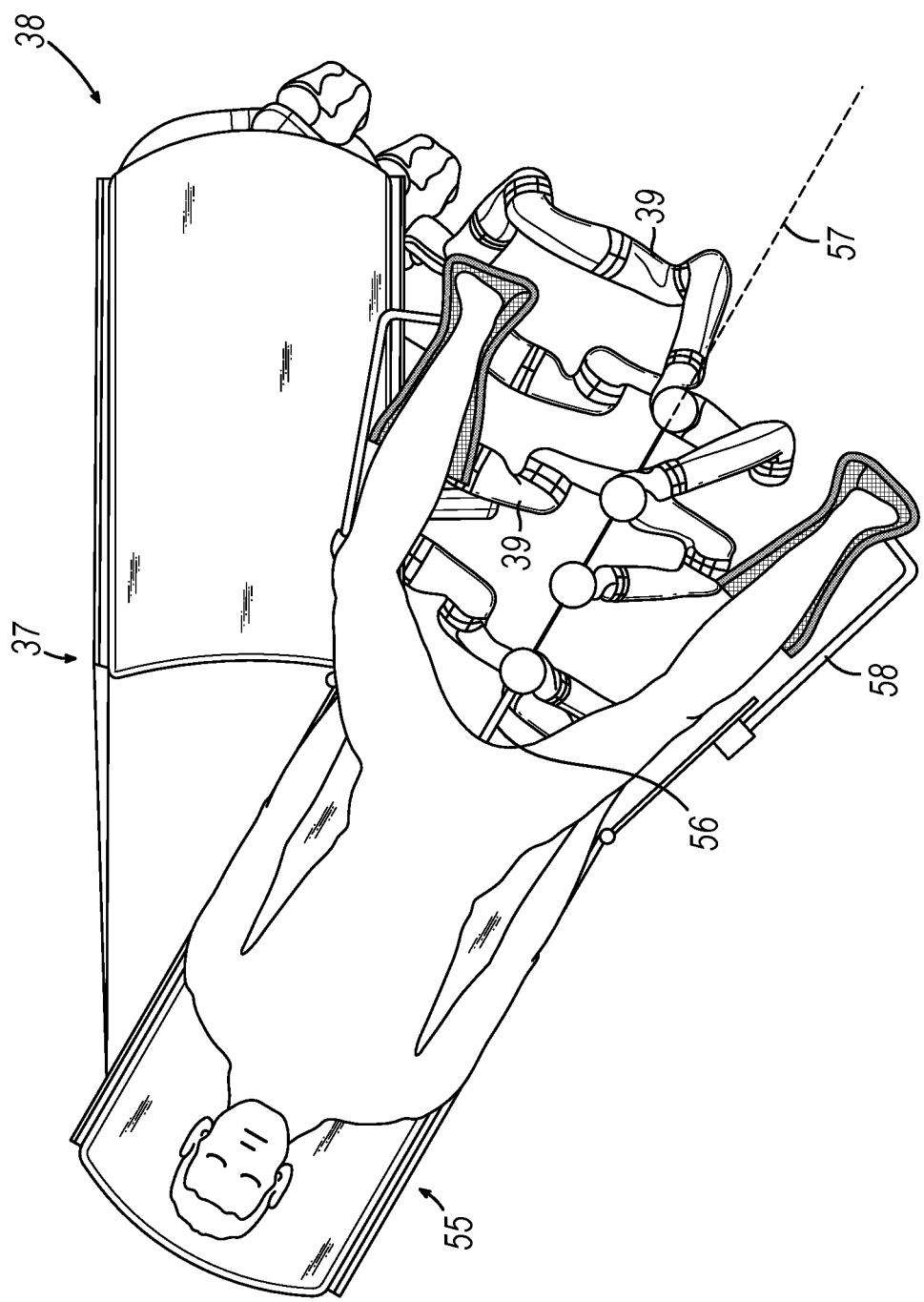
FIG. 8 depicts an embodiment of a table-based robotic system configured for a ureteroscopy procedure.

FIG. 8 illustrates an embodiment of a robotically-enabled table-based system configured for a ureteroscopy procedure. In a ureteroscopy, the table (38) may include a swivel portion (55) for positioning a patient off-angle from the column (37) and table base (46). The swivel portion (55) may rotate or pivot around a pivot point (e.g., located below the patient's head) in order to position the bottom portion of the swivel portion (55) away from the column (37). For example, the pivoting of the swivel portion (55) allows a C-arm (not shown) to be positioned over the patient's lower abdomen without competing for space with the column (not shown) below table (38). By rotating the carriage (35) (not shown) around the column (37), the robotic arms (39) may directly insert a ureteroscope (56) along a virtual rail (57) into the patient's groin area to reach the urethra. In a ureteroscopy, stirrups (58) may also be fixed to the swivel portion (55) of the table (38) to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages (43) of the system (36) may be rotated and vertically adjusted to position pairs of the robotic arms (39) on opposite sides of the table (38), such that instrument (59) may be positioned using the arm mounts (45) to be passed through minimal incisions on both sides of the patient to reach his/her abdominal cavity.

Figure 10:
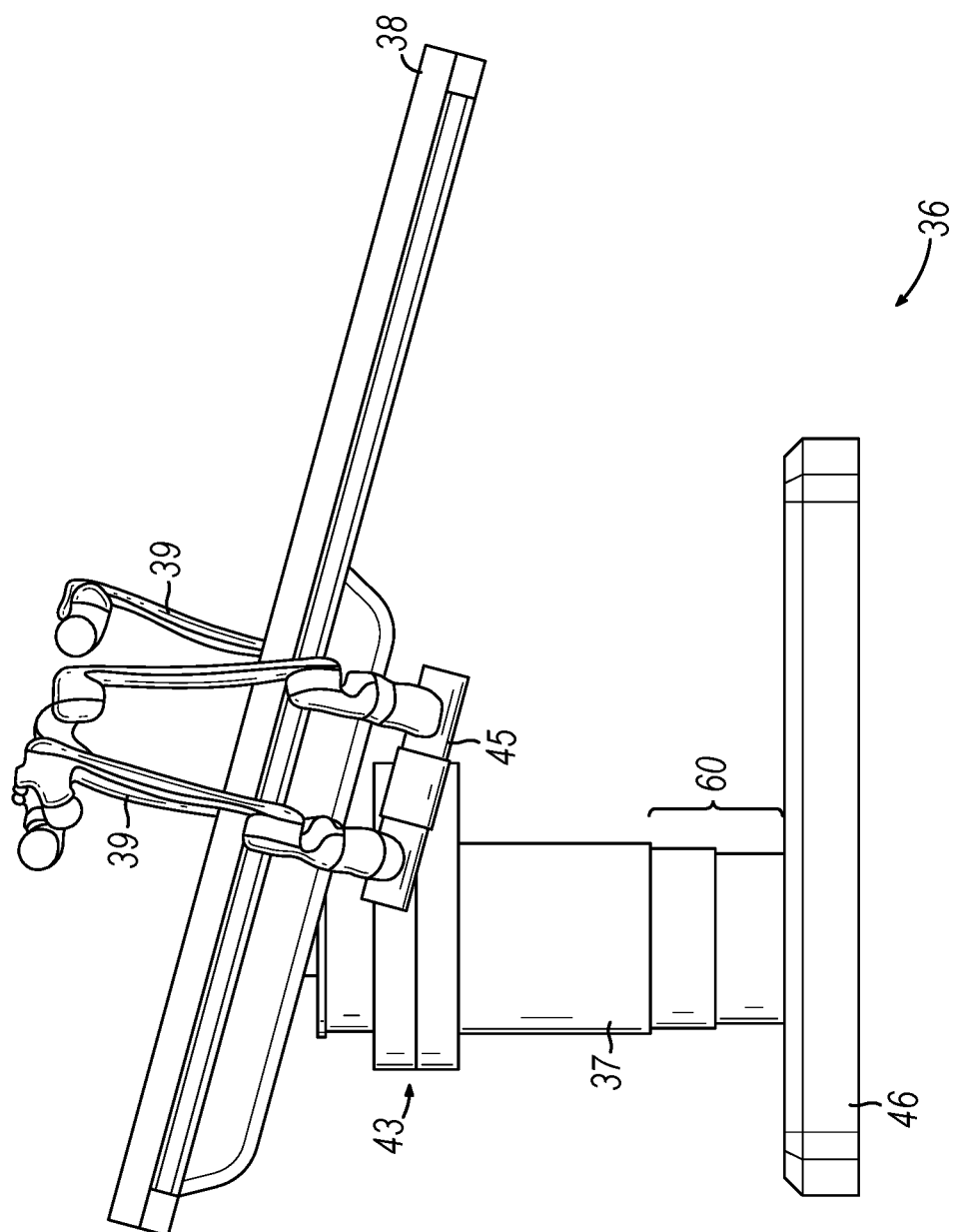
FIG. 10 depicts an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system (36) may accommodate tilt of the table (38) to position one portion of the table at a greater distance from the floor than the other. Additionally, the arm mounts (45) may rotate to match the tilt such that the arms (39) maintain the same planar relationship with table (38). To accommodate steeper angles, the column (37) may also include telescoping portions (60) that allow vertical extension of column (37) to keep the table (38) from touching the floor or colliding with base (46).

Figure 11:
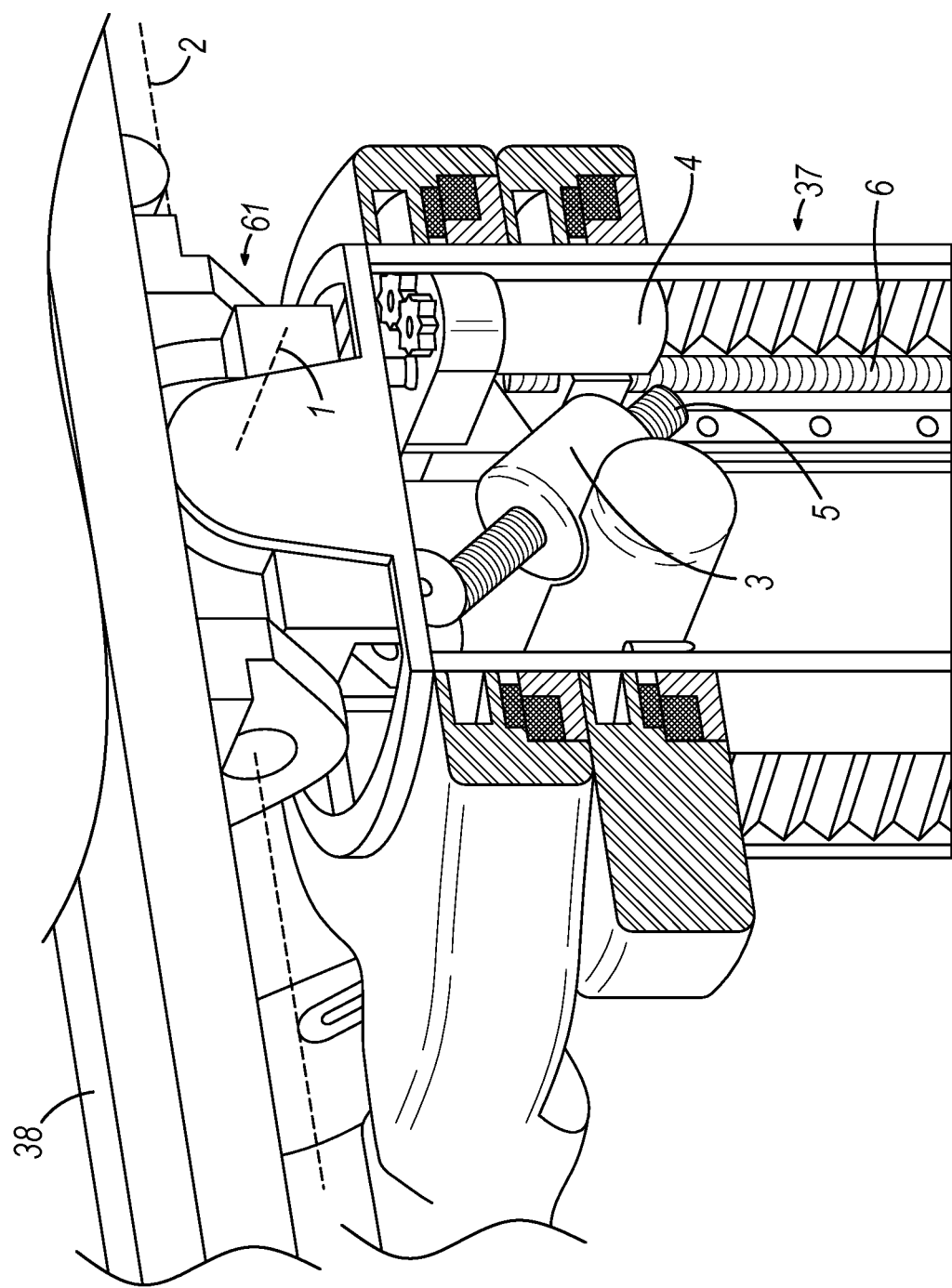
FIG. 11 provides a detailed illustration of the interface between the table and the column of the table-based robotic system of FIGS. 5-10.

FIG. 11 provides a detailed illustration of the interface between the table (38) and the column (37). Pitch rotation mechanism (61) may be configured to alter the pitch angle of the table (38) relative to the column (37) in multiple degrees of freedom. The pitch rotation mechanism (61) may be enabled by the positioning of orthogonal axes (1, 2) at the column-table interface, each axis actuated by a separate motor (3, 4) responsive to an electrical pitch angle command. Rotation along one screw (5) would enable tilt adjustments in one axis (1), while rotation along the other screw (6) would enable tilt adjustments along the other axis (2). In some embodiments, a ball joint can be used to alter the pitch angle of the table (38) relative to the column (37) in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
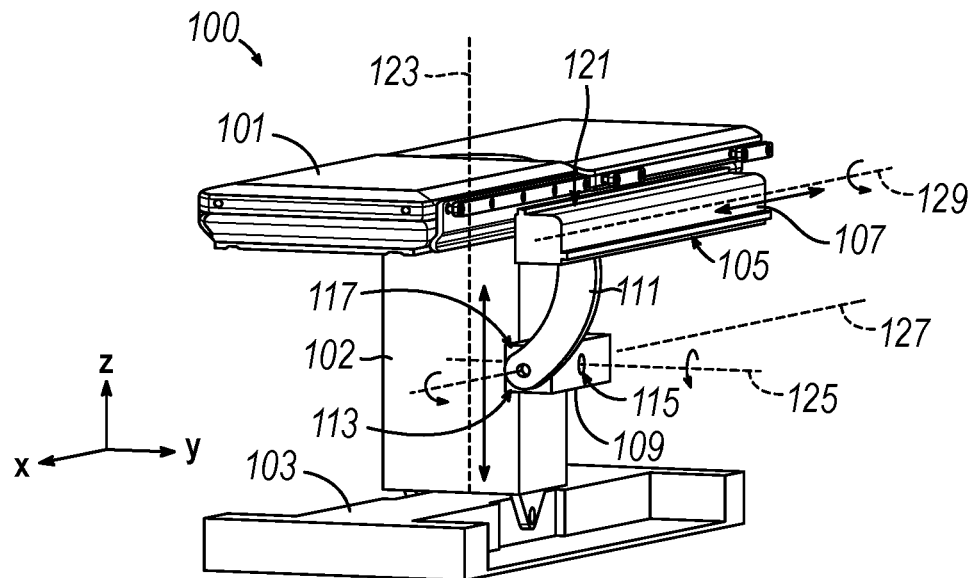
FIG. 12 depicts an alternative embodiment of a table-based robotic system.
Figure 13:
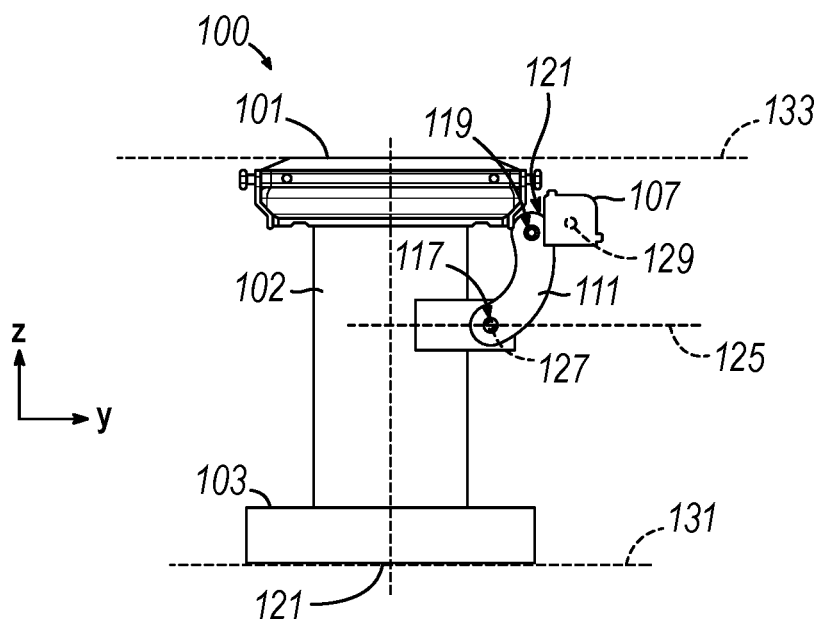
FIG. 13 depicts an end view of the table-based robotic system of FIG. 12.

FIGS. 12 and 13 illustrate isometric and end views of an alternative embodiment of a table-based surgical robotics system (100). The surgical robotics system (100) includes one or more adjustable arm supports (105) that can be configured to support one or more robotic arms (see, for example, FIG. 14) relative to a table (101). In the illustrated embodiment, a single adjustable arm support (105) is shown, though an additional arm support can be provided on an opposite side of the table (101). The adjustable arm support (105) can be configured so that it can move relative to the table (101) to adjust and/or vary the position of the adjustable arm support (105) and/or any robotic arms mounted thereto relative to the table (101). For example, the adjustable arm support (105) may be adjusted one or more degrees of freedom relative to the table (101). The adjustable arm support (105) provides high versatility to the system (100), including the ability to easily stow the one or more adjustable arm supports (105) and any robotics arms attached thereto beneath the table (101). The adjustable arm support (105) can be elevated from the stowed position to a position below an upper surface of the table (101). In other embodiments, the adjustable arm support (105) can be elevated from the stowed position to a position above an upper surface of the table (101).

The adjustable arm support (105) can provide several degrees of freedom, including lift, lateral translation, tilt, etc. In the illustrated embodiment of FIGS. 12 and 13, the arm support (105) is configured with four degrees of freedom, which are illustrated with arrows in FIG. 12. A first degree of freedom allows for adjustment of the adjustable arm support (105) in the z-direction ("Z-lift"). For example, the adjustable arm support (105) can include a carriage (109) configured to move up or down along or relative to a column (102) supporting the table (101). A second degree of freedom can allow the adjustable arm support (105) to tilt. For example, the adjustable arm support (105) can include a rotary joint, which can allow the adjustable arm support (105) to be aligned with the bed in a Trendelenburg position. A third degree of freedom can allow the adjustable arm support (105) to "pivot up," which can be used to adjust a distance between a side of the table (101) and the adjustable arm support (105). A fourth degree of freedom can permit translation of the adjustable arm support (105) along a longitudinal length of the table.

The surgical robotics system (100) in FIGS. 12 and 13 can comprise a table supported by a column (102) that is mounted to a base (103). The base (103) and the column (102) support the table (101) relative to a support surface. A floor axis (131) and a support axis (133) are shown in FIG. 13.

The adjustable arm support (105) can be mounted to the column (102). In other embodiments, the arm support (105) can be mounted to the table (101) or base (103). The adjustable arm support (105) can include a carriage (109), a bar or rail connector (111) and a bar or rail (107). In some embodiments, one or more robotic arms mounted to the rail (107) can translate and move relative to one another.

The carriage (109) can be attached to the column (102) by a first joint (113), which allows the carriage (109) to move relative to the column (102) (e.g., such as up and down a first or vertical axis 123). The first joint (113) can provide the first degree of freedom ("Z-lift") to the adjustable arm support (105). The adjustable arm support (105) can include a second joint 115, which provides the second degree of freedom (tilt) for the adjustable arm support (105). The adjustable arm support (105) can include a third joint (117), which can provide the third degree of freedom ("pivot up") for the adjustable arm support (105). An additional joint (119) (shown in FIG. 13) can be provided that mechanically constrains the third joint (117) to maintain an orientation of the rail (107) as the rail connector (111) is rotated about a third axis (127). The adjustable arm support (105) can include a fourth joint (121), which can provide a fourth degree of freedom (translation) for the adjustable arm support (105) along a fourth axis (129).

Figure 14:
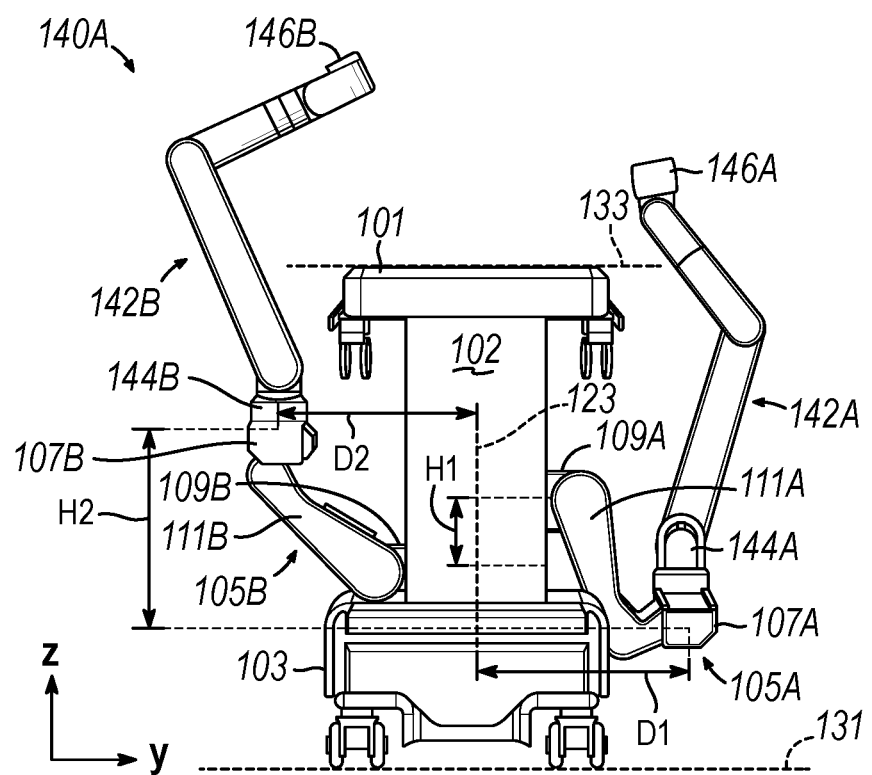
FIG. 14 depicts an end view of a table-based robotic system with robotic arms attached thereto.

FIG. 14 illustrates an end view of the surgical robotics system (140A) with two adjustable arm supports (105A, 105B) mounted on opposite sides of a table (101). A first robotic arm (142A) is attached to the bar or rail (107A) of the first adjustable arm support (105B). The first robotic arm (142A) includes a base (144A) attached to the rail (107A). The distal end of the first robotic arm (142A) includes an instrument drive mechanism (146A) that can attach to one or more robotic medical instruments or tools. Similarly, the second robotic arm (142B) includes a base (144B) attached to the rail (107B). The distal end of the second robotic arm (142B) includes an instrument drive mechanism (146B). The instrument drive mechanism (146B) can be configured to attach to one or more robotic medical instruments or tools.

In some embodiments, one or more of the robotic arms (142A, 142B) comprises an arm with seven or more degrees of freedom. In some embodiments, one or more of the robotic arms (142A, 142B) can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base (144A, 144B) (1-degree of freedom including translation). In some embodiments, the insertion degree of freedom can be provided by the robotic arm (142A, 142B), while in other embodiments, the instrument itself provides insertion via an instrument-based insertion architecture.

C. Example of Robotic System Instrument Driver & Interface

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
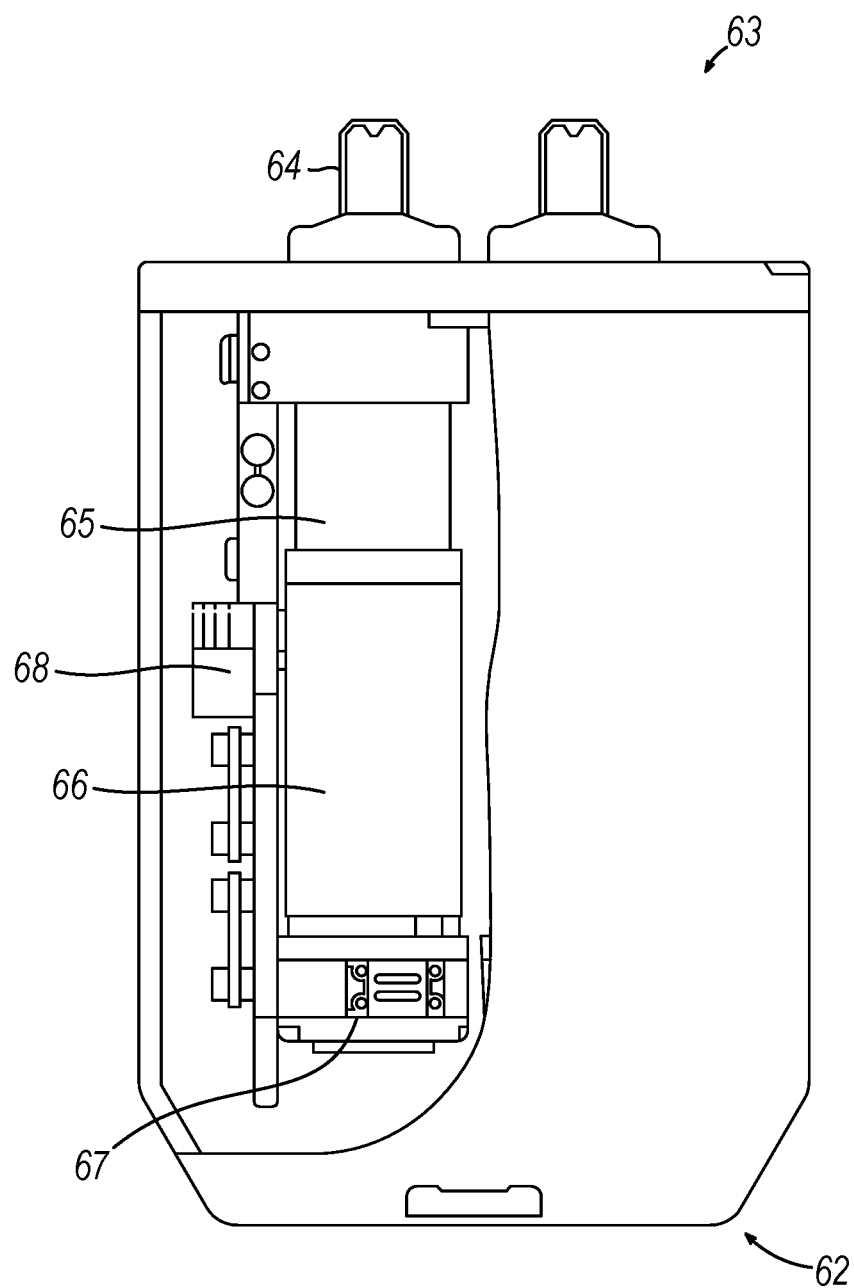
FIG. 15 depicts an exemplary instrument driver.

FIG. 15 illustrates an example instrument driver. Positioned at the distal end of a robotic arm, instrument driver (62) comprises of one or more drive units (63) arranged with parallel axes to provide controlled torque to a medical instrument via drive shafts (64). Each drive unit (63) comprises an individual drive shaft (64) for interacting with the instrument, a gear head (65) for converting the motor shaft rotation to a desired torque, a motor (66) for generating the drive torque, an encoder (67) to measure the speed of the motor shaft and provide feedback to the control circuitry, and control circuitry (68) for receiving control signals and actuating the drive unit. Each drive unit (63) being independent controlled and motorized, the instrument driver (62) may provide multiple (four as shown in FIG. 15) independent drive outputs to the medical instrument. In operation, the control circuitry (68) would receive a control signal, transmit a motor signal to the motor (66), compare the resulting motor speed as measured by the encoder (67) with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Example of Robotic System Medical Instrument

Figure 16:
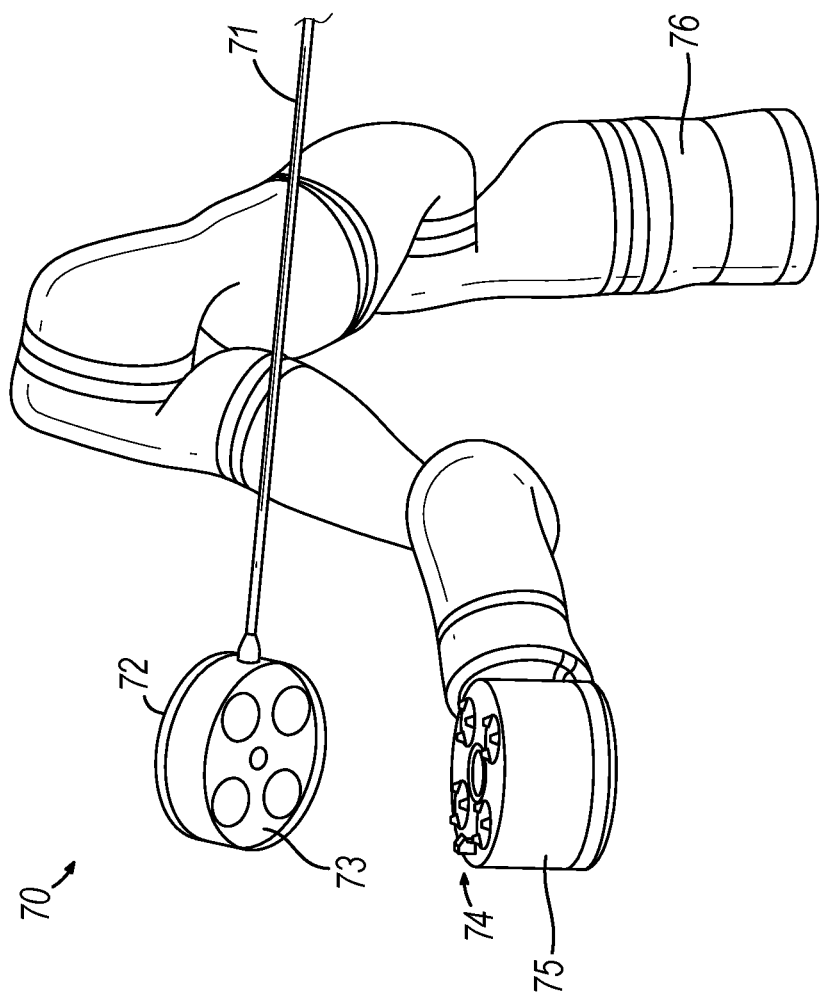
FIG. 16 depicts an exemplary medical instrument with a paired instrument driver.

FIG. 16 illustrates an example medical instrument with a paired instrument driver. Like other instruments designed for use with a robotic system, medical instrument (70) comprises an elongated shaft (71) (or elongate body) and an instrument base (72). The instrument base (72), also referred to as an "instrument handle" due to its intended design for manual interaction by the physician, may generally comprise rotatable drive inputs (73), e.g., receptacles, pulleys or spools, that are designed to be mated with drive outputs (74) that extend through a drive interface on instrument driver (75) at the distal end of robotic arm (76). When physically connected, latched, and/or coupled, the mated drive inputs (73) of instrument base (72) may share axes of rotation with the drive outputs (74) in the instrument driver (75) to allow the transfer of torque from drive outputs (74) to drive inputs (73). In some embodiments, the drive outputs (74) may comprise splines that are designed to mate with receptacles on the drive inputs (73).

The elongated shaft (71) is designed to be delivered through either an anatomical opening or lumen, e.g., as in endoscopy, or a minimally invasive incision, e.g., as in laparoscopy. The elongated shaft (71) may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs (74) of the instrument driver (75). When designed for endoscopy, the distal end of a flexible elongated shaft may include a steerable or controllable bending section that may be articulated and bent based on torque received from the drive outputs (74) of the instrument driver (75).

Torque from the instrument driver (75) is transmitted down the elongated shaft (71) using tendons along the shaft (71). These individual tendons, such as pull wires, may be individually anchored to individual drive inputs (73) within the instrument handle (72). From the handle (72), the tendons are directed down one or more pull lumens along the elongated shaft (71) and anchored at the distal portion of the elongated shaft (71), or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs (73) would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft (71), where tension from the tendon cause the grasper to close.

In endoscopy, the tendons may be coupled to a bending or articulating section positioned along the elongated shaft (71) (e.g., at the distal end) via adhesive, control ring, or other mechanical fixation. When fixedly attached to the distal end of a bending section, torque exerted on drive inputs (73) would be transmitted down the tendons, causing the softer, bending section (sometimes referred to as the articulatable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft (71) to allow for controlled articulation in the desired bending or articulatable sections.

In endoscopy, the elongated shaft (71) houses a number of components to assist with the robotic procedure. The shaft may comprise of a working channel for deploying surgical tools (or medical instruments), irrigation, and/or aspiration to the operative region at the distal end of the shaft (71). The shaft (71) may also accommodate wires and/or optical fibers to transfer signals to/from an optical assembly at the distal tip, which may include of an optical camera. The shaft (71) may also accommodate optical fibers to carry light from proximally-located light sources, such as light emitting diodes, to the distal end of the shaft.

At the distal end of the instrument (70), the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft (71). Rolling the elongated shaft (71) along its axis while keeping the drive inputs (73) static results in undesirable tangling of the tendons as they extend off the drive inputs (73) and enter pull lumens within the elongated shaft (71). The resulting entanglement of such tendons may disrupt any control algorithms intended to predict movement of the flexible elongated shaft during an endoscopic procedure.

Figure 17:
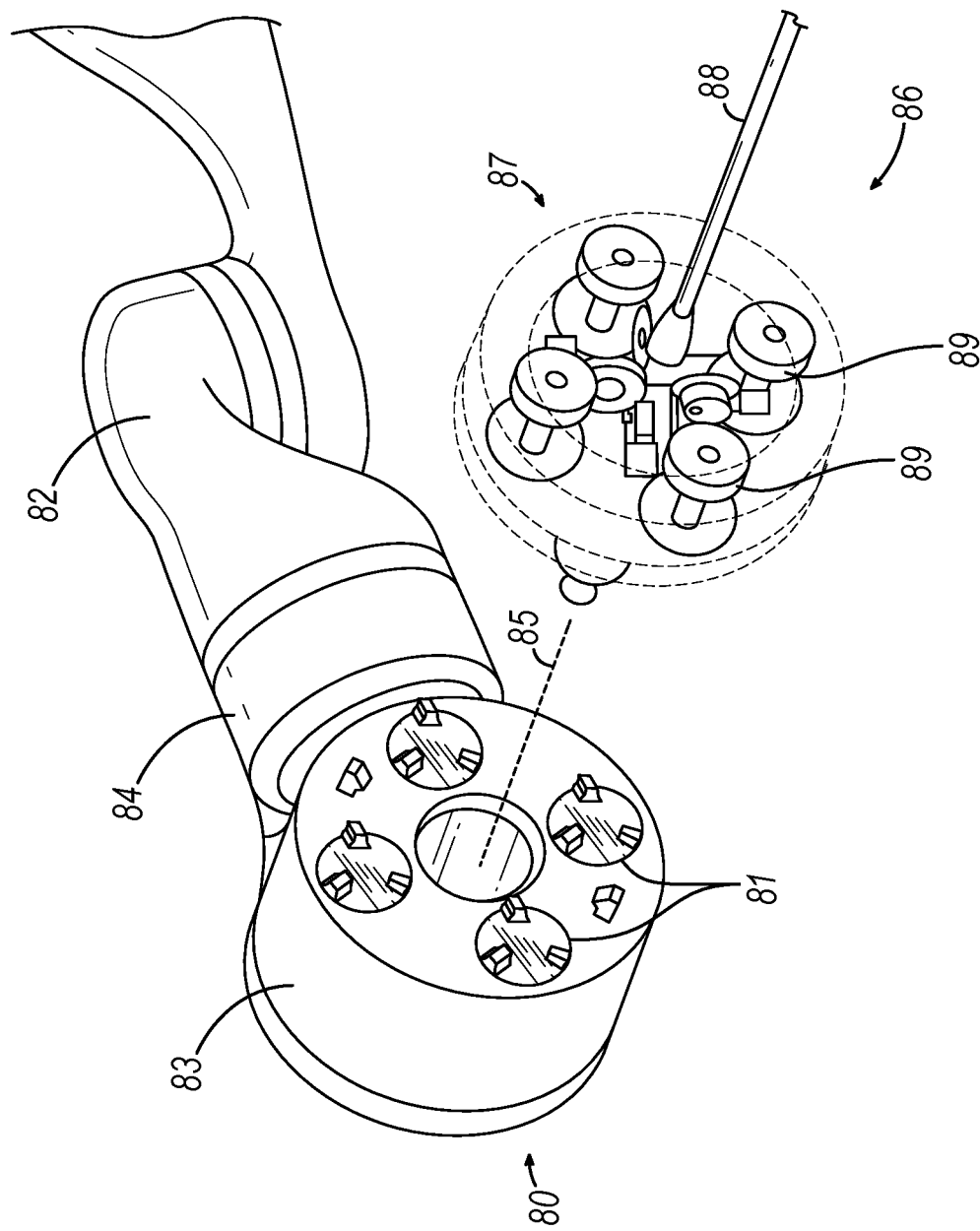
FIG. 17 depicts an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver (80) comprises four drive units with their drive outputs (81) aligned in parallel at the end of a robotic arm (82). The drive units, and their respective drive outputs (81), are housed in a rotational assembly (83) of the instrument driver (80) that is driven by one of the drive units within the assembly (83). In response to torque provided by the rotational drive unit, the rotational assembly (83) rotates along a circular bearing that connects the rotational assembly (83) to the non-rotational portion (84) of the instrument driver. Power and controls signals may be communicated from the non-rotational portion (84) of the instrument driver (80) to the rotational assembly (83) through electrical contacts may be maintained through rotation by a brushed slip ring connection (not shown). In other embodiments, the rotational assembly (83) may be responsive to a separate drive unit that is integrated into the non-rotatable portion (84), and thus not in parallel to the other drive units. The rotational assembly (83) allows the instrument driver (80) to rotate the drive units, and their respective drive outputs (81), as a single unit around an instrument driver axis (85).

Like earlier disclosed embodiments, an instrument 86 may comprise an elongated shaft portion (88) and an instrument base (87) (shown with a transparent external skin for discussion purposes) comprising a plurality of drive inputs (89) (such as receptacles, pulleys, and spools) that are configured to receive the drive outputs (81) in the instrument driver (80). Unlike prior disclosed embodiments, instrument shaft (88) extends from the center of instrument base (87) with an axis substantially parallel to the axes of the drive inputs (89), rather than orthogonal as in the design of FIG. 16.

When coupled to the rotational assembly (83) of the instrument driver (80), the medical instrument 86, comprising instrument base (87) and instrument shaft (88), rotates in combination with the rotational assembly (83) about the instrument driver axis (85). Since the instrument shaft (88) is positioned at the center of instrument base (87), the instrument shaft (88) is coaxial with instrument driver axis (85) when attached. Thus, rotation of the rotational assembly (83) causes the instrument shaft (88) to rotate about its own longitudinal axis. Moreover, as the instrument base (87) rotates with the instrument shaft (88), any tendons connected to the drive inputs (89) in the instrument base (87) are not tangled during rotation. Accordingly, the parallelism of the axes of the drive outputs (81), drive inputs (89), and instrument shaft (88) allows for the shaft rotation without tangling any control tendons.

Figure 18:
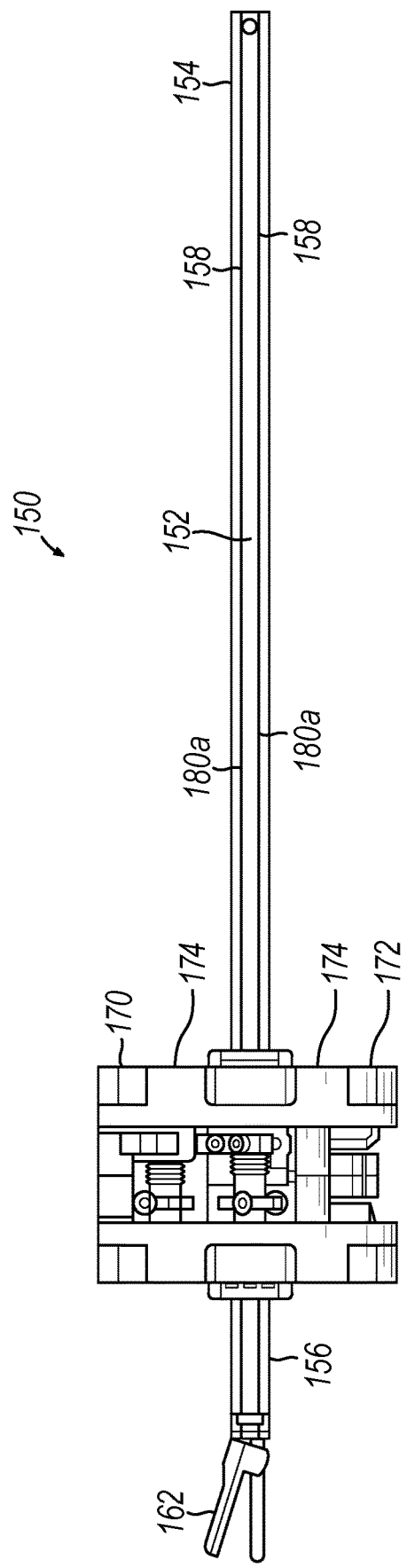
FIG. 18 depicts an instrument having an instrument-based insertion architecture.

FIG. 18 illustrates an instrument having an instrument based insertion architecture in accordance with some embodiments. The instrument (150) can be coupled to any of the instrument drivers discussed above. The instrument (150) comprises an elongated shaft (152), an end effector (162) connected to the shaft (152), and a handle (170) coupled to the shaft (152). The elongated shaft (152) comprises a tubular member having a proximal portion (154) and a distal portion (156). The elongated shaft (152) comprises one or more channels or grooves (158) along its outer surface. The grooves (158) are configured to receive one or more wires or cables (180) therethrough. One or more cables (180) thus run along an outer surface of the elongated shaft (152). In other embodiments, cables (180) can also run through the elongated shaft (152). Manipulation of the one or more cables (180) (e.g., via an instrument driver) results in actuation of the end effector (162).

The instrument handle (170), which may also be referred to as an instrument base, may generally comprise an attachment interface (172) having one or more mechanical inputs (174), e.g., receptacles, pulleys or spools, that are designed to be reciprocally mated with one or more torque couplers on an attachment surface of an instrument driver.

In some embodiments, the instrument (150) comprises a series of pulleys or cables that enable the elongated shaft (152) to translate relative to the handle (170). In other words, the instrument (150) itself comprises an instrument-based insertion architecture that accommodates insertion of the instrument, thereby minimizing the reliance on a robot arm to provide insertion of the instrument (150). In other embodiments, a robotic arm can be largely responsible for instrument insertion.

E. Example of Robotic System Controller

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
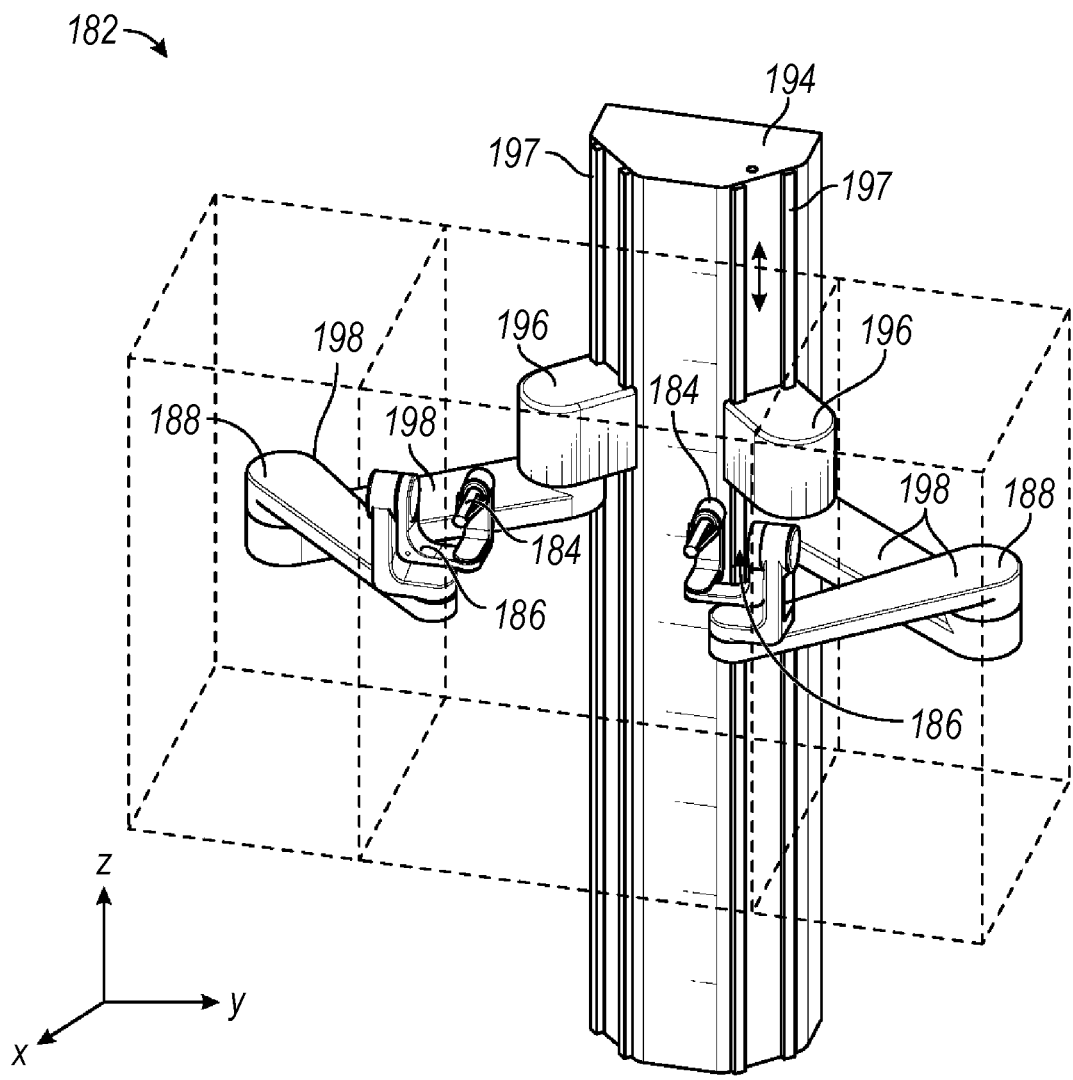
FIG. 19 depicts an exemplary controller.

FIG. 19 is a perspective view of an embodiment of a controller (182). In the present embodiment, the controller (182) comprises a hybrid controller that can have both impedance and admittance control. In other embodiments, the controller (182) can utilize just impedance or passive control. In other embodiments, the controller (182) can utilize just admittance control. By being a hybrid controller, the controller (182) advantageously can have a lower perceived inertia while in use.

In the illustrated embodiment, the controller (182) is configured to allow manipulation of two medical instruments, and includes two handles (184). Each of the handles (184) is connected to a gimbal (186). Each gimbal (186) is connected to a positioning platform (188).

As shown in FIG. 19, each positioning platform (188) includes a SCARA arm (selective compliance assembly robot arm) (198) coupled to a column (194) by a prismatic joint (196). The prismatic joints (196) are configured to translate along the column (194) (e.g., along rails (197)) to allow each of the handles (184) to be translated in the z-direction, providing a first degree of freedom. The SCARA arm (198) is configured to allow motion of the handle (184) in an x-y plane, providing two additional degrees of freedom.

In some embodiments, one or more load cells are positioned in the controller. For example, in some embodiments, a load cell (not shown) is positioned in the body of each of the gimbals (186). By providing a load cell, portions of the controller (182) are capable of operating under admittance control, thereby advantageously reducing the perceived inertia of the controller while in use. In some embodiments, the positioning platform (188) is configured for admittance control, while the gimbal (186) is configured for impedance control. In other embodiments, the gimbal (186) is configured for admittance control, while the positioning platform (188) is configured for impedance control. Accordingly, for some embodiments, the translational or positional degrees of freedom of the positioning platform (188) can rely on admittance control, while the rotational degrees of freedom of the gimbal (186) rely on impedance control.

F. Example of Robotic System Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
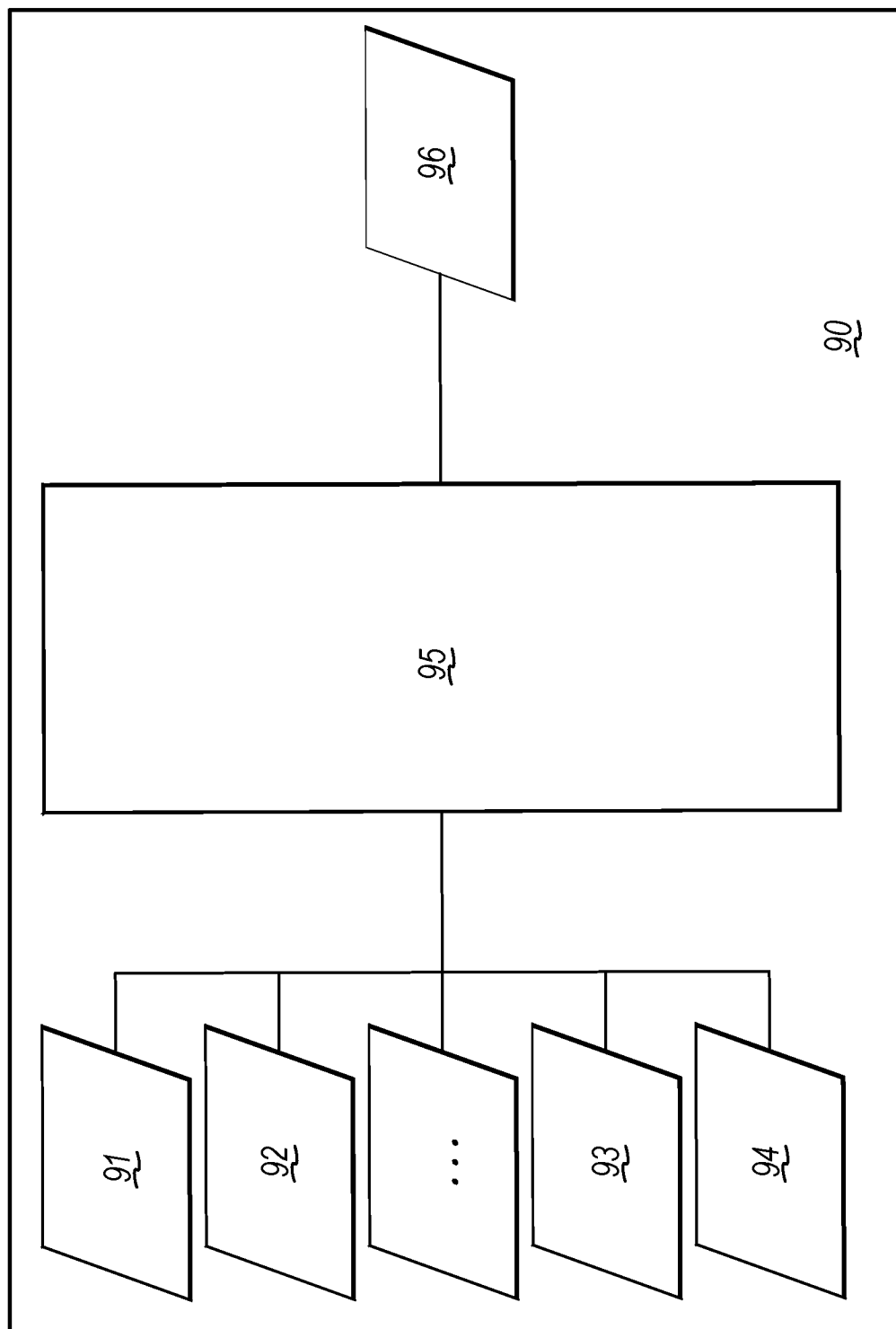
FIG. 20 depicts a block diagram illustrating a localization system that estimates a location of one or more elements of the robotic systems of FIGS. 1-10, such as the location of the instrument of FIGS. 16-18, in accordance with an example embodiment.

FIG. 20 is a block diagram illustrating a localization system (90) that estimates a location of one or more elements of the robotic system, such as the location of the instrument, in accordance to an example embodiment. The localization system (90) may be a set of one or more computer devices configured to execute one or more instructions. The computer devices may be embodied by a processor (or processors) and computer-readable memory in one or more components discussed above. By way of example and not limitation, the computer devices may be in the tower (30) shown in FIG. 1, the cart shown in FIGS. 1-4, the beds shown in FIGS. 5-14, etc.

As shown in FIG. 20, the localization system (90) may include a localization module (95) that processes input data (91-94) to generate location data (96) for the distal tip of a medical instrument. The location data (96) may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data (91-94) are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data (91) (also referred to as "preoperative model data" when generated using only preoperative CT scans). The use of center-line geometry is discussed in U.S. Pat. No. 9,763,741, the contents of which are herein incorporated in its entirety. Network topological models may also be derived from the CT-images, and are particularly appropriate for bronchoscopy.

In some embodiments, the instrument may be equipped with a camera to provide vision data (92). The localization module (95) may process the vision data to enable one or more vision-based location tracking. For example, the preoperative model data may be used in conjunction with the vision data (92) to enable computer vision-based tracking of the medical instrument (e.g., an endoscope or an instrument advance through a working channel of the endoscope). For example, using the preoperative model data (91), the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module (95) may identify circular geometries in the preoperative model data (91) that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data (92) to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module (95) may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location.

The location information detected by the EM sensors is stored as EM data (93). The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data (94) may also be used by the localization module (95) to provide localization data (96) for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module (95). For example, although not shown in FIG. 20, an instrument utilizing shape-sensing fiber can provide shape data that the localization module (95) can use to determine the location and shape of the instrument.

The localization module (95) may use the input data (91-94) in combination(s). In some cases, such a combination may use a probabilistic approach where the localization module (95) assigns a confidence weight to the location determined from each of the input data (91-94). Thus, where the EM data may not be reliable (as may be the case where there is EM interference) the confidence of the location determined by the EM data (93) can be decrease and the localization module (95) may rely more heavily on the vision data (92) and/or the robotic command and kinematics data (94).

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

II. Example of Robotically Controlled Uterine Manipulator

In some conventional hysterectomy procedures, a first clinician may serve in a role of forming incisions and performing other laparoscopic operations to remove the uterus of a patient, while a second clinician may serve in a role of manipulating the position and orientation of the uterus of the patient to facilitate the operations being performed by the first clinician. Such team-based procedures may require clear communication between the first clinician and the second clinician, with the first clinician instructing the second clinician on desired positioning and orientation of the uterus, and with the second clinician responding in a timely and accurate fashion. In some scenarios, such communications may break down or otherwise yield undesirable results, such as the second clinician not precisely positioning or orienting the uterus when and where the first clinician wishes. It may therefore be desirable to provide a robotic system that is capable of performing at least part of the role of the second clinician, such that the robotic system may at least partially control the position and orientation of the uterus based on the desire of the first clinician. Examples of how a robotic system may provide uterine manipulation are described in greater detail below. The following examples may be readily incorporated into any of the various robotic systems (10, 36, 47, 100, 140A) described herein; or in any other suitable robotic system.

Figure 21:
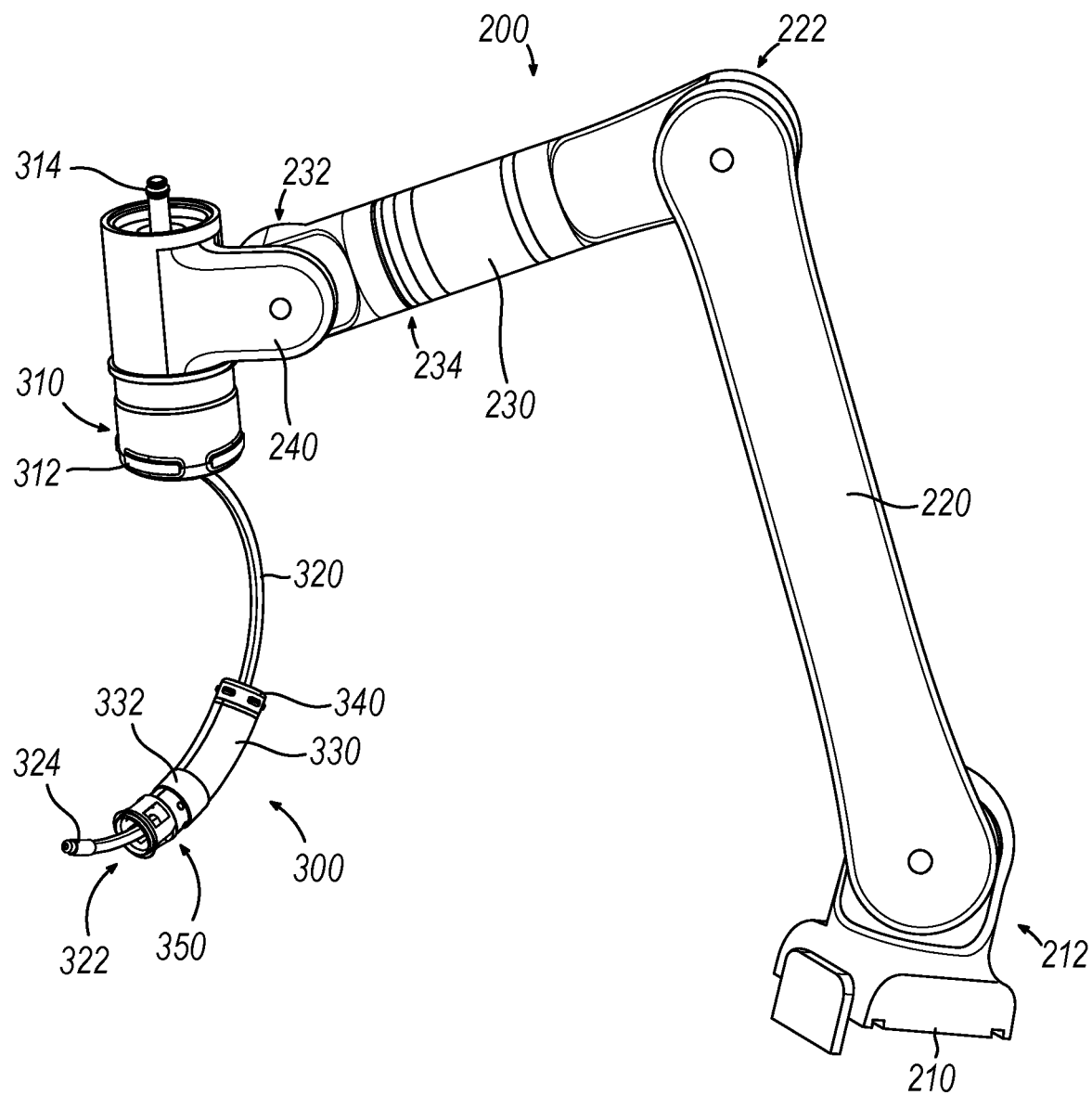
FIG. 21 depicts a perspective view of an example of a robotic arm with a uterine manipulator instrument.

FIG. 21 shows an example of a uterine manipulator (300) secured to a robotic arm (200). Robotic arm (200) of this example includes a mount (210), arm segments (220, 230), a plurality of joints (212, 222, 234, 232), and a head (240). Mount (210) is configured to couple with a component of a robotic system (10, 36, 47, 100, 140A) for support. For instance, mount (210) may be coupled with carriage interface (19), carriage (43), rail (197), or any other suitable structure. In some versions, base (210) is operable to translate along the structure to which base (210) is secured, to thereby assist in positioning robotic arm (200) in relation to a patient and/or to otherwise position robotic arm (200). One end of arm segment (220) is pivotably coupled to base (210) via joint (212), such that arm segment (220) is pivotable relative to base (210) at joint (212). The other end of arm segment (220) is pivotably coupled to an end of arm segment (230) via joint (222), such that arm segment (230) is pivotable relative to arm segment (220) at joint (222). The other end of arm segment (230) is coupled with joint (232) via joint (234). Joint (234) is configured to allow joint (232) and head (240) to rotate relative to arm segment (230) about the longitudinal axis of arm segment (230). In some variations, a similar kind of joint is provided in arm segment (220), such that arm segment (220) may be effectively broken into two segments where one of those segments is rotatable relative to the other about the longitudinal axes of those two segments. Head (240) is pivotably coupled with joint (234) via joint (232), such that head (240) is pivotable relative to joint (234) at joint (232). Motion at any of joints (212, 222, 234, 232) may be driven robotically via motors, solenoids, and/or any other suitable source(s) of motion.

Figure 22:
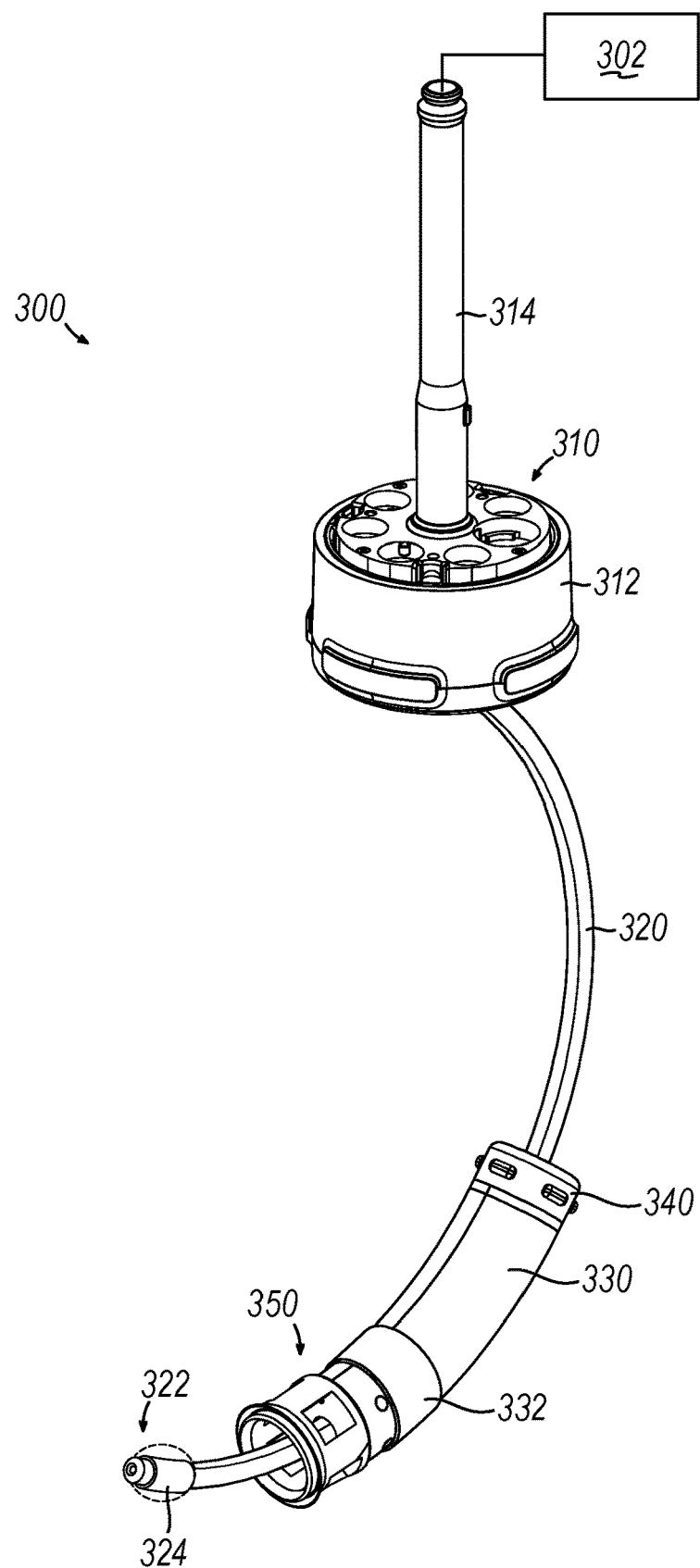
FIG. 22 depicts a perspective view of the uterine manipulator instrument of FIG. 21.

Uterine manipulator (300) is removably coupled with head (240), such that robotic arm (200) may selectively position and orient uterine manipulator in relation to a patient by driving robotic arm (200). As best seen in FIG. 22, uterine manipulator (300) of the present example includes a head interface assembly (310), a shaft (320), a sleeve (330), a sleeve locking ring (340), and a colpotomy cup (350). Head interface assembly (310) includes a base (312) and a shaft (314). Base (312) is configured to removably couple with head (240) to thereby secure uterine manipulator (300) with head (240). By way of example only, base (312) and head (240) may include complementary bayonet fitting features, complementary threading, complementary snap-fit features, and/or any other suitable kinds of structures to provide a removable coupling. Shaft (320) is configured to couple with a pressurized fluid source (302). Pressurized fluid source (302) may contain pressurized air, pressurized saline, or any other suitable kind of pressurized fluid. The pressurized fluid may be used to selectively inflate balloons (324, 332), which will be described in greater detail below.

Shaft (320) of the present example extends distally from base (312) along a curve. In some versions, shaft (320) is rigid. In some other versions, shaft (320) is flexible yet resiliently biased to assume the curved configuration shown. Any suitable biocompatible material(s) may be used to form shaft (320), including but not limited to metallic materials, plastic materials, and combinations thereof. An inflatable balloon (324) is positioned near distal end (322) of shaft (320). Balloon (324) may be formed of an extensible material or a non-extensible material. The interior of shaft (320) includes one or more lumen(s) that are configured to communicate pressurized fluid from pressurized fluid source (302) to balloon (324). While balloon (324) is positioned near distal end (322) of shaft (320) in the present example, other versions may include a different kind of expandable member. By way of example only, an alternative expandable member may include a mechanically expandable component such as an expandable mesh structure, an expanding umbrella-like structure, or any other suitable kind of expandable structure or assembly. In some versions, distal end (322) of shaft (320) may also include an illuminating element (e.g., one or more LEDs, a lens illuminated by one or more optical fibers, etc.). In such versions, one or more wires, optical fibers, and/or other components may extend along the length of shaft (320) to couple with a source of electrical power, a source of light, etc.

Sleeve (330) is slidably coupled to shaft (320), such that sleeve (330) may slide along shaft (320) from a proximal position (FIGS. 25B-25C) to any number of distal positions (FIGS. 21, 22, 25D-25E). Sleeve (330) is generally cylindraceous and rigid; and extends along a curved axis such that the curved lateral profile complements the curved lateral profile of shaft (320). Sleeve (330) may be formed of plastic, metal, and/or any other suitable biocompatible material(s), including combinations of materials. Locking ring (340) is rotatably secured to the proximal end of sleeve (330), while colpotomy cup (350) is fixedly secured to the distal end of sleeve (330). An inflatable balloon (332) is positioned along sleeve (330), between locking ring (340) and colpotomy cup (350). Balloon (332) may be formed of an extensible material or a non-extensible material. The interior of sleeve (330) includes one or more lumen(s) that are configured to communicate pressurized fluid from pressurized fluid source (302) to balloon (332). Such a lumen or lumens may be coupled with pressurized fluid source (302) via a flexible tube (not shown). In some versions, one or more lumens or tubes within shaft (320) provide at least part of the fluid pathway between balloon (332) and pressurized fluid source (302).

Locking ring (340) is operable to selectively secure the position of sleeve (330) along the length of shaft (320). For instance, locking ring (340) may be rotated to a first angular position relative to sleeve (330) to provide an unlocked state where sleeve (330) may be freely translated along shaft (320). Locking ring (340) may then be rotated to a second angular position relative to sleeve (330) to provide a locked state where the position of sleeve (330) along shaft (320) is secured until locking ring (340) is rotated back to the first angular position. By way of example only, locking ring (340) may include one or more frictional braking structures that selectively engage shaft (320) to thereby provide the locked state. Alternatively, locking ring (340) may selectively engage shaft (320) in any other suitable fashion.

Figure 23:
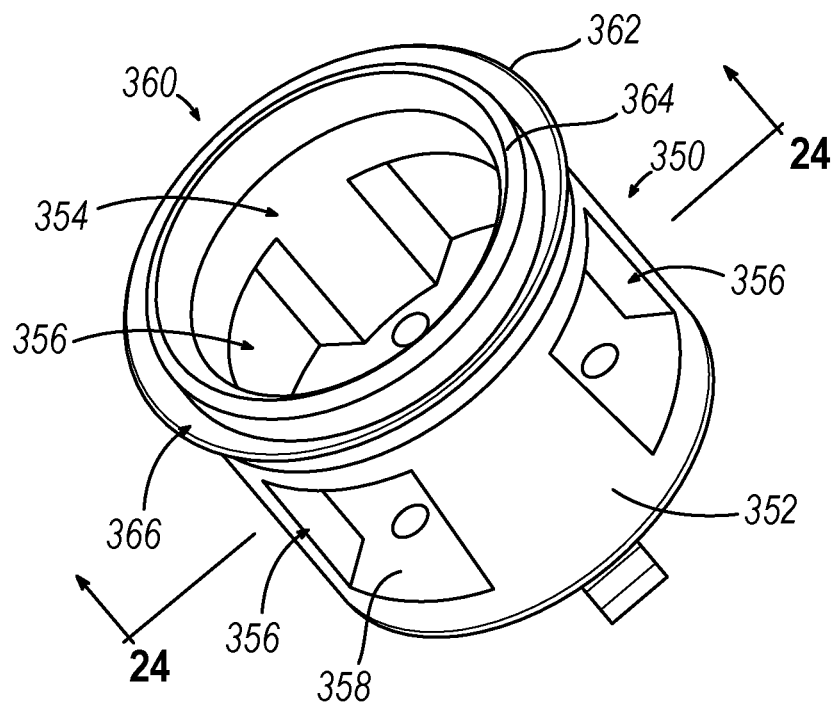
FIG. 23 depicts a perspective view of a colpotomy cup of the uterine manipulator instrument of FIG. 23.
Figure 24:
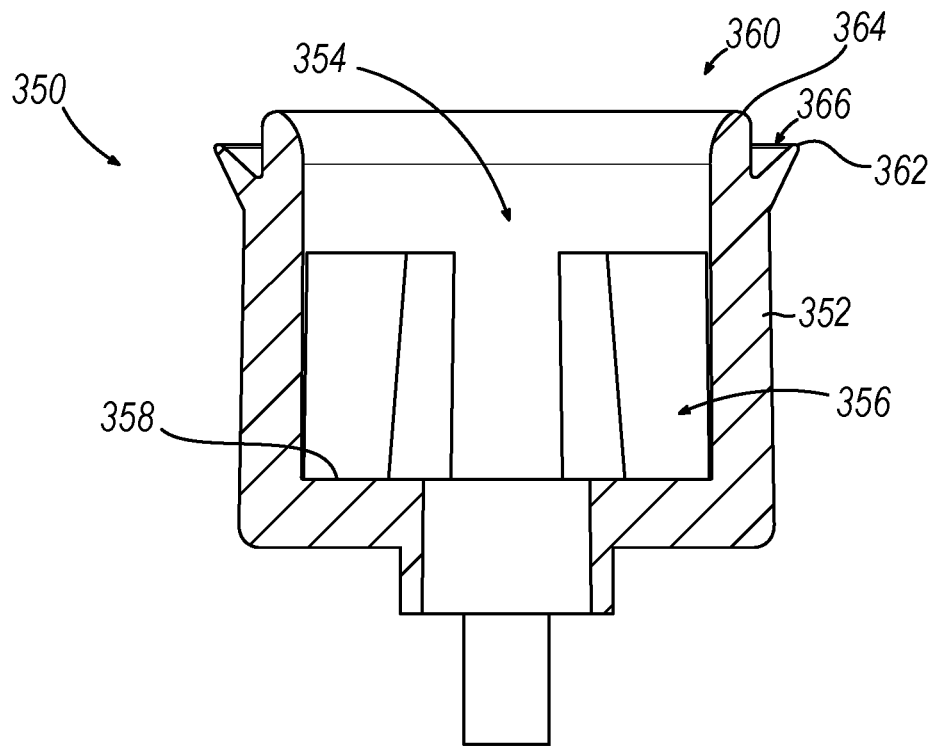
FIG. 24 depicts a cross-sectional side view of the colpotomy cup of FIG. 23, taken along section line 24-24 in FIG. 23.

FIGS. 23-24 show colpotomy cup (350) in greater detail. As shown, colpotomy cup (350) of the present example includes a body (352) defining an interior space (354). Body (352) further includes a floor (358) at the bottom of interior space (354) and an open distal end (360). A plurality of lateral openings (356) are in communication with interior space (354). Distal end (360) includes a distally presented annular edge (364) and an obliquely presented annular edge (362), with a space (366) being defined between edges (362, 364). Space (366) has a V-shaped cross-sectional profile, as best seen in FIG. 24. Colpotomy cup (350) may be formed of plastic, metal, and/or any other suitable biocompatible material(s), including combinations of materials.

Figure 25A:
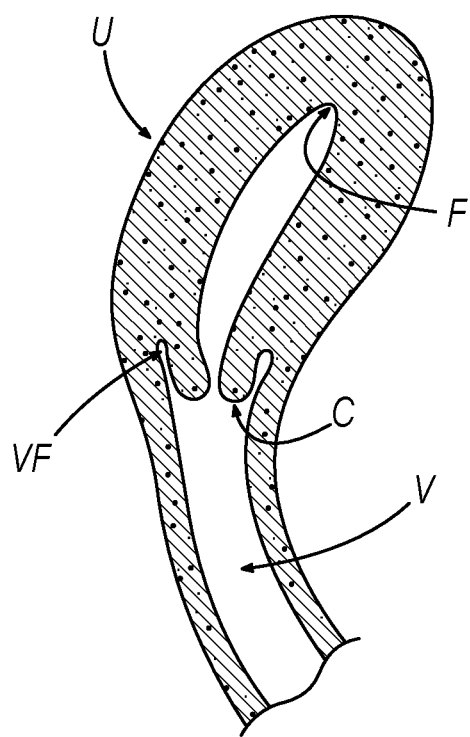
FIG. 25A depicts a mid-sagittal cross-sectional view of a vagina and uterus.
Figure 25B:
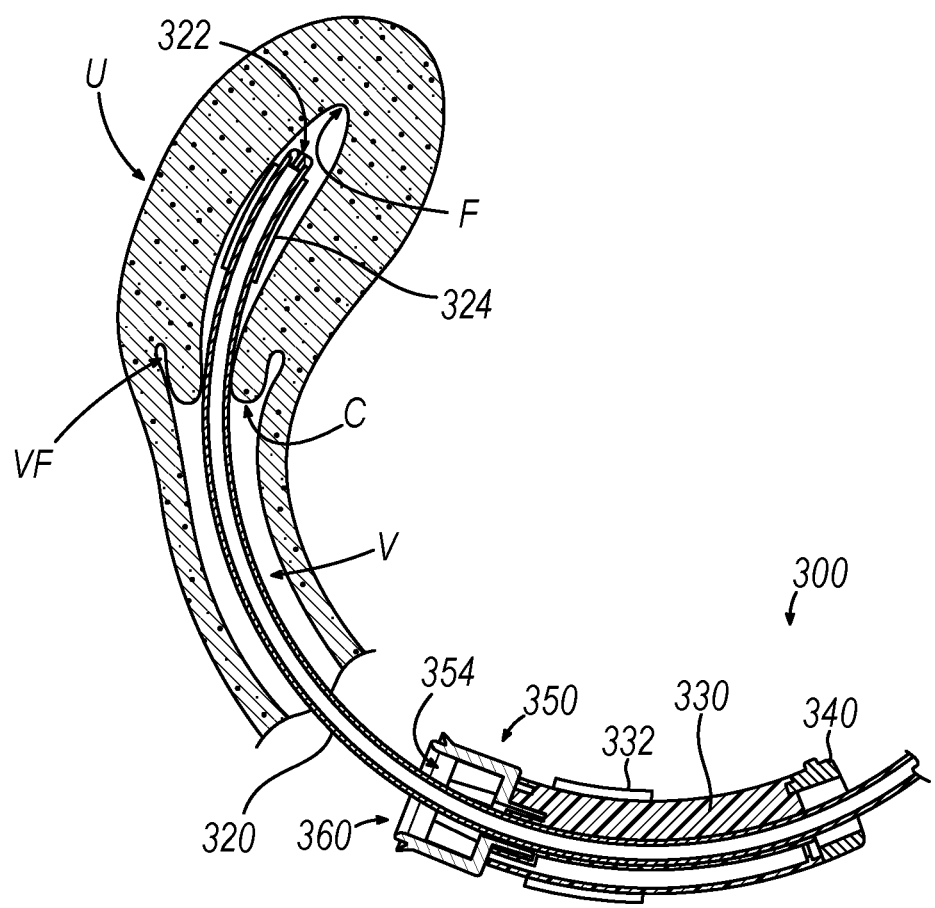
FIG. 25B depicts a mid-sagittal cross-sectional view of the vagina and uterus of FIG. 25A, with the shaft of the uterine manipulator instrument of FIG. 21 inserted through the vagina into the uterus, with a balloon of the uterine manipulator instrument of FIG. 21 in a deflated state, and with a sleeve of the uterine manipulator instrument in a proximal position.
Figure 25C:
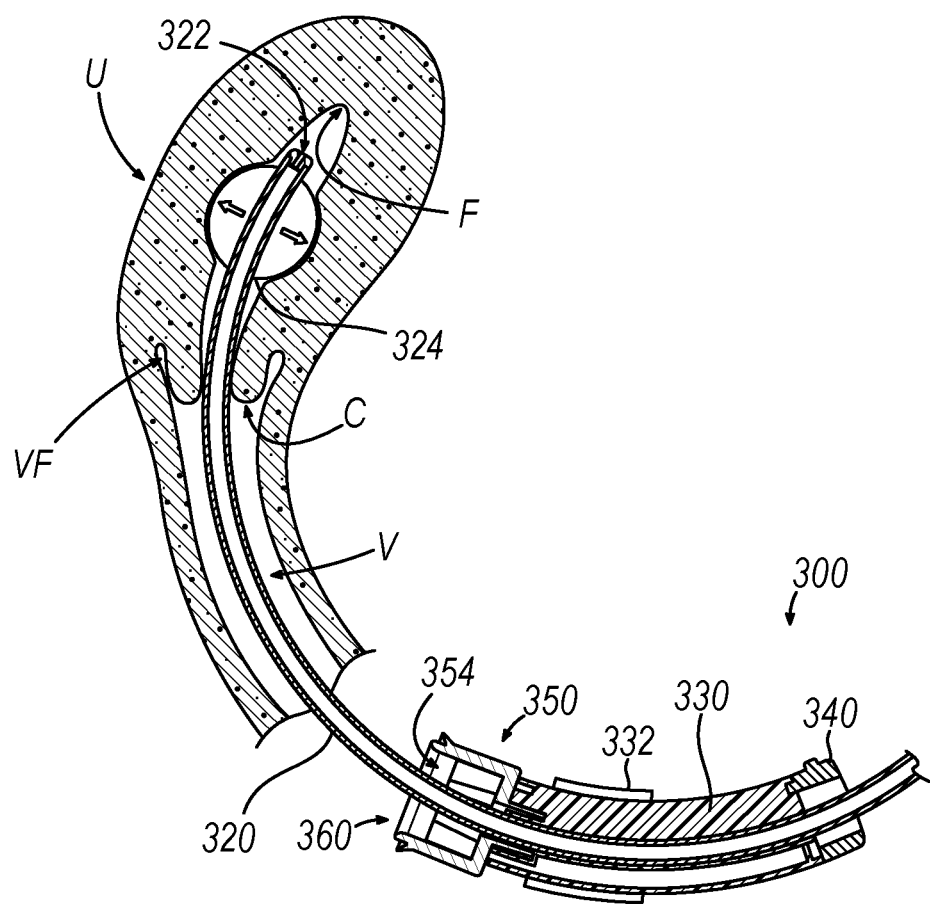
FIG. 25C depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in an inflated state, and with the sleeve of the uterine manipulator instrument in the proximal position.

FIGS. 25A-25E show an example of a procedure in which uterine manipulator (300) is used. As shown in FIG. 25A, the anatomical context in which uterine manipulator (300) is used includes a vagina (V) and uterus (U) of a patient. As shown in FIG. 25B, shaft (320) is inserted through the vagina (V) and into the uterus (U) via the cervix (C), while sleeve (330) is in a proximal position along shaft (320). Balloon (324) is in a deflated state during this stage of insertion. In some versions, uterine manipulator (300) is fully decoupled from robotic arm (200) during the process leading up to the stage shown in FIG. 25B, such that uterine manipulator (300) is advanced to this state manually by a human operator grasping a proximal portion of uterine manipulator (300) (e.g., grasping a proximal portion of shaft (320), grasping base (312), and/or grasping some other part of uterine manipulator (300)). In such scenarios, uterine manipulator (300) may be coupled with robotic arm (200) after reaching the stage shown in FIG. 25B.

In some other versions, uterine manipulator (300) is already coupled with robotic arm (200) before reaching the stage shown in FIG. 25B; and robotic arm (200) is used to guide and drive uterine manipulator (300) to the position shown in FIG. 25B. As yet another variation, some versions may allow a human operator to guide and drive uterine manipulator (300) to the position shown in FIG. 25B while uterine manipulator (300) is coupled with robotic arm (200), such that robotic arm (200) does not restrict manual movement of uterine manipulator (300) leading up to the stage shown in FIG. 25B.

Regardless of the stage at which uterine manipulator (300) is coupled with robotic arm (200), robotic arm (200) may be positioned in various suitable ways relative to the patient while uterine manipulator (300) is inserted in the patient. In some scenarios, robotic arm (200) crosses over the top of one of the patient's legs from the side, to assist in positioning uterine manipulator (300). In some other scenarios (e.g., when the patient's legs are supported by stirrups (58)), robotic arm (200) crosses under the bottom of one of the patient's legs from the side, to assist in positioning uterine manipulator (300). In still other scenarios, robotic arm (200) is positioned between the patient's legs from underneath, such that robotic arm (200) does not cross over or under either of the patient's legs. Alternatively, robotic arm (200) may have any other suitable spatial and positional relationship with respect to the patient.

In the present example, uterine manipulator (300) is advanced distally until distal end (322) of shaft (320) reaches the fundus (F) of the uterus (U). The operator may determine that distal end (322) has reached the fundus (F) via tactile feedback (e.g., such that the operator can feel sudden resistance to further advancement of shaft (320)). In addition, or in the alternative, in versions where distal end (322) includes an illuminating element, the illuminating element may provide transillumination through the wall of the uterus (U). Such transillumination may be observed via a laparoscope or other visualization device that is positioned external to the uterus (U). Such transillumination may indicate the extent to which shaft (320) has been inserted into the uterus (U). In some cases where distal end (322) contacts the fundus (F), distal end (322) may remain in contact with fundus (F) throughout the rest of the procedure shown in FIGS. 25B-25E. In some other versions, distal end (322) may be slightly backed out proximally, such that distal end (322) does not contact fundus (F) throughout the rest of the procedure shown in FIGS. 25B-25E.

After reaching the state shown in FIG. 25B, balloon (324) may be inflated as described above; and as shown in FIG. 25C. In some cases, balloon (324) is inflated to a point where balloon (324) bears outwardly against the sidewall of the uterus (U). In any case, the inflated balloon (324) may stabilize the distal portion of shaft (320) relative to the uterus (U). Specifically, the inflated balloon (324) may prevent shaft (320) from exiting proximally from the uterus (U) via the cervix (C). Balloon (324) may thus serve as a distally-positioned anchor structure for uterine manipulator (300). The inflated balloon (324) may also provide sufficient engagement between shaft (320) and the uterus (U) to allow use of shaft (320) to reposition and reorient the uterus (U) as described herein.

Figure 25D:
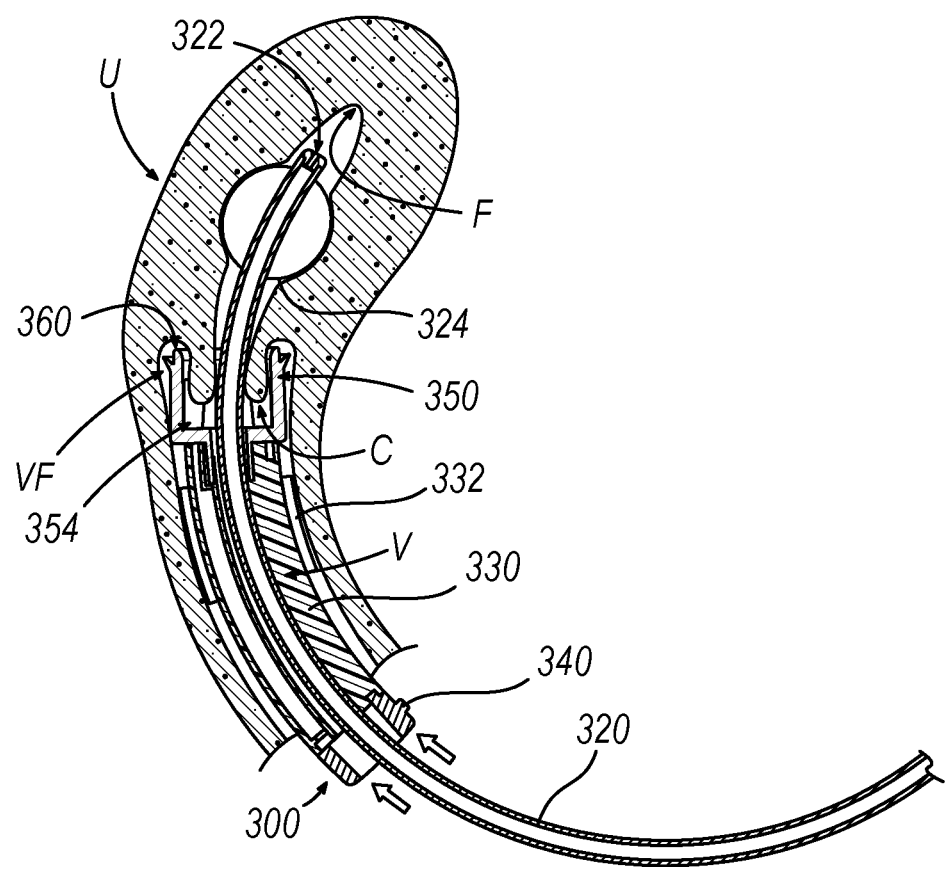
FIG. 25D depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in the inflated state, with the sleeve of the uterine manipulator instrument in a distal position such that the colpotomy cup of the sleeve is engaged with the cervix, and with a balloon of the sleeve in a deflated state.

With balloon (324) in the inflated state the operator may advance sleeve (330) distally along shaft (320) to the position shown in FIG. 25D. In the present example, this is performed by a human operator manually advancing sleeve (330) distally along shaft (320). In some other versions, this may be performed by a robotic operator robotically advancing sleeve (330) distally along shaft (320). As shown, sleeve (330) is advanced distally to a point where distal end (360) is firmly seated in the vaginal fornix (VF). The cervix (C) is received in interior space (354) of body (352). At this stage, the longitudinal position of sleeve (330) along shaft (320) is locked in place via locking ring (340). Specifically, the operator grasps locking ring (340) and rotates locking ring (340) about shaft (320) to firmly lock the position of sleeve (330) along shaft (320). In the present example, this is performed by a human operator, though it may be performed by a robotic operator in other versions. With the position of sleeve (330) locked in place against shaft (320), the position of uterine manipulator (300) is substantially fixed relative to the vagina (V), the cervix (C), and the uterus (U). While balloon (324) serves as a distally-positioned anchor structure for uterine manipulator (300), colpotomy cup (350) serves as a proximally-positioned anchor structure for uterine manipulator (300).

Figure 25E:
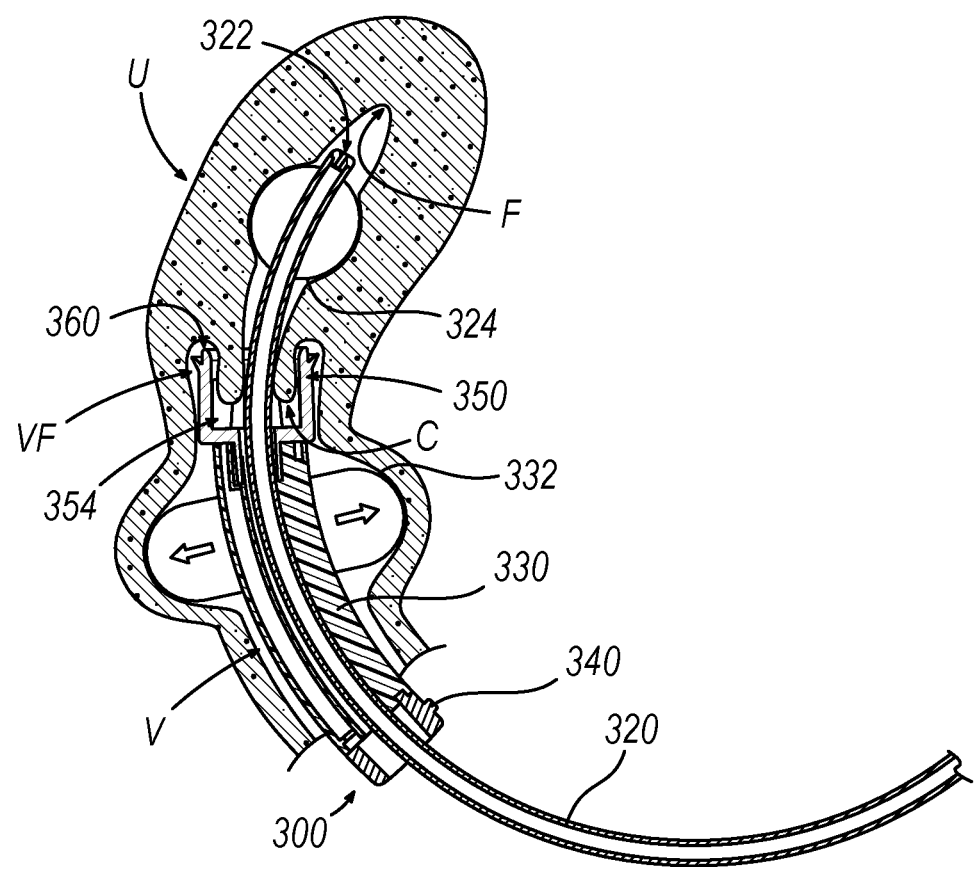
FIG. 25E depicts a mid-sagittal cross-sectional view of the vagina and uterus of FIG. 25A, with the shaft of the uterine manipulator instrument of FIG. 21 inserted through the vagina into the uterus, with the balloon of the uterine manipulator instrument of FIG. 21 in the inflated state, with the sleeve of the uterine manipulator instrument in the distal position such that the colpotomy cup of the sleeve is engaged with the cervix, and with the balloon of the sleeve in an inflated state.

With the position of uterine manipulator (300) being fixed by the combination of balloon (324) and colpotomy cup (350), balloon (332) is inflated as shown in FIG. 25E. Balloon (332) bears outwardly against the sidewall of the vagina (V), thereby creating a fluid-tight seal against the sidewall of the vagina (V).

With uterine manipulator (300) being positioned and configured as shown in FIG. 25E, robotic arm (200) may be utilized to drive uterine manipulator (300) to various positions, to thereby re-orient and reposition the uterus (U) as desired by the clinician who is performing the rest of the medical procedure (e.g., hysterectomy). In some scenarios, the clinician who robotically controls robotic arm (200) to drive uterine manipulator (300) to position and orient the uterus (U) also uses the same robotic system to control instruments that are used to perform a surgical procedure associated with the uterus (U) (e.g., a hysterectomy). As noted above, by allowing a surgeon to directly control the manipulation of the uterus (U) via robotic arm (200) and uterine manipulator (300), the process avoids potential confusion and inconsistency that might otherwise result in procedures where a human assistant is controlling a uterine manipulator based on commands from another human clinician. Moreover, once the uterus (U) has been manipulated to achieve the desired position and orientation, robotic arm (200) and uterine manipulator (300) may cooperate to maintain this position and orientation of the uterus (U) indefinitely. This may avoid scenarios where a human operator of a uterine manipulator might inadvertently reposition or reorient the uterus (U) in the middle of a medical procedure.

As noted above, one medical procedure that may be performed using robotic arm (200) and uterine manipulator (300) is a hysterectomy. In some versions of such a procedure, one or more cutting instruments are introduced laparoscopically via the patient's abdomen to approach the cervicovaginal junction from outside the uterus (U) and vagina (V). Such instrumentation may be controlled manually or robotically. In versions where the instrumentation is controlled robotically, the same robotic system may control the instrumentation and robotic arm (200). A cutting instrument may cut the uterus (U) away at the cervicovaginal junction, generally tracing around the circular perimeter defined by distal end (360) of colpotomy cup (350).

In some versions, the tissue at the cervicovaginal junction may be distended in response to pressure imposed by distal end (360) of colpotomy cup (350), thereby promoting visualization of the position of distal end (360) of colpotomy cup (350) from a laparoscope that is positioned external to the uterus (U) and vagina (V). Distal end (360) may also urge the ureters of the patient outwardly, thereby reducing the risk of the cutting instrument inadvertently cutting one of the ureters. Also in some versions, the cutting instrument may be received in space (366) defined between edges (362, 364) at distal end (360) of colpotomy cup (350) as the cutting instrument travels in a generally circular motion along the cervicovaginal junction. This cutting at the cervicovaginal junction will ultimately result in separation of the uterus (U) from the vagina (V); and the end of the vagina (V) may be appropriately closed at this point. During this process, the patient's abdomen may be insufflated with pressurized gas, and the pressurized insufflation gas may eventually reach the distal region of the vagina (V). In such scenarios, balloon (332) will provide sealed occlusion that is sufficient to prevent the pressurized insufflation gas from escaping out of the patient via the vagina (V).

While robotic arm (200) and uterine manipulator (300) are described in the foregoing example as being used in a hysterectomy, robotic arm (200) and uterine manipulator (300) may be used in any other suitable fashion and may be used in any other suitable procedures.

III. Exemplary Articulation and Sensing Features for Uterine Manipulator

In some instances, it may be desirable to enable manipulation of the uterus (U), such as re-orienting and/or repositioning of the uterus (U), via articulation or other movement of a distal portion of uterine manipulator (300) relative to a proximal portion of uterine manipulator (300) (e.g., while the proximal portion remains stationary). Accordingly, in some such instances, it may be desirable to configure uterine manipulator (300) with features that enable such relative movement. In addition, or alternatively, it may be desirable to enable monitoring of the manipulation of the uterus (U) based on feedback from one or more sensors associated with uterine manipulator (300). Exemplary versions of such features are described in greater detail below.

A. Exemplary Uterine Manipulator with Distal Manipulation Balloon

Figure 26A:
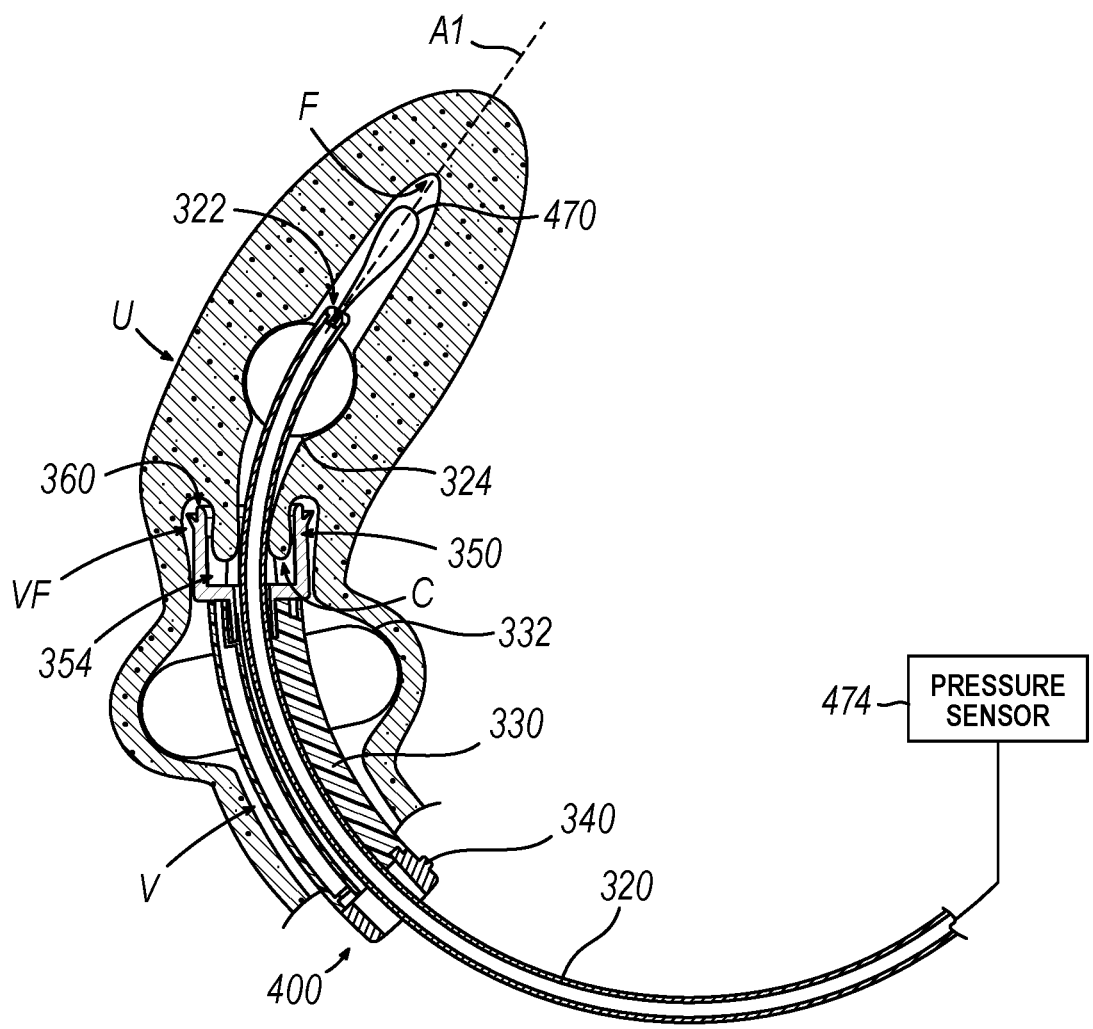
FIG. 26A depicts a mid-sagittal cross-sectional view of the vagina and uterus of FIG. 25A, with a shaft of another exemplary uterine manipulator instrument inserted through the vagina into the uterus, with a distal manipulation balloon of the uterine manipulator instrument in a first inflated state.
Figure 26B:
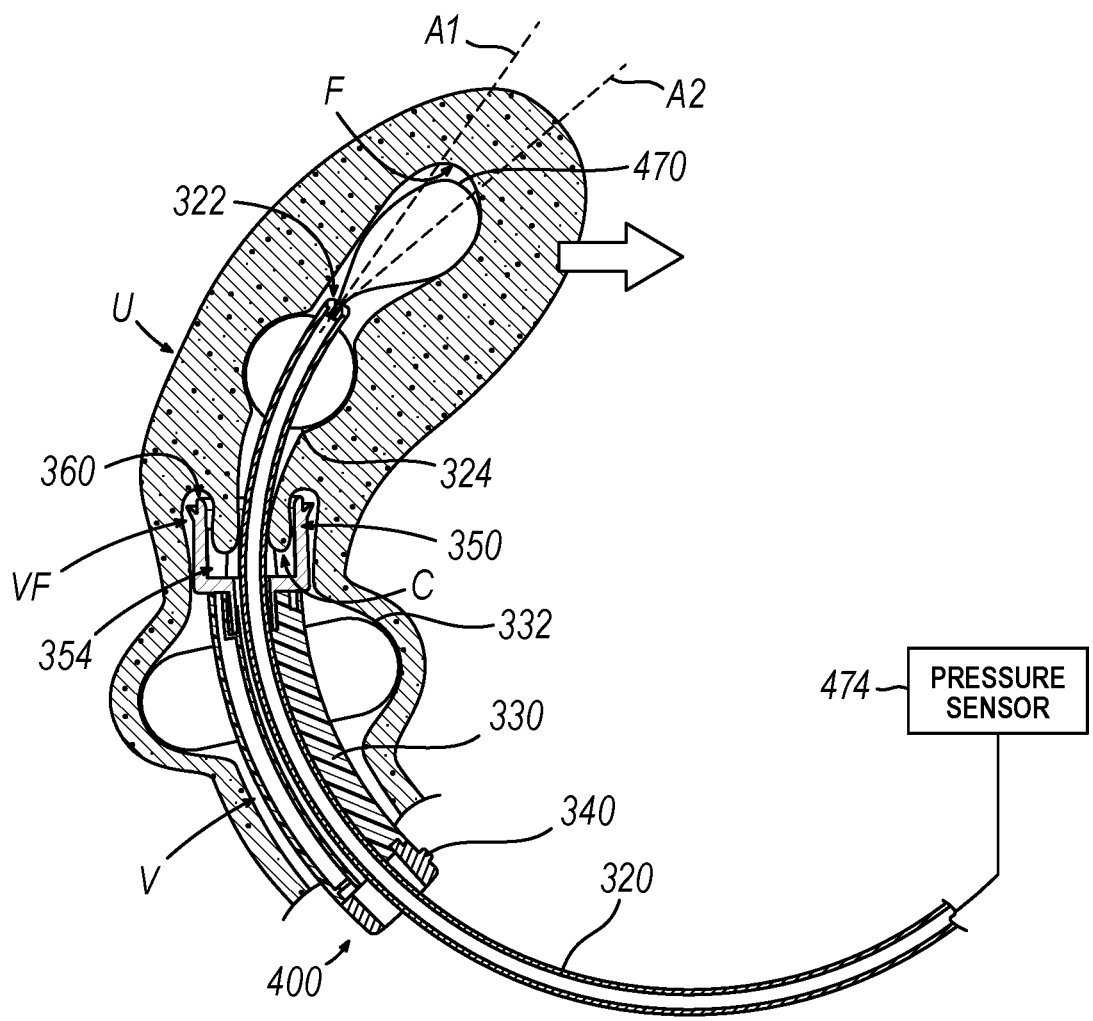
FIG. 26B depicts a mid-sagittal cross-sectional view of the vagina and uterus of FIG. 25A, with the shaft of the uterine manipulator instrument of FIG. 26A inserted through the vagina into the uterus, with the distal manipulation balloon of the uterine manipulator instrument in a second inflated state to manipulate the uterus.

FIGS. 26A-26B depict an exemplary uterine manipulator (400) for use with robotic arm (200). Uterine manipulator (400) is similar to uterine manipulator (300) described above except as otherwise described below. In this regard, uterine manipulator (400) includes a head interface assembly (not shown), such as head interface assembly (310), shaft (320), balloon (324), sleeve (330), balloon (332), sleeve locking ring (340), and colpotomy cup (350). Uterine manipulator (400) may be removably coupled with head (240) of robotic arm (200), such that robotic arm (200) may selectively position and orient uterine manipulator in relation to a patient by driving robotic arm (200).

Uterine manipulator (400) of the present version includes an articulation member in the form of at least one inflatable balloon (470) extending distally from distal end (322) of shaft (320). Balloon (470) may be formed of an extensible material or a non-extensible material, as described in greater detail below. The interior of shaft (320) includes one or more lumen(s) that are configured to communicate pressurized fluid from pressurized fluid source (302) to balloon (470). Pressurized fluid source (302) may include a valve control or other actuator in operative communication with controller (182), such as via one or more wires, for receiving control signals from controller (182), for example, to selectively communicate pressurized fluid to balloon (470). In the example shown, a pressure sensor (474) is operatively coupled to a proximal end of shaft (320) for detecting the fluid pressure within the lumen(s) of shaft (320) and/or within balloon (470). Pressure sensor (474) may be configured to generate feedback signals indicative of the detected fluid pressure and may be in operative communication with controller (182), such as via one or more wires, for sending such feedback signals to controller (182), for example. While balloon (470) extends distally from distal end (322) of shaft (320) in the present example, other versions may include a different kind of articulation member, such as a rigid, mechanically articulatable component as described below in connection with FIGS. 27A-28. In some versions, balloon (470) may be extendable from a longitudinally retracted (e.g., proximal) position in which balloon (470) is housed within an interior of shaft (320) (not shown) to one or more longitudinally extended (e.g., distal) positions in which balloon (470) extends distally from distal end (322) of shaft (320), as shown in FIGS. 26A-26B.

With continuing reference to FIGS. 26A-26B, balloon (470) of the present example is selectively inflatable from a first state (FIG. 26A) to a second state (FIG. 26B). In some versions, balloon (470) is fully deflated in the first state, and is at least partially inflated in the second state. In other versions, balloon (470) is partially inflated in the first state, such as for transitioning balloon (470) from the retracted position to the extended position, and is relatively more inflated in the second state than in the first state. When balloon (470) is in the first state shown in FIG. 26A, balloon (470) generally extends along a first axis (A1) defined by at least a portion of shaft (320) such that balloon (470) may permit the uterus (U) to remain in an initial (e.g., natural) position and/or orientation. In the present version, first axis (A1) is straight and is defined by distal end (322) of shaft (320). In other versions, first axis (A1) may be curved and may be defined by a portion of shaft (320) proximal of distal end (322), for example. When balloon (470) is in the second state shown in FIG. 26B, balloon (470) generally extends at least partially along a second axis (A2) transverse to first axis (A1) such that balloon (470) may bear against the sidewall of the uterus (U) on a first transverse side of first axis (A1) to thereby re-orient and/or reposition the uterus (U) away from the initial position and/or orientation. For example, at least a distal portion of balloon (470) may extend along second axis (A2) transverse to first axis (A1). In some versions, second axis (A2) may be obliquely oriented relative to first axis (A1). In this manner, balloon (470) may re-orient and/or reposition the uterus (U) to a subsequent position and/or orientation shown in FIG. 26B to facilitate the operation(s) to be performed, such as a hysterectomy.

In some versions, balloon (470) is formed of a non-extensible material and has a predefined shape, such that balloon (470) automatically assumes the predefined shape when in the second state to manipulate the uterus (U) in a predetermined manner. In this regard, the predefined shape may be selected to provide a desired orientation and/or position of the uterus (U). In addition, or alternatively, the predefined shape may allow manipulation of the uterus (U) through pressure distribution. In other versions, balloon (470) may be formed of a combination of extensible portions and non-extensible portions. In such cases, the extensible and non-extensible portions may be arranged to provide the predefined shape as balloon (470) is inflated. In other versions, balloon (470) may be configured with different wall thicknesses. In such cases, the different wall thickness may be arranged to provide the predefined shape as balloon (470) is inflated. In other versions, a proximal portion of balloon (470) may be equipped with one or more hydraulically and/or pneumatically actuatable joints for selectively re-orienting balloon (470) to thereby re-orient and/or reposition the uterus (U). Such joints may be configured to actuate inflated segments of balloon (470) that are relatively rigid when inflated. In other versions, a plurality of inflatable balloons (470) may extend distally from distal end (322) of shaft (320) and/or from each other to collectively define a balloon assembly (not shown). In such cases, each balloon (470) may be independently inflatable to permit selective inflation of one or more selected balloon(s) (470) while optionally maintaining one or more unselected balloon(s) in uninflated states, to cause the balloon assembly to assume a desired shape to manipulate the uterus (U) in a desired manner. In some such cases, the plurality of balloons (470) may be collectively housed or otherwise defined within a common bladder. For example, the common bladder may include a plurality of chambers, each defining a respective balloon (470).

During operation, uterine manipulator (400) may be inserted in the patient, advanced distally, and anchored in the uterus (U) in a manner similar to that described above in connection with FIGS. 25A-25E. In some versions, balloon (470) may be transitioned from the retracted position to the extended position after the position of sleeve (330) has been locked along shaft (320) to provide distal insertion of uterine manipulator (400) beyond distal end (322) of shaft (320), which may assist with stabilizing uterine manipulator (300) relative to the uterus (U). Robotic arm (200) may then be utilized to drive uterine manipulator (400) to various positions, to thereby re-orient and/or reposition the uterus (U). For example, robotic arm (200) may move to pivot uterine manipulator (400) about a remote center of motion (RCM) at or near the vaginal opening for manipulating the uterus (U). In addition, or alternatively, balloon (470) may be inflated from the first state to the second state to thereby re-orient and/or reposition the uterus (U) in the manner described above. In this regard, controller (182) may monitor the manipulation of the uterus (U) based on the fluid pressure within balloon (470) as indicated by the feedback signals received by controller (182) from pressure sensor (474), in a manner similar to that described below in connection with FIGS. 31-32, and may take appropriate action in accordance therewith, such as adjusting the fluid pressure within balloon (470) to achieve the desired manipulation of the uterus (U), communicating the measured fluid pressure to the clinician, and/or alerting the clinician that the measured fluid pressure has reached or exceeded a predetermined threshold. For example, a relatively high fluid pressure measurement obtained during inflation of balloon (470) may indicate that the uterus (U) has not yet been successfully mobilized due to a significant amount of connective tissue remaining, such that further dissection may be warranted before further manipulation of the uterus (U).

In some versions, balloon (324) may be omitted and balloon (470) may provide one or more of the functionalities of balloon (324) described above in connection with FIGS. For example, after uterine manipulator (400) is advanced to a state similar to that shown in FIG. 25B, balloon (470) may be inflated to a point where balloon (470) bears outwardly against the sidewall of the uterus (U) to stabilize the distal portion of shaft (320) relative to the uterus (U), while permitting the uterus (U) to remain in its initial (e.g., natural) position and/or orientation. Specifically, the inflated balloon (470) may prevent shaft (320) from exiting proximally from the uterus (U) via the cervix (C). Balloon (470) may thus serve as a distally-positioned anchor structure for uterine manipulator (300). Subsequently, (e.g., after balloon (332) is inflated to a state similar to that shown in FIG. to create a fluid-tight seal against the sidewall of the vagina (V)), balloon (470) may be further inflated to thereby re-orient and/or reposition the uterus (U) in the manner described above.

B. Exemplary Uterine Manipulator with Distal Manipulation Finger

Figure 27A:
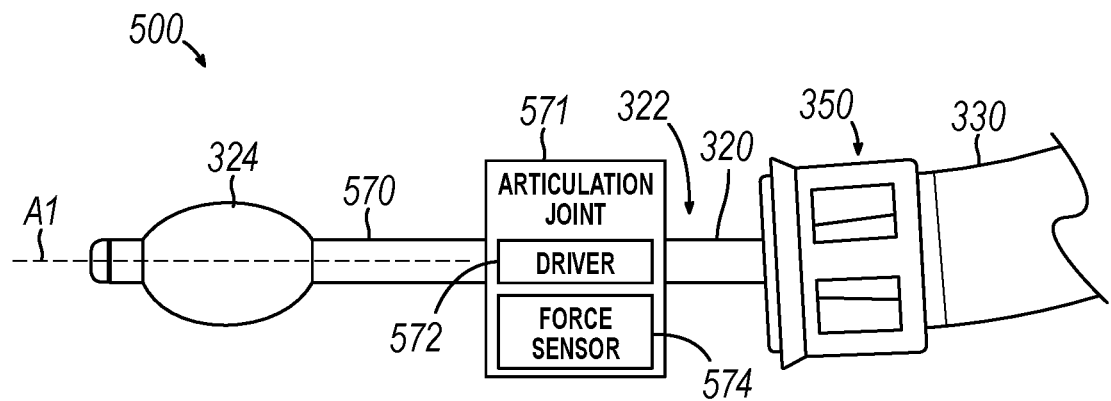
FIG. 27A depicts a side elevation view of a distal portion of another exemplary uterine manipulator instrument having a distal manipulation finger, showing the distal manipulation finger in a first articulated state.
Figure 27B:
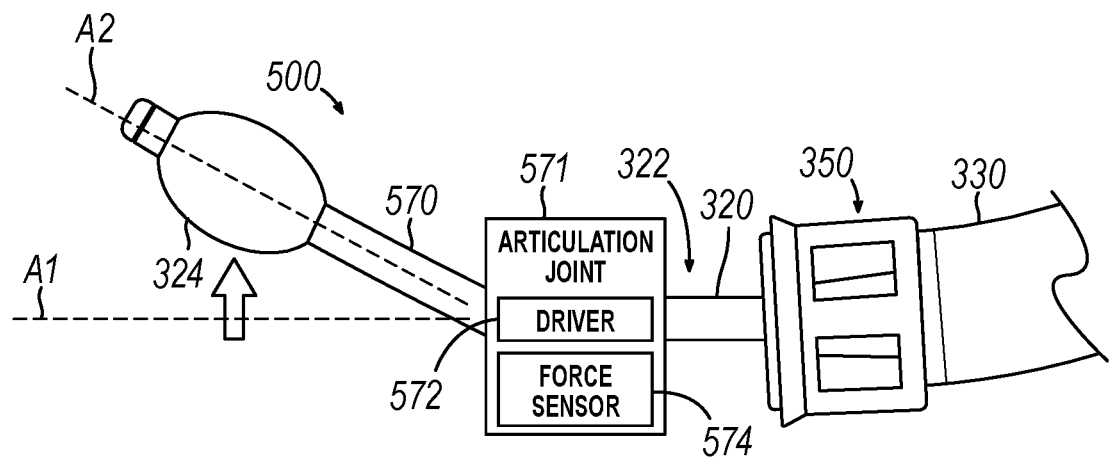
FIG. 27B depicts a side elevation view of the distal portion of the uterine manipulator instrument of FIG. 27A, showing the distal manipulation finger in a second articulated state to manipulate a uterus.
Figure 28:
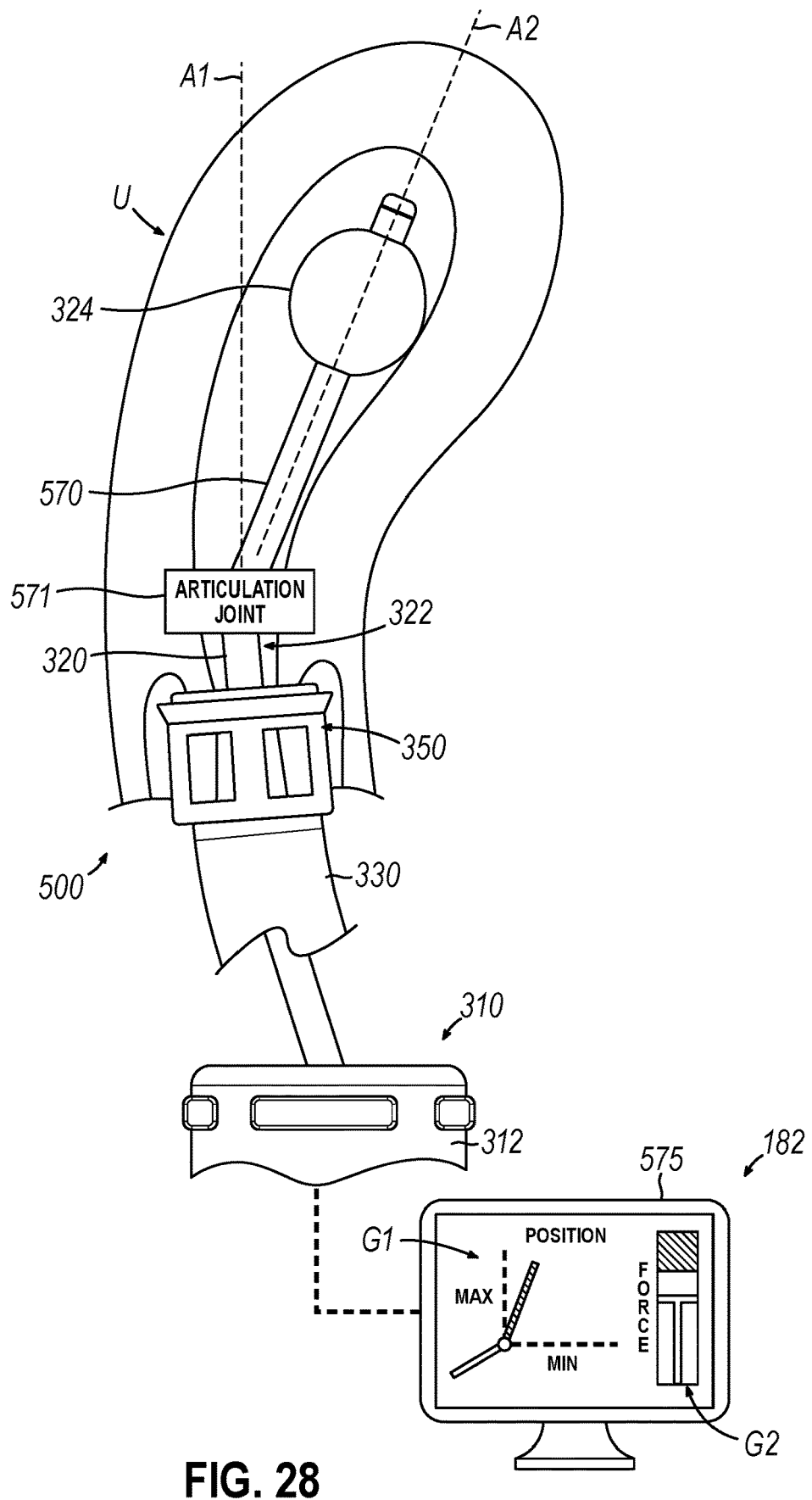
FIG. 28 depicts a schematic view of a robotic system including the uterine manipulator instrument of FIG. 27A and the controller of FIG. 19, showing the distal manipulation finger of the uterine manipulator instrument in the second articulated state, and further showing a display screen of the controller depicting the articulation of the distal manipulation finger and the force acting upon the distal manipulation finger.

FIGS. 27A-28 depict another exemplary uterine manipulator (500) for use with robotic arm (200). Uterine manipulator (500) is similar to uterine manipulator (400) described above except as otherwise described below. In this regard, uterine manipulator (500) includes head interface assembly (310), shaft (320), balloon (324), sleeve (330), a proximal sealing balloon (not shown), such as balloon (332), a sleeve locking ring (not shown), such as sleeve locking ring (340), and colpotomy cup (350). Uterine manipulator (500) may be removably coupled with head (240) of robotic arm (200), such that robotic arm (200) may selectively position and orient uterine manipulator (500) in relation to a patient by driving robotic arm (200).

Uterine manipulator (500) of the present version includes an articulation member in the form of at least one mechanically articulatable finger (570) extending distally from distal end (322) of shaft (320). Finger (570) may be formed of a substantially rigid material. In the example shown, finger (570) is coupled to distal end (322) of shaft (320) via an articulation joint (571) for facilitating articulation of finger (570) relative to shaft (320). In this regard, articulation joint (571) of the present example includes an actuator or driver (572) configured to selectively actuate articulation of finger (570) relative to shaft (320). In some versions, driver (572) may be configured to actuate articulation of finger (570) via one or more cables (not shown) operatively coupled to head interface assembly (310). In other versions, driver (572) may be configured to actuate articulation of finger (570) via selective inflation of one or more balloons positioned at or near a proximal end of finger (570), for example. In other versions, driver (572) may include one or more servo motors or other electromechanical components suitable for actuating articulation of finger (570). Driver (572) may be in operative communication with controller (182), such as via head interface assembly (310), for receiving control signals from controller (182), for example. Articulation joint (571) also includes a force sensor (574) for detecting one or more force(s) acting upon finger (570). In some versions, force sensor (574) may include one or more torque sensor(s) associated with driver (572). Force sensor (574) may be configured to generate feedback signals indicative of the detected force and may be in operative communication with controller (182), such as via head interface assembly (310), for sending such feedback signals to controller (182), for example.

In the example shown, balloon (324) is positioned over finger (570) near a distal end thereof. In this regard, the interior of finger (570) may include one more lumen(s) that are configured to communicate pressurized fluid from the lumen(s) of shaft (320) to balloon (324). In other versions, balloon (324) may be positioned over shaft (320) near distal end (322) of shaft (320) as described above in connection with FIGS. 21-25E.

With continuing reference to FIGS. 27A-27B, finger (570) of the present example is selectively articulatable relative to shaft (320) via articulation joint (571) from a first state (FIG. 27A) to at least one second state (FIG. 27B). When finger (570) is in the first state shown in FIG. 27A, finger (570) generally extends along a first axis (A1) defined by at least a portion of shaft (320) such that finger (570) may permit the uterus (U) to remain in an initial (e.g., natural) position and/or orientation. In the present version, first axis (A1) is straight and is defined by distal end (322) of shaft (320). In other versions, first axis (A1) may be curved and may be defined by a portion of shaft (320) proximal of distal end (322), for example. When finger (570) is in the second state shown in FIGS. 27B and 28, finger (570) generally extends at least partially along a second axis (A2) transverse to first axis (A1) such that finger (570) (and/or balloon (324)) may bear against the sidewall of the uterus (U) on a first transverse side of first axis (A1) to thereby re-orient and/or reposition the uterus (U) away from the initial position and/or orientation. For example, at least a distal portion of finger (570) and/or at least a distal portion of balloon (324) may extend along second axis (A2) transverse to first axis (A1). In some versions, second axis (A2) may be obliquely oriented relative to first axis (A1). In this manner, finger (570) may re-orient and/or reposition the uterus (U) to a subsequent position and/or orientation to facilitate the operation(s) to be performed, such as a hysterectomy. While finger (570) of the present example is shown articulating along a single plane, articulation joint (571) may provide articulation of finger (570) along two or more planes, or with any other suitable degree(s) of freedom. In some versions, articulation joint (571) may provide different degrees of freedom by allowing finger (570) to spin at articulation joint (571), about the first axis (A1) to thereby reorient the plane along which finger (570) articulates.

During operation, uterine manipulator (500) may be inserted in the patient, advanced distally, and anchored in the uterus (U) in a manner similar to that described above in connection with FIGS. 25A-25E. Robotic arm (200) may then be utilized to drive uterine manipulator (500) to various positions, to thereby re-orient and/or reposition the uterus (U). In addition, or alternatively, finger (570) may be articulated from the first state to the second state to thereby re-orient and/or reposition the uterus (U) in the manner described above. In this regard, controller (182) may monitor the manipulation of the uterus (U) based on the force acting upon finger (570) as indicated by the feedback signals received by controller (182) from force sensor (574), and may take appropriate action in accordance therewith, such as adjusting the articulation of finger (570) to achieve the desired manipulation of the uterus (U), communicating the measured force to the clinician, and/or alerting the clinician that the measured force has reached or exceeded a predetermined threshold. For example, a relatively high force measurement obtained during articulation of finger (570) may indicate that the uterus (U) has not yet been successfully mobilized due to a significant amount of connective tissue remaining, such that further dissection may be warranted before further manipulation of the uterus (U).

In this regard, and as shown in FIG. 28, controller (182) may include a display screen (575) for communicating the degree of articulation of finger (570) and/or the amount of forcing acting upon finger (570) to the clinician. Display screen (575) of the present example depicts a first graphic (G1) representing the current degree of articulation of finger (570) illustrated relative to predetermined minimum and maximum degrees of articulation of finger (570), in real-time. In some versions, controller (182) may determine the current degree of articulation of finger (570) based on one or more feedback signals received from driver (572) and/or head interface assembly (310). For example, head interface assembly (310) may include one or more encoders for detecting the state of the cable(s) used to actuate articulation of finger (570), and such encoders may be in operative communication with controller (182), which may correlate the detected state of the cable(s) to the degree of articulation of finger (570). In any event, display screen (575) of the present example also depicts a second graphic (G2) representing the current amount of force acting upon finger (570) illustrated on a simulated scale. Controller (182) may determine the current amount of force acting upon finger (570) based on the feedback signals received by controller (182) from force sensor (574) as described above.

C. Exemplary Uterine Manipulator with Impedance Sensors

Figure 29:
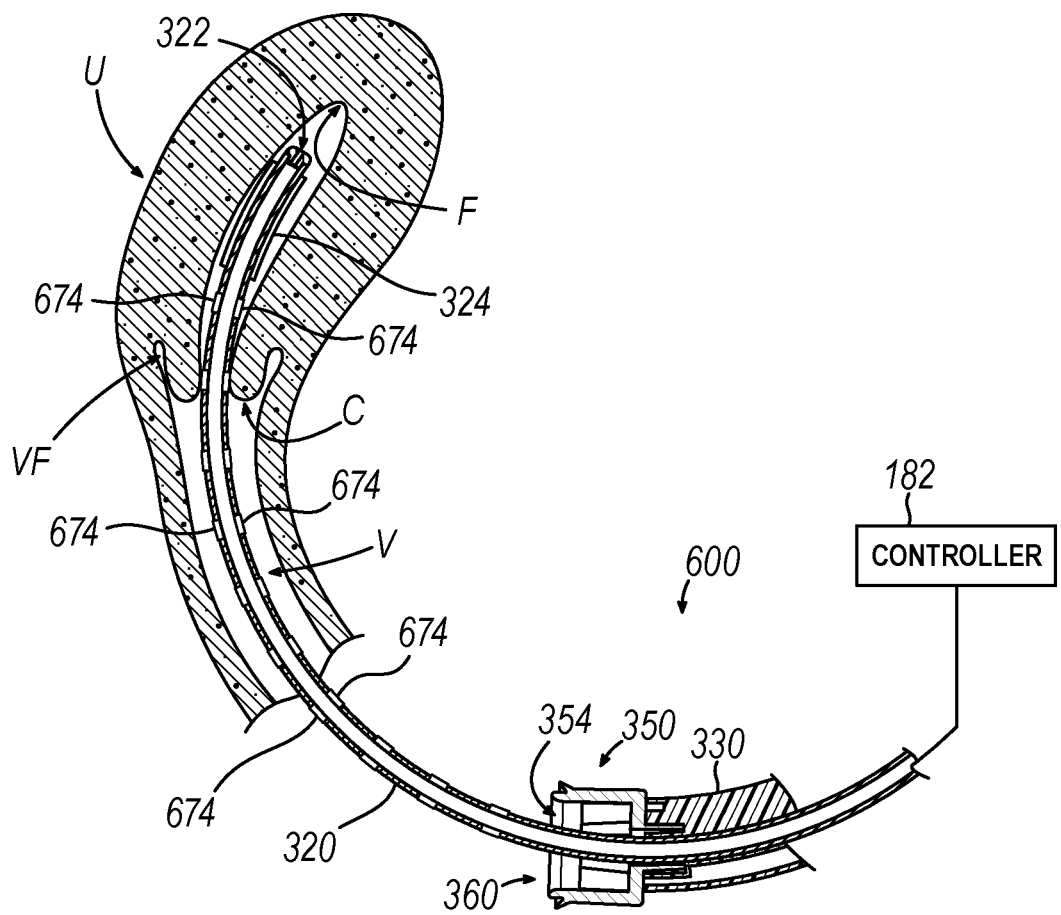
FIG. 29 depicts a mid-sagittal cross-sectional view of the vagina and uterus of FIG. 25A, with the shaft of another exemplary uterine manipulator instrument inserted through the vagina into the uterus, with a plurality of impedance sensors positioned along the shaft for sensing tissue and air.

FIG. 29 depicts another exemplary uterine manipulator (600) for use with robotic arm (200). Uterine manipulator (600) is similar to uterine manipulator (300) described above except as otherwise described below. In this regard, uterine manipulator (600) includes a head interface assembly (not shown), such as head interface assembly (310), shaft (320), balloon (324), sleeve (330), a proximal sealing balloon (not shown), such as balloon (332), a sleeve locking ring (not shown), such as sleeve locking ring (340), and colpotomy cup (350). Uterine manipulator (600) may be removably coupled with head (240) of robotic arm (200), such that robotic arm (200) may selectively position and orient uterine manipulator in relation to a patient by driving robotic arm (200).

Uterine manipulator (600) of the present version includes at least one longitudinal array of impedance sensors (674) spaced apart from each other at predetermined intervals along an outer surface of shaft (320) for detecting the electrical impedance(s) of objects (e.g., tissue) and/or fluid media (e.g., air) contacting the impedance sensors (674). Impedance sensors (674) may each be configured to generate feedback signals indicative of the detected impedance(s) and may be in operative communication with controller (182), such as via one or more wires extending along the lumen(s) of shaft (320), for sending such feedback signals to controller (182), for example. In this regard, controller (182) may monitor the insertion depth of uterine manipulator (600) within the uterus (U) based on the impedance(s) of the tissue and/or air contacted by impedance sensors (674) as indicated by the feedback signals received by controller (182) from impedance sensors (674), and may take appropriate action in accordance therewith. Such appropriate action may include arresting distal advancement of uterine manipulator (600) in response to uterine manipulator (600)

reaching a predetermined depth, communicating the depth of uterine manipulator (600) to the clinician, and/or alerting the clinician to a potential perforation (e.g., in response to uterine manipulator (600) exceeding the predetermined depth and/or in response to relatively distal impedance sensors (674) contacting air or other fluid media external to the uterus (U) while relatively proximal impedance sensors (674) contact tissue).

For example, a first impedance detected by a first set of one or more impedance sensor(s) (674) may indicate that the first set of one or more impedance sensor(s) (674) is in contact with air (e.g., outside the patient); a second impedance detected by a second set of one or more impedance sensor(s) (674) may indicate that the second set of one or more impedance sensor(s) (674) is in contact with tissue of the vagina (V); a third impedance detected by a third set of one or more impedance sensor(s) (674) may indicate that the third set of one or more impedance sensor(s) (674) is in contact with tissue of the cervix (C); and a fourth impedance detected by a fourth set of one or more impedance sensor(s) (674) may indicate that the fourth set of one or more impedance sensor(s) (674) is in contact with tissue of the uterus (U).

Thus, controller (182) may utilize the detected impedances and the predetermined spacings between impedance sensors (674) to differentiate between specific types of tissue contacting impedance sensors (674) and to determine various measurements such as vaginal depth, cervical canal depth, and uterine depth.

In some versions, impedance sensors (674) may be utilized by controller (182) to automatically define a remote center of motion (RCM) about which uterine manipulator (600) may be pivoted for manipulating the uterus (U). For example, after uterine manipulator (600) has been inserted in the patient, advanced distally, and anchored in the uterus (U) in a manner similar to that described above in connection with FIGS. 25A-25E, controller (182) may determine the location(s) along sleeve (330) at which tissue contact is being made based on the impedance(s) of the tissue and/or air contacted by impedance sensors (674). Controller (182) may also determine the location(s) of sleeve (330) and/or colpotomy cup (350) along shaft (320) based on a capacitive scale or other linear sensing technique. Based on the location(s) along sleeve (330) at which tissue contact is being made and the location(s) of sleeve (330) and/or colpotomy cup (350) along shaft (320), controller (182) may identify the position of the opening of the vagina (V) relative to uterine manipulator (600) and may thereby define the RCM at or near the vaginal opening. Pivoting of uterine manipulator (600) about the RCM, such as via robotic arm (200), may then be performed to manipulate the uterus (U) in the desired manner.

D. Exemplary Uterine Manipulator with Force Sensors on Balloon

Figure 30A:
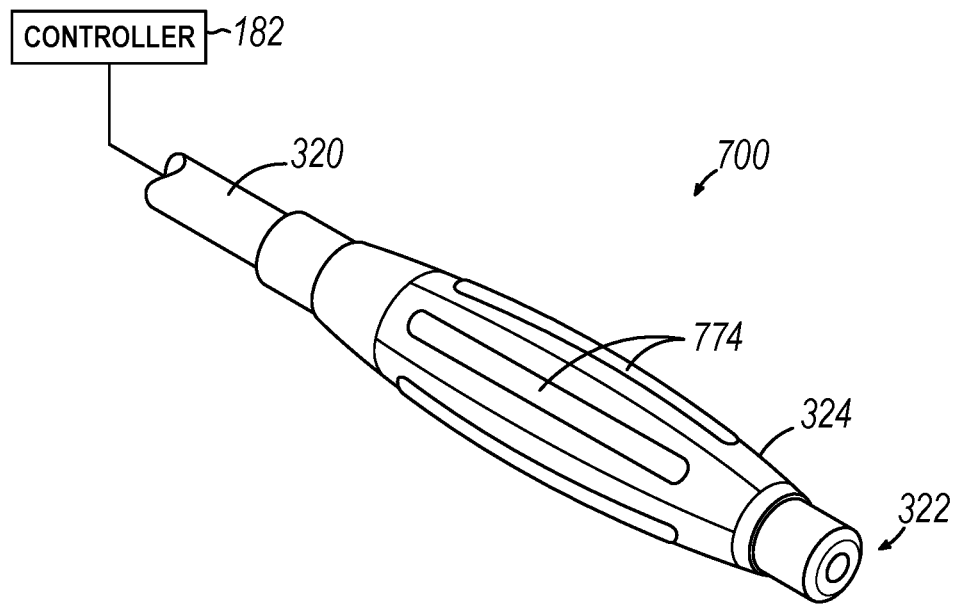
FIG. 30A depicts a perspective view of a distal portion of another exemplary uterine manipulator instrument with a balloon in a deflated state, and with a plurality of pressure sensing electrodes positioned on the balloon.
Figure 30B:
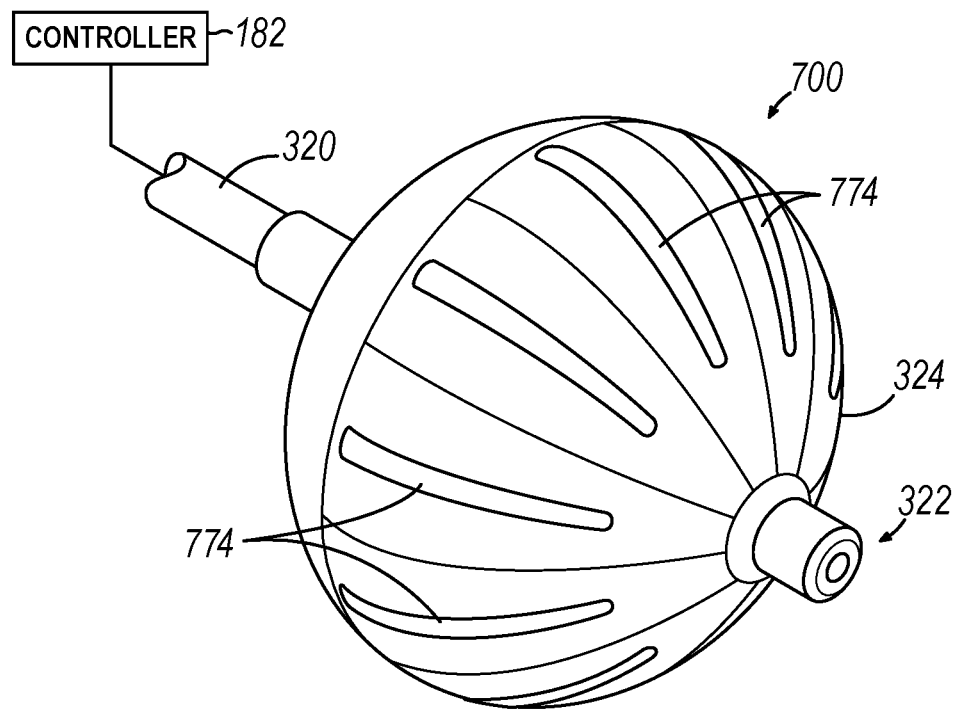
FIG. 30B depicts a perspective view of the distal portion of the uterine manipulator instrument of FIG. 30A with the balloon in an inflated state.

FIGS. 30A-30B depict a distal portion of an exemplary uterine manipulator (700) for use with robotic arm (200). Uterine manipulator (700) is similar to uterine manipulator (300) described above except as otherwise described below. In this regard, uterine manipulator (700) includes a head interface assembly (not shown), such as head interface assembly (310), shaft (320), balloon (324) inflatable from a first state (FIG. 30A) to a second state (FIG. 30B), a sleeve (not shown), such as sleeve (330), a proximal sealing balloon (not shown), such as balloon (332), a sleeve locking ring (not shown), such as sleeve locking ring (340), and a colpotomy cup (not shown), such as colpotomy cup (350). Uterine manipulator (700) may be removably coupled with head (240) of robotic arm (200), such that robotic arm (200) may selectively position and orient uterine manipulator in relation to a patient by driving robotic arm (200).

Uterine manipulator (700) of the present version includes a circumferential array of force sensors in the form of compliant electrodes (774) angularly spaced apart from each other at predetermined intervals over an outer surface of balloon (324) for detecting one or more force(s) acting upon balloon (324). Electrodes (774) may each be configured to generate feedback signals indicative of the detected force(s) and may be in operative communication with controller (182), such as via one or more wires extending along the lumen(s) of shaft (320), for sending such feedback signals to controller (182), for example. Such feedback signals may be generated based on resistance changes in electrodes (774) caused by corresponding force(s) acting thereupon. In some versions, electrodes (774) may each be configured as a thin film and may be formed of any suitable material or combination of materials, including but not limited to metallic conductive materials such as copper, gold, steel, aluminum, silver, nitinol, etc. and/or non-metallic conductive materials such as conducting polymers, silicides, graphite, etc. Electrodes (774) may be directly secured to balloon (324) or may be secured to intervening flexible substrates (not shown) using conventional circuit printing techniques, vapor deposition, or in any other suitable fashion as will be apparent to those skilled in the art in view of the teachings herein.

During operation, uterine manipulator (700) may be inserted in the patient, advanced distally, and anchored in the uterus (U) in a manner similar to that described above in connection with FIGS. 25A-25E. Robotic arm (200) may then be utilized to drive uterine manipulator (700) to various positions, to thereby re-orient and/or reposition the uterus (U). In this regard, controller (182) may monitor the manipulation of the uterus (U) based on the force acting upon balloon (324) as indicated by the feedback signals received by controller (182) from electrodes (774), and may take appropriate action in accordance therewith, such as adjusting the fluid pressure within balloon (324) and/or adjusting a position of balloon (324) to achieve the desired manipulation of the uterus (U), communicating the measured forces to the clinician, and/or alerting the clinician that the measured forces have reached or exceeded a predetermined threshold.

In some versions, electrodes (774) may be configured to individually or cooperatively deliver RF energy from an RF generator (not shown) to tissue positioned in electrical contact with electrodes (774), to thereby ablate the tissue with monopolar or bipolar RF energy. Alternatively, electrodes (774) may be configured to excite a gas that is introduced into the patient to achieve such ablation.

E. Exemplary Uterine Manipulator with Balloon Pressure Sensor

Figure 31:
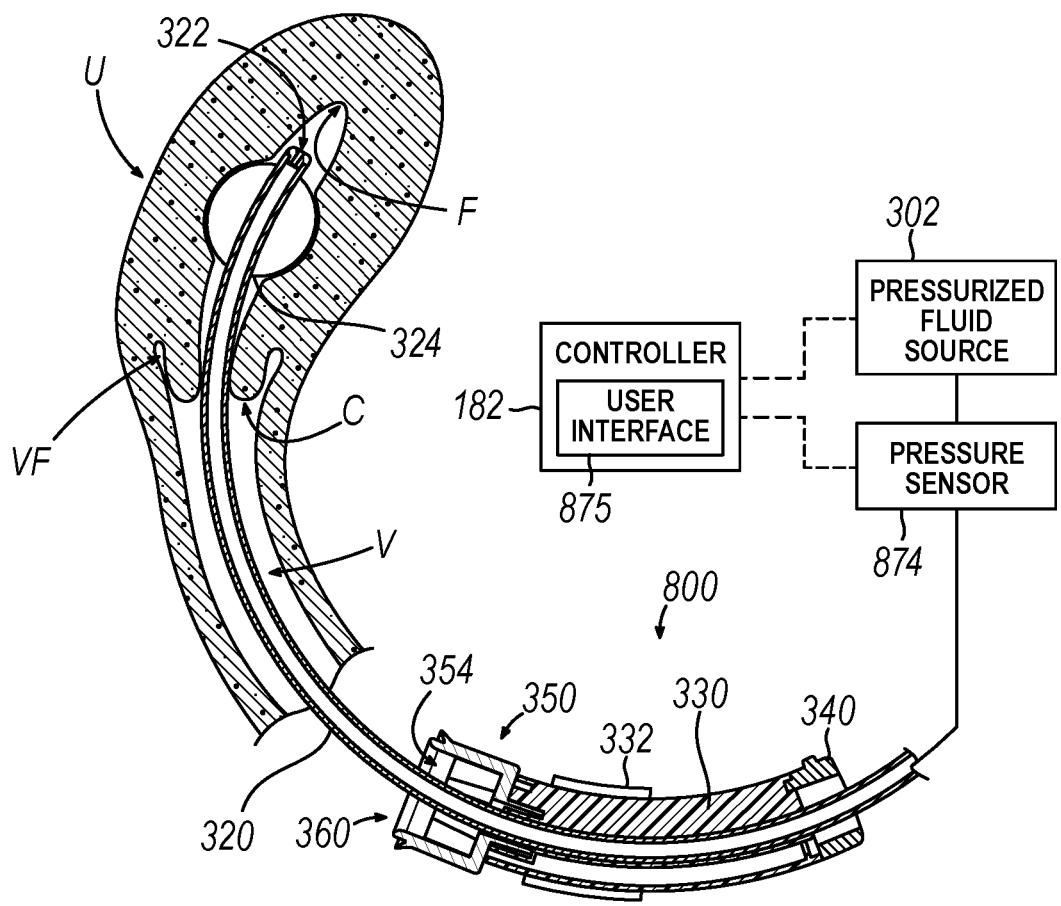
FIG. 31 depicts a mid-sagittal cross-sectional view of the vagina and uterus of FIG. with the shaft of another exemplary uterine manipulator instrument inserted through the vagina into the uterus, with a balloon of the uterine manipulator instrument in an inflated state, and with a pressure sensor positioned between the balloon and a pressurized fluid source.

FIG. 31 depicts another exemplary uterine manipulator (800) for use with robotic arm (200). Uterine manipulator (800) is similar to uterine manipulator (300) described above except as otherwise described below. In this regard, uterine manipulator (800) includes a head interface assembly (not shown), such as head interface assembly (310), shaft (320), balloon (324), sleeve (330), balloon (332), sleeve locking ring (340), and colpotomy cup (350). Uterine manipulator (800) may be removably coupled with head (240) of robotic arm (200), such that robotic arm (200) may selectively position and orient uterine manipulator in relation to a patient by driving robotic arm (200).

In the example shown, a pressure sensor (874) is arranged inline between pressurized fluid source (302) and the lumen (s) of shaft (320) that are configured to communicate pressurized fluid from pressurized fluid source (302) to balloon (324), for detecting the fluid pressure within the lumen(s) of shaft (320) and/or within balloon (324). As shown, pressurized fluid source (302) is in operative communication with controller (182), such as via one or more wires, for receiving control signals from controller (182), for example, to selectively communicate pressurized fluid to balloon (324). Pressure sensor (874) is configured to generate feedback signals indicative of the detected fluid pressure and is in operative communication with controller (182), such as via one or more wires, for sending such feedback signals to controller (182).

During operation, uterine manipulator (800) may be inserted in the patient, advanced distally, and anchored in the uterus (U) in a manner similar to that described above in connection with FIGS. 25A-25E. Robotic arm (200) may then be utilized to drive uterine manipulator (800) to various positions, to thereby re-orient and/or reposition the uterus (U). In this regard, controller (182) may monitor the manipulation of the uterus (U) based on the fluid pressure within balloon (324) as indicated by the feedback signals received by controller (182) from pressure sensor (874), and may take appropriate action in accordance therewith, such as adjusting the fluid pressure within balloon (324) and/or a position of balloon (324) to achieve the desired manipulation of the uterus (U), communicating the measured fluid pressure to the clinician, alerting the clinician that the measured fluid pressure has reached or exceeded a predetermined threshold, and/or alerting the clinician that the measured fluid pressure indicates inadvertent deflation of balloon (324).

In this regard, and as shown in FIG. 31, controller (182) may include a user interface (875) for communicating the measured fluid pressure to the clinician, alerting the clinician that the measured fluid pressure has reached or exceeded the predetermined threshold, and/or alerting the clinician that the measured fluid pressure indicates inadvertent deflation of balloon (324). User interface (875) may include a display screen, for example, or any other suitable user interface features for communicating with the clinician.

Figure 32:
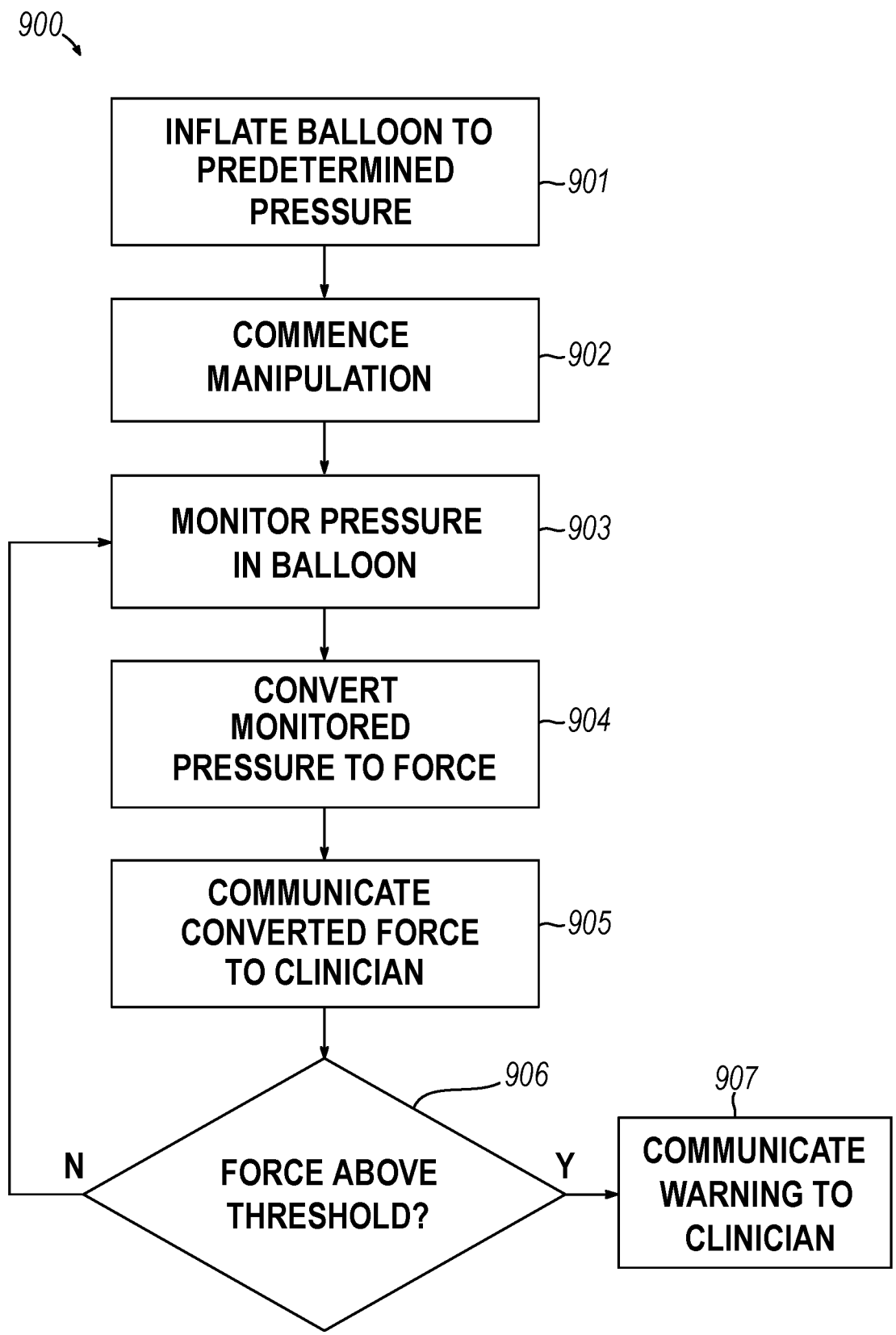
FIG. 32 depicts a flowchart of a method for monitoring the manipulation of a uterus using the uterine manipulator instrument of FIG. 31.

Referring now to FIG. 32, a method (900) of monitoring the manipulation of the uterus (U) begins with step (901), at which balloon (324) is inflated to a predetermined pressure, such as via pressurized fluid source (302). In some versions, the predetermined pressure may be selected to correspond to a point where balloon (324) bears outwardly against the sidewall of the uterus (U) and/or stabilizes the distal portion of shaft (320) relative to the uterus (U) without substantially re-orienting or repositioning the uterus (U). In other words, the predetermined pressure may be selected to define a neutral manipulation state of balloon (324). Method (900) proceeds from step (901) to step (902), at which point manipulation is commenced, such as by utilizing robotic arm (200) to drive uterine manipulator (800) to various positions, to thereby re-orient and/or reposition the uterus (U). Method (900) proceeds from step (902) to step (903), at which the fluid pressure in balloon (324) is continuously monitored, such as via controller (182) utilizing the feedback signals from pressure sensor (874). It will be appreciated that such continuous monitoring of the fluid pressure in balloon (324) may be performed contemporaneously (e.g., simultaneously) with the manipulation of step (902).

In any event, method (900) proceeds from step (903) to step (904), at which point the monitored fluid pressure is converted into a force measurement indicating the amount of force acting upon balloon (324) (e.g., exerted by the sidewalls of the uterus (U)), which may further indicate the amount of force imparted by balloon (324) against the wall of the uterus (U). Such a conversion of the fluid pressure value into a force measurement (step (904)) may be performed via controller (182). Method (900) proceeds from step (904) to step (905), at which point the converted force measurement is communicated to the clinician, such as via user interface (875) of controller (182). Method (900) proceeds from step (905) to step (906), at which point a determination is made whether the converted force measurement exceeds a predetermined threshold, such as via controller (182). If the converted force measurement exceeds the predetermined threshold, method (900) proceeds to step (907), at which point a warning is communicated to the clinician, such as via user interface (875) of controller (182). Such a warning may indicate that further manipulation may present an increased risk of perforation and/or that the uterus (U) has not yet been successfully mobilized due to a significant amount of connective tissue remaining, such that further dissection may be warranted before further manipulation of the uterus (U), for example. If the converted force measurement does not exceed the predetermined threshold, method (900) returns to step (903) for continuously monitoring the fluid pressure in balloon (324).

In some versions, method (900) may also include performing a comparison between a current force measurement and a previous force measurement, such as the force measurement immediately prior to the current force measurement, to determine whether the current force measurement is substantially lower than the previous force measurement. A warning may then be communicated to the clinician if the current force measurement is substantially lower than the previous force measurement. Such a warning may indicate that perforation has occurred. It will be appreciated that method (900) may include determining various other types of conditions associated with the manipulation of the uterus (U) via uterine manipulator (800). In some versions, the force that is driven axially (e.g., along an axis defined by shaft (320)) generally toward the fundus (F) may be compared to a first predetermined threshold to assess the risk of perforation in the manner described above. In addition, or alternatively, the force(s) driven transversely (e.g., up-down or side-to-side) may be compared to a second predetermined threshold to assess the mobility of the uterus (U) in the manner described above, such as by determining whether sufficient connective tissue has been freed from the bladder above the uterus (U) and/or from the rectum below the uterus (U) to permit manipulation of the uterus (U).

F. Exemplary Uterine Manipulator with Mechanical Traction Device

Figure 33A:
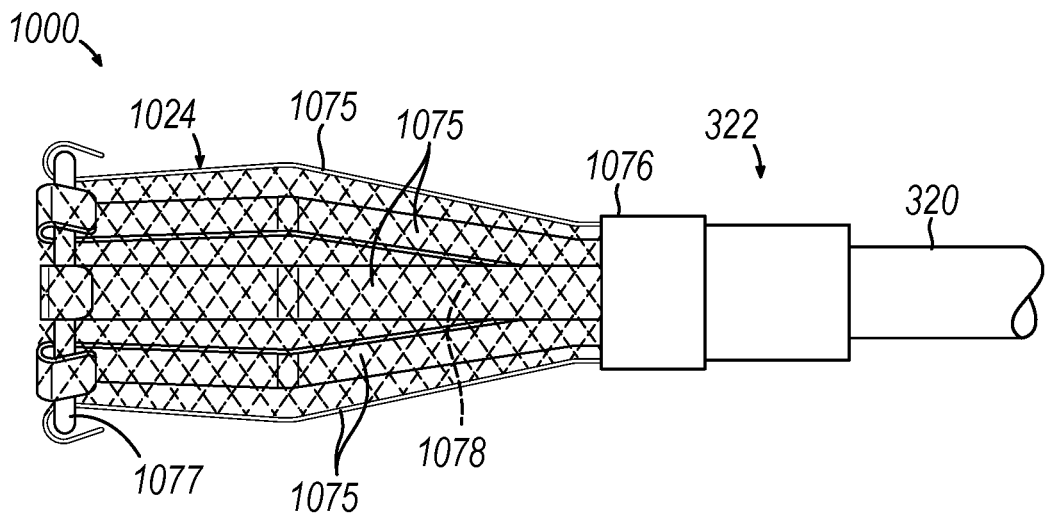
FIG. 33A depicts a side elevation view of a distal portion of another exemplary uterine manipulator instrument with a mechanical expandable member in an unexpanded state.
Figure 33B:
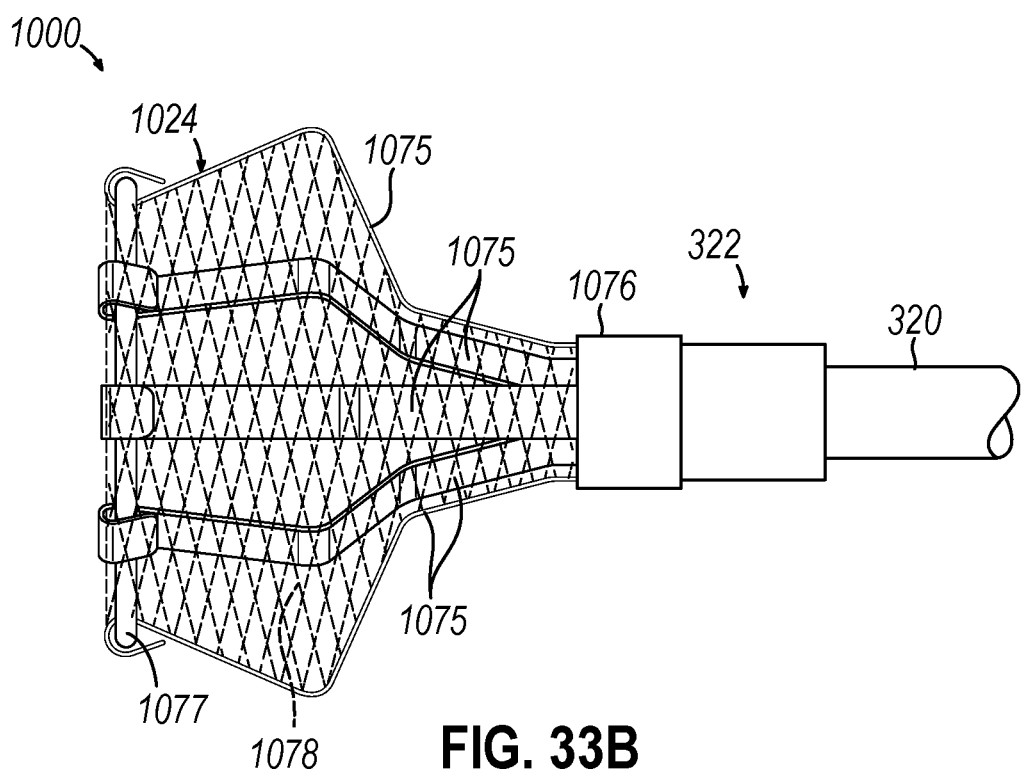
FIG. 33B depicts a side elevation view of a distal portion of the uterine manipulator instrument of FIG. 33A with the mechanical expandable member in an expanded state.

FIGS. 33A-33B depict a distal portion of another exemplary uterine manipulator (1000) for use with robotic arm (200). Uterine manipulator (1000) is similar to uterine manipulator (300) described above except as otherwise described below. In this regard, uterine manipulator (1000) includes a head interface assembly (not shown), such as head interface assembly (310), shaft (320), a traction member (1024) mechanically expandable from a first state (FIG. 33A) to a second state (FIG. 33B), a sleeve (not shown), such as sleeve (330), a proximal sealing balloon (not shown), such as balloon (332), a sleeve locking ring (not shown), such as sleeve locking ring (340), and a colpotomy cup (not shown), such as colpotomy cup (350). Traction member (1024) may serve as a substitute for distal balloon (324) of uterine manipulator (300). Uterine manipulator (1000) may be removably coupled with head (240) of robotic arm (200), such that robotic arm (200) may selectively position and orient uterine manipulator in relation to a patient by driving robotic arm (200).

Traction member (1024) of the present version includes a plurality of flexible fingers (1075) extending distally from a collar (1076) secured to distal end (322) of shaft (320) to a flexible ring (1077). An optional mesh webbing (1078) may extend between circumferentially-adjacent fingers (1075) and may be formed of nitinol, for example. Webbing (1078) may alternatively comprise an extensible membrane, a non-extensible flexible material, or any other suitable type of webbing. In any event, fingers (1075) may be configured to actuate robotically by the clinician via controller (182) for transitioning traction member (1024) between the first and second states. In some cases, traction member (1024) may be mechanically expanded to a point where traction member (1024) bears outwardly against the sidewall of the uterus (U). For example, a plurality of linkages may form an umbrella-type mechanism to expand traction member (1024), such that traction member (1024) may be expanded from the first state to the second state by retracting an actuator (e.g., a cable) relative to a stationary grounding feature (e.g., collar (1076)). In addition, or alternatively, traction member (1024) may be actuated between the first and second states by one or more push member(s) and/or pull member(s) operatively coupled to fingers (1075) and driven by controller (182) via head interface assembly (310).

In some other versions, traction member (1024) may be resiliently biased to assume the second state. For example, traction member (1024) may be compressed within a sheath during insertion into the uterus (U) to maintain traction member (1024) in the first state, and the sheath may be subsequently retracted to allow traction member (1024) to expand to the second state. In any case, the expanded traction member (1024) may stabilize the distal portion of shaft (320) relative to the uterus (U). Specifically, the expanded traction member (1024) may prevent shaft (320) from exiting proximally from the uterus (U) via the cervix (C). Traction member (1024) may thus serve as a distally-positioned anchor structure for uterine manipulator (300). The expanded traction member (1024) may also provide sufficient engagement between shaft (320) and the uterus (U) to allow use of shaft (320) to reposition and reorient the uterus (U) as described herein.

G. First Exemplary Uterine Manipulator with Distal Lighting

Figure 34:
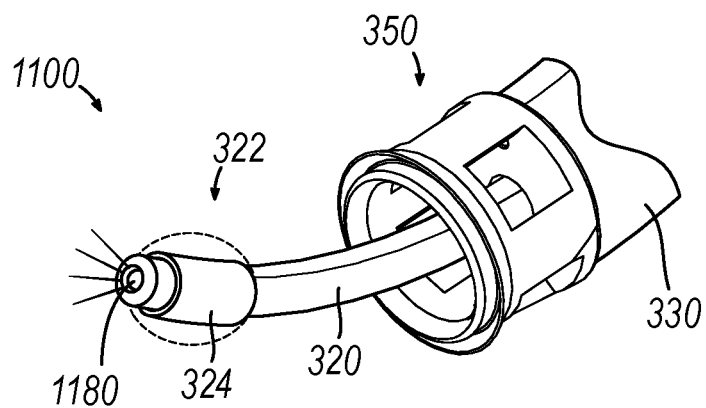
FIG. 34 depicts a perspective view of a distal portion of another exemplary uterine manipulator instrument with a light emitting diode (LED) disposed at a distal end of a shaft of the uterine manipulator instrument.

FIG. 34 depicts a distal portion of another exemplary uterine manipulator (1100) for use with robotic arm (200). Uterine manipulator (1100) is similar to uterine manipulator (300) described above except as otherwise described below. In this regard, uterine manipulator (1100) includes a head interface assembly (not shown), such as head interface assembly (310), shaft (320), balloon (324), sleeve (330), a proximal sealing balloon (not shown), such as balloon (332), a sleeve locking ring (not shown), such as sleeve locking ring (340), and colpotomy cup (350). Uterine manipulator (1100) may be removably coupled with head (240) of robotic arm (200), such that robotic arm (200) may selectively position and orient uterine manipulator in relation to a patient by driving robotic arm (200).

In the example shown, distal end (322) of shaft (320) includes an illuminating element in the form of a light emitting diode (LED) (1180) for illuminating the patient's anatomy distal of distal end (322) in a manner similar to that described above in connection with FIGS. 21-22. LED (1180) may be in operative communication with controller (182), such as via one or more wires extending along the lumen(s) of shaft (320), for receiving power and/or control signals from controller (182), for example. In this manner, LED (1180) may assist the clinician with observing the cervix (C) during insertion of uterine manipulator (1100) from the vagina (V) into the cervix (C). In some versions, a camera (not shown) may be positioned at distal end (322) of shaft (320) and may be in operative communication with controller (182) to enable visualization of the patient's anatomy distal of distal end (322) via a display screen of controller (182), for example. In addition, or alternatively, LED (1180) may provide transillumination through the wall of the uterus (U). Such transillumination may be observed via a laparoscope or other visualization device that is positioned external to the uterus (U), and may indicate the extent to which shaft (320) has been inserted into the uterus (U).

H. Second Exemplary Uterine Manipulator with Distal Lighting

Figure 35:
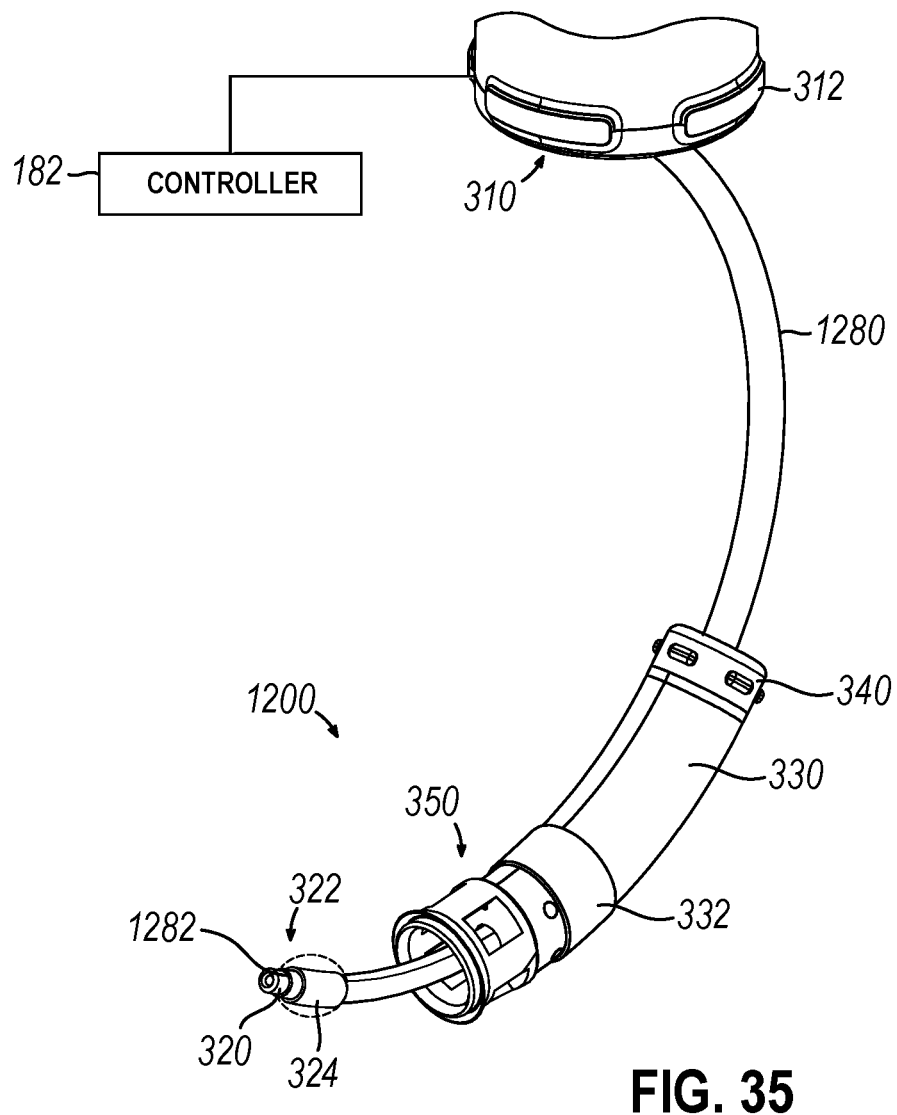
FIG. 35 depicts a perspective view of another exemplary uterine manipulator instrument with a lightpipe positioned over a shaft of the uterine manipulator instrument.

FIG. 35 depicts a distal portion of another exemplary uterine manipulator (1200) for use with robotic arm (200). Uterine manipulator (1200) is similar to uterine manipulator (300) described above except as otherwise described below. In this regard, uterine manipulator (1200) includes head interface assembly (310), shaft (320), balloon (324), sleeve (330), balloon (332), sleeve locking ring (340), and colpotomy cup (350). Uterine manipulator (1200) may be removably coupled with head (240) of robotic arm (200), such that robotic arm (200) may selectively position and orient uterine manipulator in relation to a patient by driving robotic arm (200).

Uterine manipulator (1200) of the present version includes an illuminating element in the form of a lightpipe (1280) fixedly positioned over shaft (320) and terminating at an annular opening (1282) at or near distal end (322) of shaft (320) for illuminating the patient's anatomy distal of distal end (322). In some versions, a lens (not shown) may be positioned at opening (1282). Lightpipe (1280) may receive light from a proximally-located light source (not shown) that is in operative communication with controller (182) for receiving power and/or control signals from controller (182), for example, and may convey such light to opening (1282). In this regard, lightpipe (1280) may be lined with a reflective material (not shown) to assist with the conveyance of light from the light source to opening (1282). Lightpipe (1280) may be hollow, or may be filled with an optically transmissive material. The light source may be incorporated into head interface assembly (310) and directly optically coupled with lightpipe (1280), or may be separate from head interface assembly (310) and optically coupled with lightpipe (1280) via an optical fiber, optical fiber bundle, or any other suitable optical conveyance structure for introducing light from the light source into lightpipe (1280). In this manner, lightpipe (1280) may assist the clinician with observing the cervix (C) during insertion of uterine manipulator (1200) from the vagina (V) into the cervix (C). In some versions, a camera (not shown) may be positioned at distal end (322) of shaft (320) and may be in operative communication with controller (182) to enable visualization of the patient's anatomy distal of distal end (322) via a display screen of controller (182), for example. In addition, or alternatively, lightpipe (1280) may provide transillumination through the wall of the uterus (U). Such transillumination may be observed via a laparoscope or other visualization device that is positioned external to the uterus (U), and may indicate the extent to which shaft (320) has been inserted into the uterus (U).

In some versions, lightpipe (1280) may include indicia, such as a scale, along its length for assisting with performing depth measurements and/or manually defining the RCM. In addition, or alternatively, lightpipe (1280) may be slightly compliant to permit one or more frictional braking structures of locking ring (340) to grip lightpipe (1280) in the locked state where the position of sleeve (330) along shaft (320) is secured. While lightpipe (1280) of the present version is positioned over an exterior of shaft (320), lightpipe (1280) may alternatively be positioned within an interior of shaft (320). For example, lightpipe (1280) may defined by an interior passageway of shaft (320). Also, while the illuminating element has been described in the form of lightpipe (1280), it will be appreciated that any other suitable illuminating element may be used, such as an optical fiber or an optical fiber bundle.

IV. Examples of Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft including a distal shaft end, wherein at least a portion of the shaft defines a first axis; (b) a sleeve slidably coupled to the shaft, wherein the sleeve includes a distal sleeve end; (c) a colpotomy cup fixedly secured to the distal sleeve end; and (d) a movable member extending distally from the distal shaft end, wherein the movable member is configured to move relative to the shaft between a first state in which the movable member extends substantially along the first axis and a second state in which the movable member extends at least partially along a second axis transverse to the first axis for manipulating an anatomical structure.

Example 2

The apparatus of Example 1, wherein the movable member includes at least one inflatable balloon.

Example 3

The apparatus of Example 2, wherein the at least one inflatable balloon comprises a non-extensible material, wherein the at least one inflatable balloon is configured to assume a predefined shape when the movable member is in the second state.

Example 4

The apparatus of any one or more of Examples 2 through 3, wherein the at least one inflatable balloon comprises an extensible material.

Example 5

The apparatus of any one or more of Examples 2 through 4, wherein the at least one inflatable balloon includes a plurality of inflatable members, wherein each member of the plurality of members is independently inflatable.

Example 6

The apparatus of any one or more of Examples 2 through 5, further comprising at least one pressure sensor configured to detect a fluid pressure within the at least one inflatable balloon, wherein the at least one pressure sensor is configured to generate at least one feedback signal based on the detected fluid pressure.

Example 7

The apparatus of any one or more of Examples 2 through 6, wherein the at least one inflatable balloon is configured to extend from a proximal position in which the at least one inflatable balloon is housed within the shaft to a distal position in which the at least one inflatable balloon extends distally from the distal shaft end.

Example 8

The apparatus of any one or more of Examples 1 through 7, wherein the movable member includes at least one articulatable finger.

Example 9

The apparatus of Example 8, wherein the at least one articulatable finger comprises a rigid material.

Example 10

The apparatus of any one or more of Examples 8 through 9, wherein the at least one articulatable finger is coupled to the distal shaft end via an articulation joint.

Example 11

The apparatus of Example 10, wherein the articulation joint includes at least one driver configured to selectively actuate articulation of the at least one articulatable finger relative to the shaft.

Example 12

The apparatus of any one or more of Examples 10 through 11, wherein the articulation joint includes at least one force sensor configured to detect a force acting upon the at least one articulatable finger, wherein the at least one force sensor is configured to generate at least one feedback signal based on the detected force.

Example 13

The apparatus of any one or more of Examples 8 through 12, further comprising an inflatable balloon positioned over the at least one articulatable finger.

Example 14

A system, comprising: (a) the apparatus of any one or more of Examples 1 through 13; (b) at least one sensor configured to detect at least one of a pressure or a force associated with the movable member, wherein the at least one sensor is configured to generate at least one feedback signal based on the detected at least one of a pressure or a force; and (c) a controller, wherein the controller is in operative communication with the at least one sensor for receiving the at least one feedback signal from the at least one sensor, wherein the controller is configured to monitor the manipulation of the anatomical structure by the movable member based on the at least one feedback signal.

Example 15

The system of Example 14, further comprising an actuator configured to actuate movement of the movable member between the first and second states, wherein the controller is in operative communication with the actuator for sending control signals to the actuator.

Example 16

A system, comprising: (a) an apparatus, comprising: (i) a shaft including a distal shaft end, wherein at least a portion of the shaft defines a first axis, (ii) a sleeve slidably coupled to the shaft, wherein the sleeve includes a distal sleeve end, (iii) a colpotomy cup fixedly secured to the distal sleeve end, and (iv) at least one inflatable balloon extending distally from the distal shaft end, wherein the at least one inflatable balloon is configured to inflate from a first state in which the at least one inflatable balloon extends substantially along the first axis and a second state in which the at least one inflatable balloon extends at least partially along a second axis transverse to the first axis for manipulating an anatomical structure; (b) at least one pressure sensor configured to detect a fluid pressure within the at least one inflatable balloon, wherein the at least one pressure sensor is configured to generate at least one feedback signal based on the detected fluid pressure; and (c) a controller, wherein the controller is in operative communication with the at least one pressure sensor for receiving the at least one feedback signal from the at least one pressure sensor, wherein the controller is configured to monitor the manipulation of the anatomical structure by the at least one inflatable balloon based on the at least one feedback signal.

Example 17

The system of Example 16, further comprising a pressurized fluid source configured to selectively inflate the at least one inflatable balloon from the first state to the second state, wherein the controller is in operative communication with the pressurized fluid source for sending control signals to the pressurized fluid source.

Example 18

The system of any one or more of Examples 16 through 17, wherein the at least one inflatable balloon is configured to extend from a proximal position in which the at least one inflatable balloon is housed within the shaft to a distal position in which the at least one inflatable balloon extends distally from the distal shaft end.

Example 19

A system, comprising: (a) an apparatus, comprising: (i) a shaft including a distal shaft end, wherein at least a portion of the shaft defines a first axis, (ii) a sleeve slidably coupled to the shaft, wherein the sleeve includes a distal sleeve end, (iii) a colpotomy cup fixedly secured to the distal sleeve end, and (iv) at least one articulatable finger extending distally from the distal shaft end, wherein the at least one articulatable finger is configured to articulate relative to the shaft between a first state in which the at least one articulatable finger extends substantially along the first axis and a second state in which the at least one articulatable finger extends at least partially along a second axis transverse to the first axis for manipulating an anatomical structure; (b) at least one force sensor configured to detect a force acting upon the at least one articulatable finger, wherein the at least one force sensor is configured to generate at least one feedback signal based on the detected force; and (c) a controller, wherein the controller is in operative communication with the at least one force sensor for receiving the at least one feedback signal from the at least one force sensor, wherein the controller is configured to monitor the manipulation of the anatomical structure by the at least one articulatable finger based on the at least one feedback signal.

Example 20

The system of Example 19, further comprising a driver configured to selectively actuate articulation of the at least one articulatable finger between the first state and the second state, wherein the controller is in operative communication with the driver for sending control signals to the driver.

Example 21

An apparatus, comprising: (a) a shaft including a distal shaft end; (b) a sleeve slidably coupled to the shaft, wherein the sleeve includes a distal sleeve end; (c) a colpotomy cup fixedly secured to the distal sleeve end; (d) an inflatable balloon positioned over the shaft near the distal shaft end such that the inflatable balloon is configured to manipulate an anatomical structure via movement of the shaft; and (e) at least one sensor configured to detect at least one of a fluid pressure within the inflatable balloon or a force acting upon the inflatable balloon, wherein the at least one sensor is configured to generate at least one feedback signal based on the detected at least one of a fluid pressure or a force.

Example 22

The apparatus of Example 21, wherein the at least one sensor is configured to detect a force acting upon the inflatable balloon, wherein the at least one sensor is configured to generate the feedback signal based on the detected force.

Example 23

The apparatus of Example 22, wherein the at least one sensor is positioned on an exterior of the inflatable balloon.

Example 24

The apparatus of Example 23, wherein the at least one sensor includes a plurality of sensors in a circumferential array on the exterior of the inflatable balloon.

Example 25

The apparatus of any one or more of Examples 22 through 24, wherein the at least one sensor includes at least one electrode configured to detect the force acting upon the inflatable balloon based on a change in resistance of the at least one electrode.

Example 26

The apparatus of Example 25, wherein the at least one electrode is compliant.

Example 27

The apparatus of any one or more of Examples 21 through 26, wherein the at least one sensor is configured to detect a fluid pressure within the inflatable balloon, wherein the at least one sensor is configured to generate the feedback signal based on the detected fluid pressure.

Example 28

The apparatus of Example 27, wherein the at least one sensor is positioned proximally relative to the inflatable balloon.

Example 29

The apparatus of Example 28, wherein the at least one sensor is positioned proximally relative to the shaft.

Example 30

The apparatus of Example 29, further comprising a pressurized fluid source configured to selectively inflate the inflatable balloon, wherein the at least one sensor is positioned inline between the shaft and the pressurized fluid source.

Example 31

A system, comprising: (a) the apparatus of any one or more of Examples 21 through 30; and (b) a controller, wherein the controller is in operative communication with the at least one sensor for receiving the at least one feedback signal from the at least one sensor, wherein the controller is configured to monitor the manipulation of the anatomical structure by the inflatable balloon based on the at least one feedback signal.

Example 32

The system of Example 31, wherein the at least one sensor is configured to detect the fluid pressure within the inflatable balloon, wherein the at least one sensor is configured to generate the feedback signal based on the detected fluid pressure, wherein the controller is configured to determine the force acting upon the inflatable balloon based on the detected fluid pressure.

Example 33

The system of any one or more of Examples 31 through 32, wherein the controller is configured to adjust at least one of the fluid pressure within the inflatable balloon or a position of the inflatable balloon based on the at least one feedback signal.

Example 34

The system of any one or more of Examples 31 through 33, wherein the controller is configured to determine whether the force acting upon the inflatable balloon exceeds a predetermined threshold.

Example 35

The system of Example 34, wherein the controller is configured to generate a warning in response to determining that the force acting upon the inflatable balloon exceeds the predetermined threshold.

Example 36

A system, comprising: (a) an apparatus, comprising: (i) a shaft including a distal shaft end, (ii) a sleeve slidably coupled to the shaft, wherein the sleeve includes a distal sleeve end, (iii) a colpotomy cup fixedly secured to the distal sleeve end, and (iv) an inflatable balloon positioned over the shaft near the distal shaft end such that the inflatable balloon is configured to manipulate an anatomical structure via movement of the shaft; (b) at least one sensor configured to generate at least one feedback signal indicative of a force acting upon the inflatable balloon; and (c) a controller, wherein the controller is in operative communication with the at least one sensor for receiving the at least one feedback signal from the at least one sensor, wherein the controller is configured to monitor the manipulation of the anatomical structure by the inflatable balloon based on the at least one feedback signal.

Example 37

The system of Example 36, wherein the at least one sensor is configured to detect a fluid pressure within the inflatable balloon, wherein the at least one sensor is configured to generate the feedback signal based on the detected fluid pressure, wherein the controller is configured to determine the force acting upon the inflatable balloon based on the detected fluid pressure.

Example 38

A method of operating an apparatus including (i) a shaft including a distal end, (ii) a sleeve slidably coupled to the shaft, and (iii) an inflatable balloon positioned over the shaft near the distal end, the method comprising: (a) inserting the inflatable balloon into a uterus of a patient; (b) inflating the inflatable balloon within the uterus; (c) moving the shaft such that the inflatable balloon manipulates the uterus; and (d) determining a force acting upon the inflatable balloon to monitor the manipulation of the uterus by the inflatable balloon.

Example 39

The method of Example 38, wherein the act of determining the force acting upon the inflatable balloon includes detecting the force acting upon the inflatable balloon via at least one force sensor.

Example 40

The method of Example 18, wherein the act of determining the force acting upon the inflatable balloon includes detecting a fluid pressure within the inflatable balloon via at least one pressure sensor and converting the detected fluid pressure to the force acting upon the inflatable balloon.

V. Miscellaneous

For clarity of disclosure, the terms "proximal" and "distal" are defined herein relative to a surgeon or other operator grasping a surgical instrument having a distal surgical end effector. The term "proximal" refers the position of an element closer to the surgeon or other operator and the term "distal" refers to the position of an element closer to the surgical end effector of the surgical instrument and further away from the surgeon or other operator.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

It should be understood that any of the versions of the instruments described herein may include various other features in addition to or in lieu of those described above. By way of example only, any of the devices herein may also include one or more of the various features disclosed in any of the various references that are incorporated by reference herein. Various suitable ways in which such teachings may be combined will be apparent to those of ordinary skill in the art.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. An apparatus, comprising:
   (a) a shaft including a distal shaft end, wherein at least a portion of the shaft defines a first axis;
   (b) a sleeve slidably coupled to the shaft, wherein the sleeve includes a distal sleeve end and proximal sleeve end;
   (c) a sleeve lock concentric with the shaft and rotatably secured to the proximal sleeve end;
   (d) a colpotomy cup fixedly secured to the distal sleeve end; and
   (e) a movable member extending distally from the distal shaft end, wherein the movable member is configured to move relative to the shaft between a first state in which the movable member extends substantially along the first axis and a second state in which the movable member extends at least partially along a second axis transverse to the first axis for manipulating an anatomical structure.

2. The apparatus of claim 1, wherein the movable member includes at least one inflatable balloon.

3. The apparatus of claim 2, wherein the at least one inflatable balloon comprises a non-extensible material, wherein the at least one inflatable balloon is configured to assume a predefined shape when the movable member is in the second state.

4. The apparatus of claim 2, wherein the at least one inflatable balloon comprises an extensible material.

5. The apparatus of claim 2, wherein the at least one inflatable balloon includes a plurality of inflatable members, wherein each member of the plurality of inflatable members is independently inflatable.

6. The apparatus of claim 2, further comprising at least one pressure sensor configured to detect a fluid pressure within the at least one inflatable balloon, wherein the at least one pressure sensor is configured to generate at least one feedback signal based on the detected fluid pressure.

7. The apparatus of claim 2, wherein the at least one inflatable balloon is configured to extend from a proximal position in which the at least one inflatable balloon is housed within the shaft to a distal position in which the at least one inflatable balloon extends distally from the distal shaft end.

8. The apparatus of claim 1, wherein the movable member includes at least one articulatable finger.

9. The apparatus of claim 8, wherein the at least one articulatable finger comprises a rigid material.

10. The apparatus of claim 8, wherein the at least one articulatable finger is coupled to the distal shaft end via an articulation joint.

11. The apparatus of claim 10, wherein the articulation joint includes at least one driver configured to selectively actuate articulation of the at least one articulatable finger relative to the shaft.

12. The apparatus of claim 10, wherein the articulation joint includes at least one force sensor configured to detect a force acting upon the at least one articulatable finger, wherein the at least one force sensor is configured to generate at least one feedback signal based on the detected force.

13. The apparatus of claim 8, further comprising an inflatable balloon positioned over the at least one articulatable finger.

14. A system, comprising:
   (a) the apparatus of claim 1;
   (b) at least one sensor configured to detect at least one of a pressure or a force associated with the movable member, wherein the at least one sensor is configured to generate at least one feedback signal based on the detected at least one of a pressure or a force; and
   (c) a controller, wherein the controller is in operative communication with the at least one sensor for receiving the at least one feedback signal from the at least one sensor, wherein the controller is configured to monitor the manipulation of the anatomical structure by the movable member based on the at least one feedback signal.

15. The system of claim 14, further comprising an actuator configured to actuate movement of the movable member between the first and second states, wherein the controller is in operative communication with the actuator for sending control signals to the actuator.

16. A system, comprising:
   (a) an apparatus, comprising:
      (i) a shaft including a distal shaft end, wherein at least a portion of the shaft defines a first axis,
      (ii) a sleeve slidably coupled to the shaft, wherein the sleeve includes a distal sleeve end and proximal sleeve end,
      (iii) a sleeve lock concentric with the shaft and rotatably secured to the proximal sleeve end;
      (iv) a colpotomy cup fixedly secured to the distal sleeve end, and
      (v) at least one inflatable balloon extending distally from the distal shaft end, wherein the at least one inflatable balloon is configured to inflate from a first state in which the at least one inflatable balloon extends substantially along the first axis and a second state in which the at least one inflatable balloon extends at least partially along a second axis transverse to the first axis for manipulating an anatomical structure;
   (b) at least one pressure sensor configured to detect a fluid pressure within the at least one inflatable balloon, wherein the at least one pressure sensor is configured to generate at least one feedback signal based on the detected fluid pressure; and
   (c) a controller, wherein the controller is in operative communication with the at least one pressure sensor for receiving the at least one feedback signal from the at least one pressure sensor, wherein the controller is configured to monitor the manipulation of the anatomical structure by the at least one inflatable balloon based on the at least one feedback signal.

17. The system of claim 16, further comprising a pressurized fluid source configured to selectively inflate the at least one inflatable balloon from the first state to the second state, wherein the controller is in operative communication with the pressurized fluid source for sending control signals to the pressurized fluid source.

18. The system of claim 16, wherein the at least one inflatable balloon is configured to extend from a proximal position in which the at least one inflatable balloon is housed within the shaft to a distal position in which the at least one inflatable balloon extends distally from the distal shaft end.

19. A system, comprising:
(a) an apparatus, comprising:
   (i) a shaft including a distal shaft end, wherein at least a portion of the shaft defines a first axis,
   (ii) a sleeve slidably coupled to the shaft, wherein the sleeve includes a distal sleeve end and proximal sleeve end,
   (iii) a sleeve lock concentric with the shaft and rotatably secured to the proximal sleeve end;
   (iv) a colpotomy cup fixedly secured to the distal sleeve end, and
   (v) at least one articulatable finger extending distally from the distal shaft end, wherein the at least one articulatable finger is configured to articulate relative to the shaft between a first state in which the at least one articulatable finger extends substantially along the first axis and a second state in which the at least one articulatable finger extends at least partially along a second axis transverse to the first axis for manipulating an anatomical structure;
(b) at least one force sensor configured to detect a force acting upon the at least one articulatable finger, wherein the at least one force sensor is configured to generate at least one feedback signal based on the detected force; and
(c) a controller, wherein the controller is in operative communication with the at least one force sensor for receiving the at least one feedback signal from the at least one force sensor, wherein the controller is configured to monitor the manipulation of the anatomical structure by the at least one articulatable finger based on the at least one feedback signal.

20. The system of claim 19, further comprising a driver configured to selectively actuate articulation of the at least one articulatable finger between the first state and the second state, wherein the controller is in operative communication with the driver for sending control signals to the driver.

* * * * *